(12) United States Patent
Sakasegawa et al.

(10) Patent No.: US 8,105,766 B2
(45) Date of Patent: Jan. 31, 2012

(54) METHOD OF MEASURING PYROPHOSPHATE

(75) Inventors: Shinichi Sakasegawa, Tokyo (JP); Yoshiaki Ikura, Tokyo (JP); Atsuhisa Nishimura, Anjo-shi (JP); Toshihiko Kumazawa, Kitanagoya (JP); Shigeyuki Imamura, Izunokuni (JP)

(73) Assignees: Asahi Kasei Pharma Corporation, Tokyo (JP); Ichibiki Co., Ltd., Nagoya-Shi (JP)

( * ) Notice: Subject to any disclaimer, the term of this patent is extended or adjusted under 35 U.S.C. 154(b) by 188 days.

(21) Appl. No.: 12/395,438

(22) Filed: Feb. 27, 2009

(65) Prior Publication Data

US 2009/0246783 A1 Oct. 1, 2009

(30) Foreign Application Priority Data

Feb. 28, 2008 (JP) ................. 2008-048289
Jan. 19, 2009 (JP) ................. 2009-008421

(51) Int. Cl.
*C12Q 1/00* (2006.01)
*C12Q 1/68* (2006.01)
*C12Q 1/48* (2006.01)
*C07K 17/00* (2006.01)

(52) U.S. Cl. ............... 435/4; 435/6.1; 435/15; 653/350

(58) Field of Classification Search ............... 435/4, 15, 435/6.1; 530/350
See application file for complete search history.

(56) References Cited

U.S. PATENT DOCUMENTS

| | | | | |
|---|---|---|---|---|
| 4,622,296 A | * | 11/1986 | Yamanishi et al. | ............. 435/26 |
| 4,971,903 A | * | 11/1990 | Hyman | ............... 435/6 |
| 5,250,416 A | * | 10/1993 | Ohno et al. | ............... 435/15 |
| 5,310,652 A | * | 5/1994 | Gelfand et al. | ............... 435/6 |
| 5,891,659 A | | 4/1999 | Murakami et al. | |
| 6,210,891 B1 | * | 4/2001 | Nyren et al. | ............... 435/6 |
| 6,232,075 B1 | * | 5/2001 | Williams | ............... 435/6 |
| 6,472,187 B1 | * | 10/2002 | Tonoike et al. | ............ 435/91.51 |
| 7,488,581 B2 | * | 2/2009 | Nakamura et al. | ............... 435/6 |
| 7,632,392 B2 | * | 12/2009 | Yukimasa et al. | ......... 205/777.5 |
| 2004/0142401 A1 | * | 7/2004 | Iwata et al. | .................... 435/14 |
| 2005/0227308 A1 | * | 10/2005 | Schindler et al. | ............... 435/26 |
| 2007/0166724 A1 | | 7/2007 | Bentwich et al. | |
| 2007/0166729 A1 | * | 7/2007 | Kambara et al. | .................. 435/6 |
| 2008/0076118 A1 | * | 3/2008 | Tooke et al. | ....................... 435/6 |
| 2008/0102469 A1 | * | 5/2008 | Kajiyama et al. | ................. 435/6 |
| 2008/0118921 A1 | | 5/2008 | Tisi et al. | |

FOREIGN PATENT DOCUMENTS

| | | |
|---|---|---|
| JP | 59-166099 | 9/1984 |
| JP | 2003-174900 | 6/2003 |
| JP | 2007-097471 | 10/2005 |
| JP | 2006-187251 | 7/2006 |
| JP | 2009-17876 | 1/2009 |

OTHER PUBLICATIONS

Arakawa et al., Development of bioluminescent pyrophosphate assay using pyruvate phosphate dikinase and its application to single-nucleotide polymorphism analysis. Analytical Biochemistry 379 : 86-90 (2008).*

Magni et al., Structure and function of nicotinamide mononucleotide adenylyltransferase. Current Medicinal Chemistry 11(7), 873-885 (2004).*

Rao et al., A recycling assay for alkaline phosphatase applied to studies on its transport in *E. coli* K12 Journal of Biochemical and Biophysical Methods 19(4) : 301-8 (1989).*

Ronaghi et al., A sequencing method based on real-time pyrophosphate. Science 281(5375) : 363-365 (1998).*

Sakakibara et al., An enzymatic cycling method using pyruvate orthophosphate dikinase and firefly luciferase for the simultaneous determination of ATP and AMP (RNA). Analytical Biochemistry 268(1) : 94-101(1999).*

Sakuraba et al., A nicotinamide mononucleotide adenylyltransferase with unique adenylyl group donor specificity from a hyperthermophilic archaeon, Pyrococcus horikoshii OT-3. Journal of Molecular Catalysis B: Enzymatic 23(2-6) : 273-279 (2003).*

Singh et al., Catalase-peroxidases (KatG) exhibit NADH oxidase activity. Journal of Biological Chemistry 279 (41) : 43098-43106 (2004).*

Identification and characterization of a second NMN adenylyltransferase gene in *Saccharomyces cerevisiae*. Protein Expression and Purification, 27 (2003) 357-364.

* cited by examiner

*Primary Examiner* — Ethan C Whisenant
(74) *Attorney, Agent, or Firm* — Birch, Stewart, Kolasch & Birch, LLP

(57) ABSTRACT

Provided is a novel and useful method of measuring pyrophosphate in a sample. There may be provided a novel and useful method of measuring pyrophosphate in a sample using pyruvate orthophosphate dikinase, nicotinamide-nucleotide adenylyltransferase, and dehydrogenase.

19 Claims, 10 Drawing Sheets

[FIG. 2]
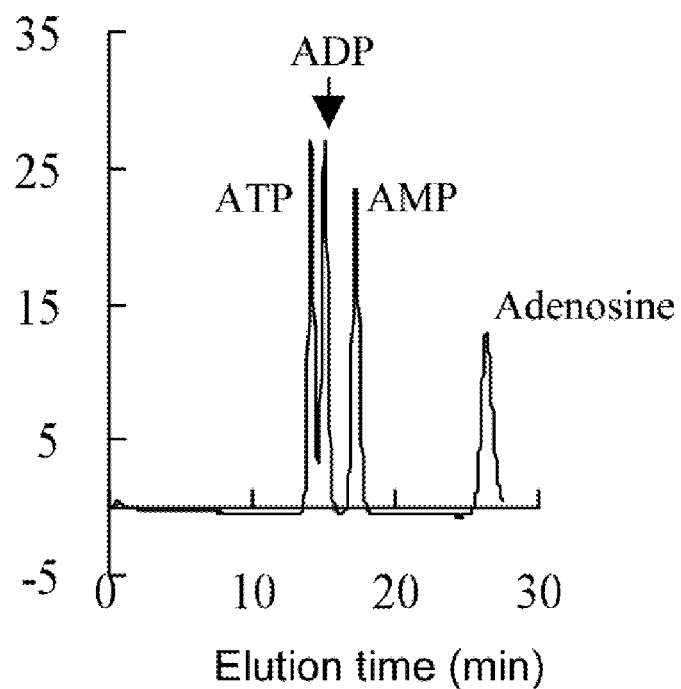
[FIG. 3]
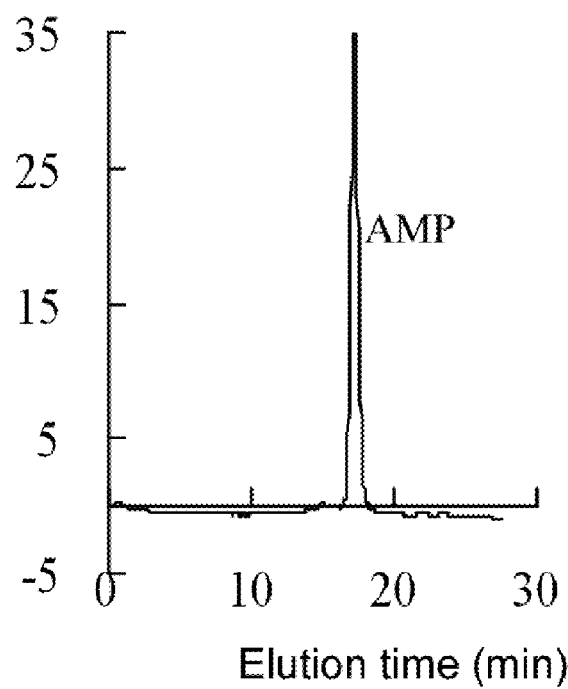

[FIG. 4]
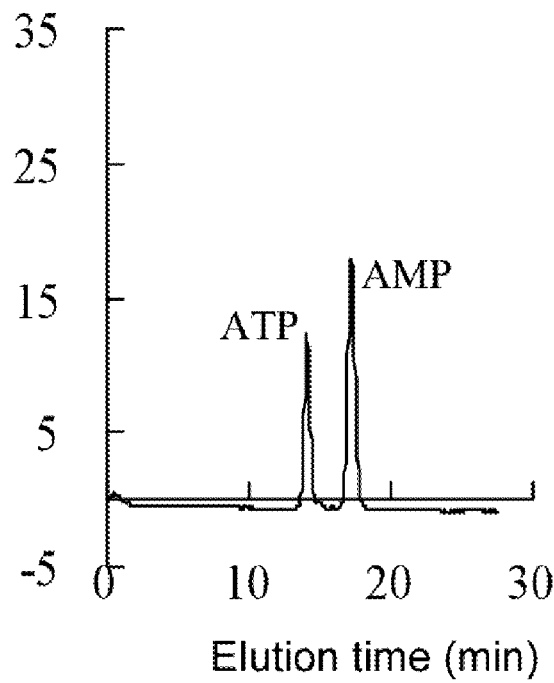
[FIG. 5]
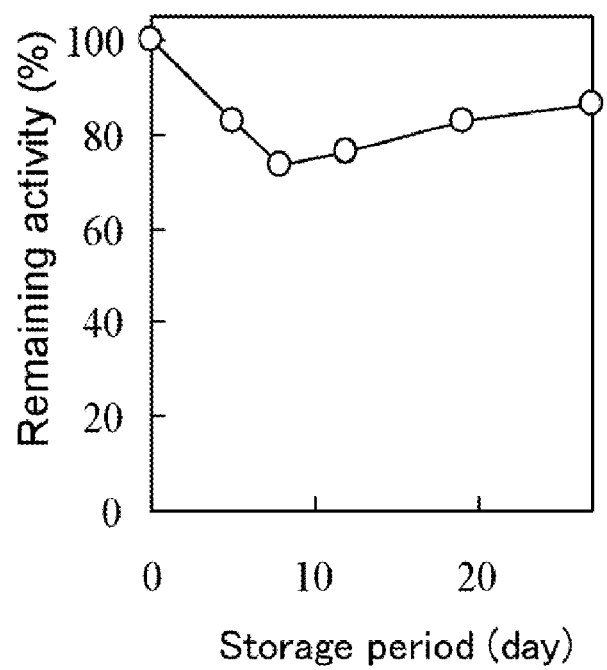

[FIG. 6]
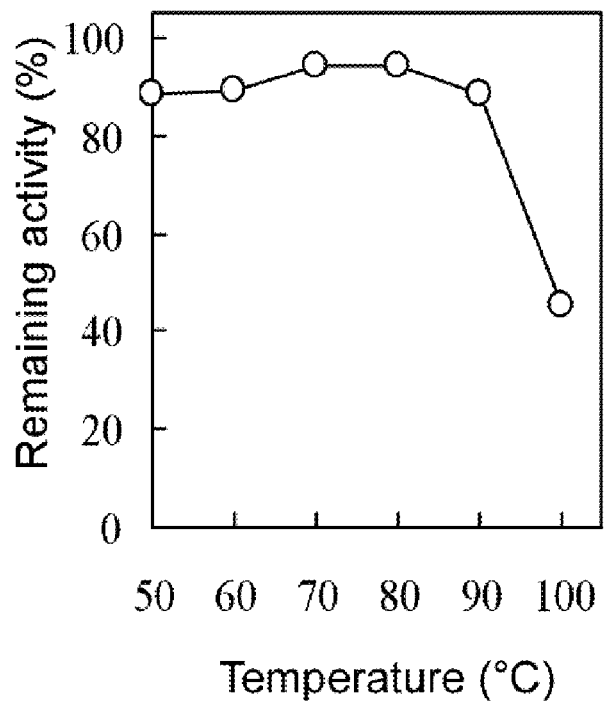
[FIG. 7]
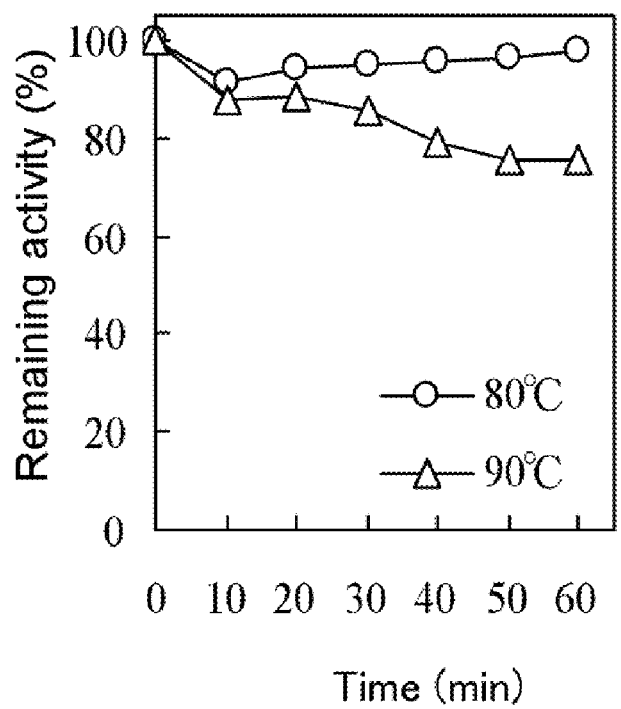

[FIG. 8]
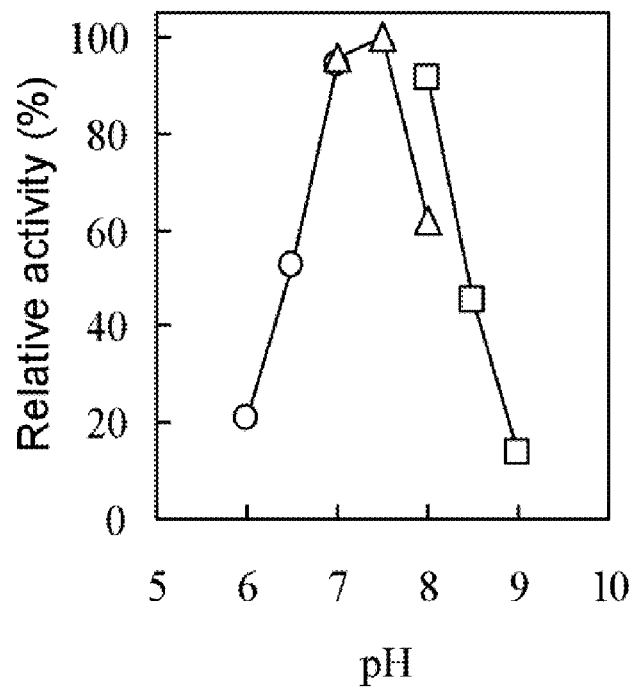
[FIG. 9]
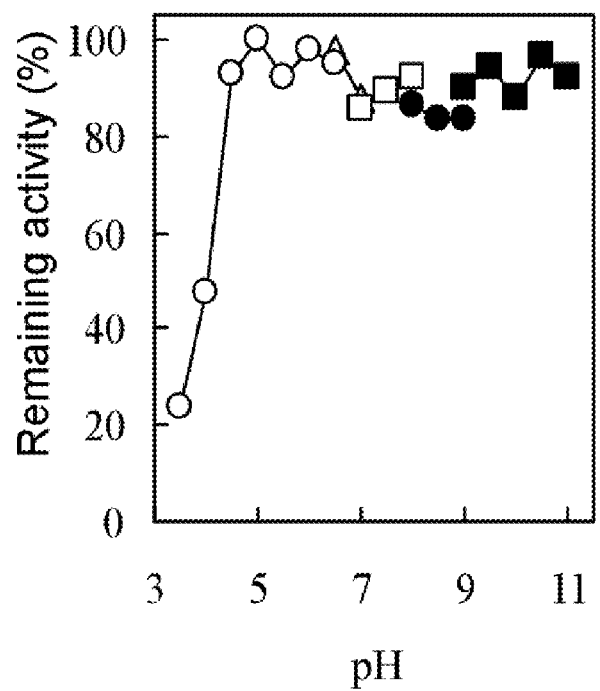

[FIG. 10]
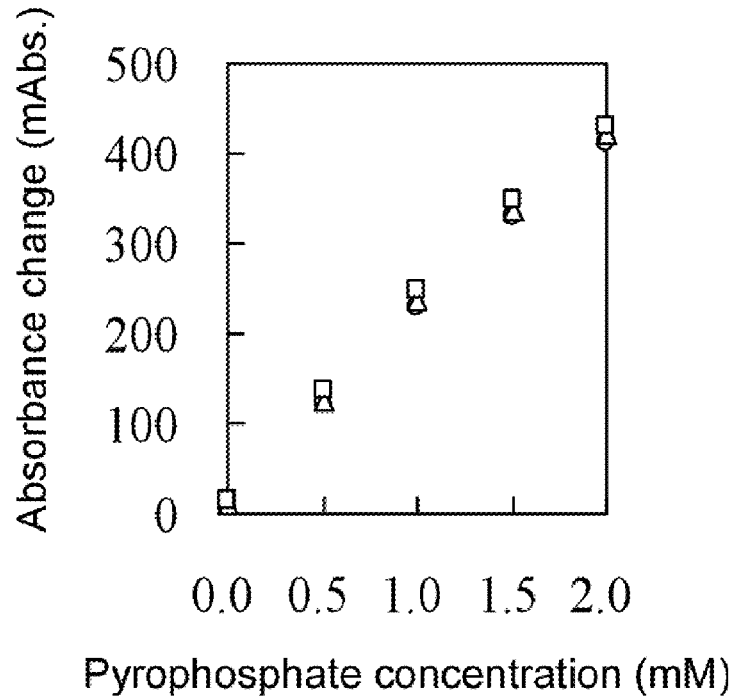
[FIG. 11]
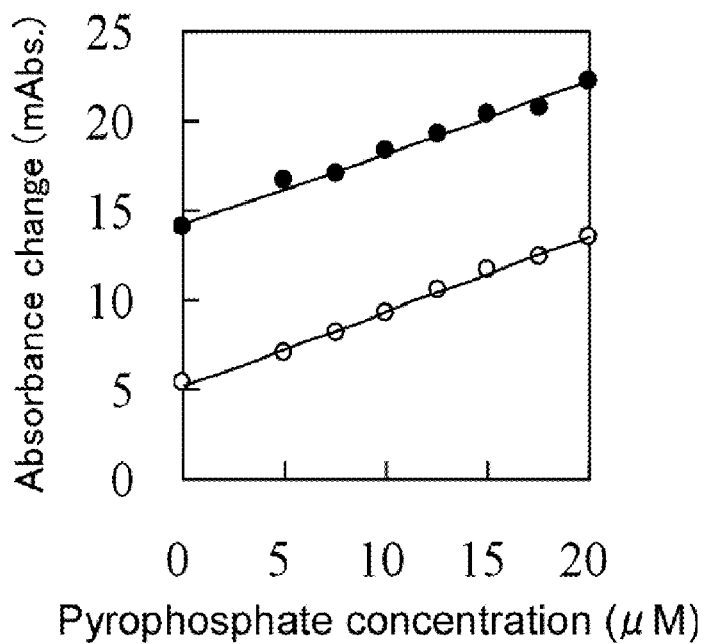

[FIG. 12]
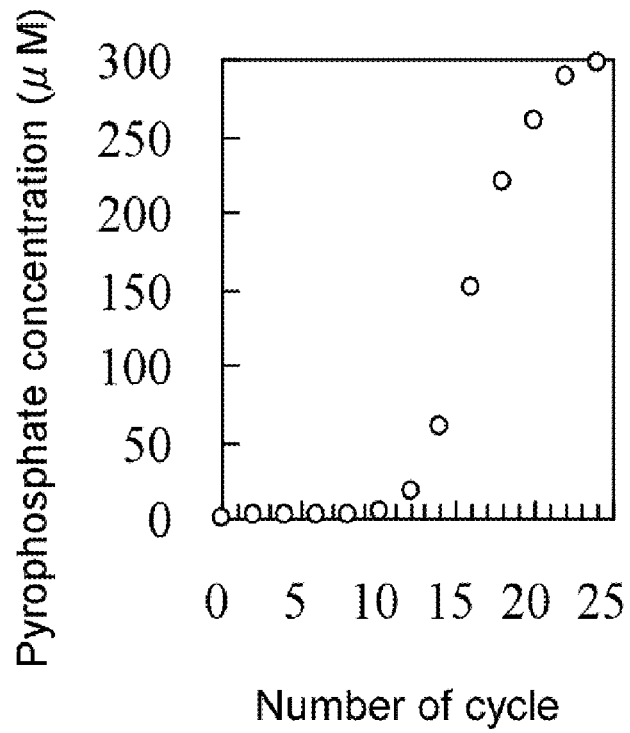
[FIG. 13]
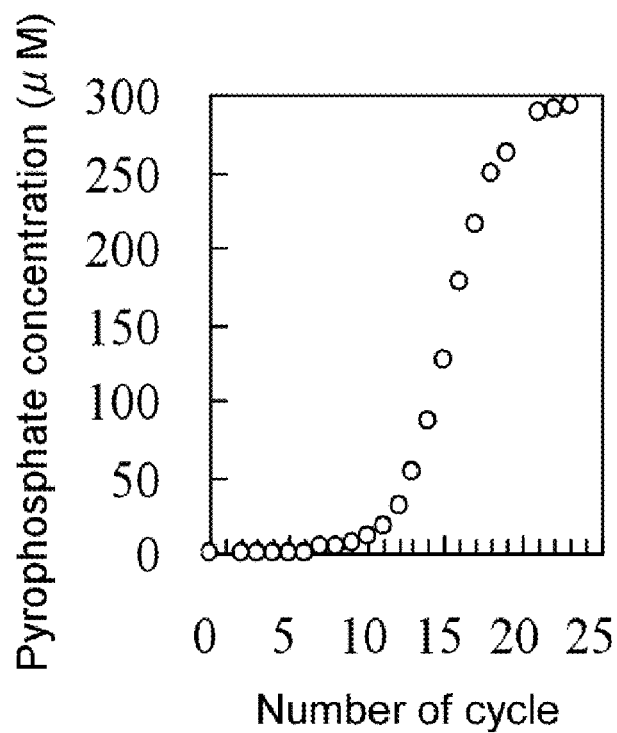

[FIG. 15]
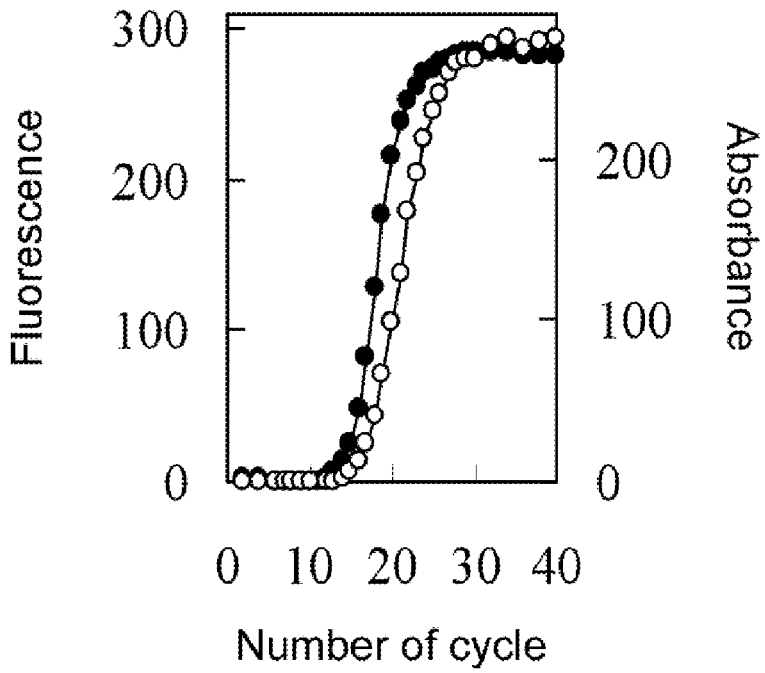
[FIG. 16]
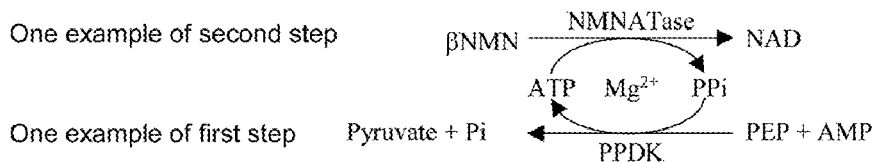
[FIG. 17]
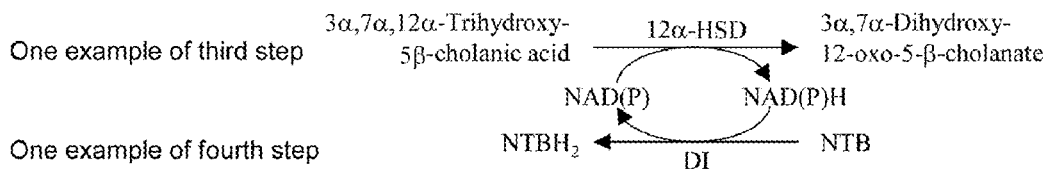

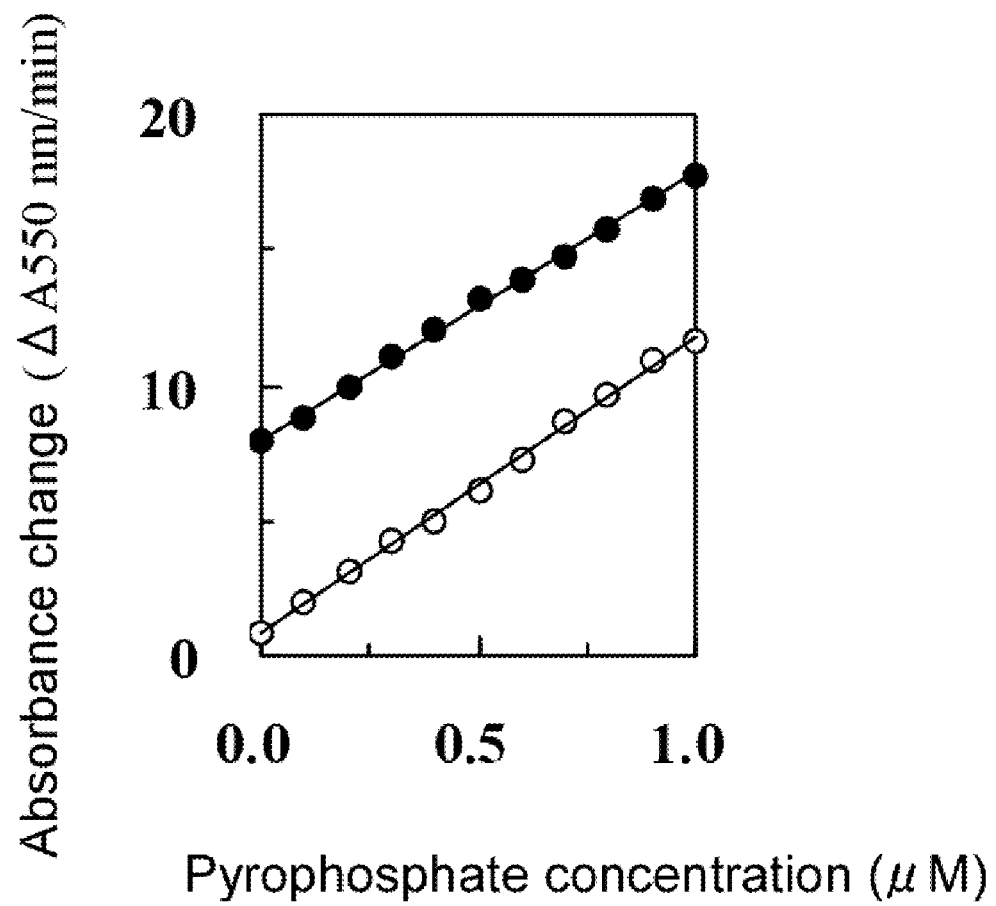
[FIG. 18]

METHOD OF MEASURING PYROPHOSPHATE

CROSS-REFERENCE TO RELATED APPLICATION

The present application claims priority and the benefit thereof under 35 U.S.C. 119, based on Japanese Patent Application No. 2008-048289 filed on Feb. 28, 2008, and Japanese Patent Application No. 2009-008421 filed on Jan. 19, 2009, the content of which is hereby incorporated by reference into this application.

BACKGROUND OF THE INVENTION

1. Field of the Invention

The present invention relates to a method of measuring pyrophosphate.

2. Description of the Related Art

As conventional techniques of measuring pyrophosphate enzymatically, there are known, for example, (i) a method involving using pyruvate orthophosphate dikinase and luciferase (Japanese Patent Application Laid-Open No. 2007-097471), (ii) a method involving using hypoxanthine phosphoribosyltransferase and xanthine dehydrogenase/oxidase (Japanese Patent Application Laid-Open No. 2003-174900), and (iii) a method involving using kinase, an enzyme for producing ATP from pyrophosphate, and dehydrogenase which requires NAD or NADP as a coenzyme (Japanese Patent Application Laid-Open No. 2006-187251).

SUMMARY OF THE INVENTION

It is an object of the present invention to provide a novel and useful method of measuring pyrophosphate in a sample.

The inventors of the present invention have found out a novel method of measuring pyrophosphate in a sample using pyruvate orthophosphate dikinase, nicotinamide-nucleotide adenylyltransferase, and dehydrogenase. Then, the inventors have succeeded in modifying the method into a sensitive and easy method using NAD cycling reaction. Moreover, the inventors have discovered nicotinamide-nucleotide adenylyltransferase which reacts selectively with ATP compared with triphosphorylated deoxyribonucleic acids (hereinafter, sometimes referred to as "dNTPs"), and have established a method of selectively measuring pyrophosphate in a sample using the enzyme even in the case where dNTPs, phosphate, and the like are present in one or two or more steps selected from the steps including the first to fourth reactions above, thus completing the present invention.

That is, the present invention relates to the following items.

[1]

A method of selectively measuring pyrophosphate in a sample including the following steps (1) to (4):

(1) a step including a first reaction for producing ATP by bringing pyrophosphate which may be present in the sample into contact with pyruvate orthophosphate dikinase in the presence of at least AMP;

(2) a step including a second reaction for producing pyrophosphate and NADs by bringing the ATP produced by the first reaction into contact with nicotinamide-nucleotide adenylyltransferase;

(3) a step including a third reaction for reducing the NADs produced by the second reaction into NADHs; and (4) a step of detecting the NADHs produced by the third reaction.

[1-1]

A method of selectively measuring pyrophosphate in a sample according to the item [1], wherein the step of detecting the NADHs produced by the third reaction includes the following steps:

(5) a step including a fourth reaction for converting the NADHs produced by the third reaction into a reduced nitroblue tetrazolium salt and NADs in the presence of a nitroblue tetrazolium salt; and (6) a step of detecting the reduced nitroblue tetrazolium salt produced by the fourth reaction.

[1-2]

A method of selectively measuring pyrophosphate in a sample according to the item [1-1] above, wherein the NADs produced by the fourth reaction is used in the third reaction to perform a cycling reaction between the third reaction and the fourth reaction.

[1-3]

A method of selectively measuring pyrophosphate in a sample according to any one of the items [1], [1-1], and [1-2] above, wherein the pyrophosphate produced by the second reaction is used in the first reaction to perform a cycling reaction between the first reaction and the second reaction.

[1-4]

A method of selectively measuring pyrophosphate according to any one of the items [1] and [1-1] to [1-3] above, in which the first reaction is a reaction further including a metal ion.

[1-5]

A method of selectively measuring pyrophosphate according to the item [1-4] above, in which the metal ion is one or two or more ions selected from the group consisting of a magnesium ion, a cobalt ion, and a nickel ion.

[1-6]

A method of selectively measuring pyrophosphate according to any one of the items [1] and [1-1] to [1-5] above, in which the first reaction is a reaction further including phosphoenolpyruvate (herein, sometimes referred to as "PEP").

[1-7]

A method of selectively measuring pyrophosphate according to any one of the items [1] and [1-1] to [1-6] above, in which the second reaction is a reaction further including a metal ion.

[1-8]

A method of selectively measuring pyrophosphate according to the item [1-7] above, in which the metal ion included in the second reaction is one or two or more ions selected from the group consisting of a magnesium ion, a cobalt ion, and a nickel ion.

[1-9]

A method of selectively measuring pyrophosphate according to any one of the items [1] and [1-1] to [1-8] above, in which the second reaction is a reaction further including β-nicotinamide mononucleotides (herein, sometimes referred to as "NMNs").

[1-10]

A method of selectively measuring pyrophosphate according to any one of the items [1] and [1-1] to [1-9] above, in which the pyruvate orthophosphate dikinase is any of the following enzymes [1] to [3]:

[1] an enzyme which has an amino acid sequence of SEQ ID NO: 1 and may catalyze the first reaction;

[2] an enzyme which has the amino acid sequence of SEQ ID NO: 1 with deletion, substitution, or addition of one or several amino acids, the amino acid sequence including an amino acid sequence of SEQ ID NO: 4 and an and amino acid sequence of SEQ ID NO: 5, and may catalyze the first reaction; and

[3] an enzyme which has the following physicochemical properties <<1>> to <<5>> and may catalyze the first reaction.

<<1>> Optimum pH
In the range from pH 7 to 7.5;

<<2>> pH Stability
The activity is maintained to 80% or more after a treatment at 50° C. for 20 minutes in the range of pH 4.5 to 11;

<<3>> Thermostability
The activity is maintained to 90% or more after a heat treatment at 80° C. for 1 hour and is maintained to 70% or more even after storage at 4° C. for at least 27 days;

<<4>> Coenzyme Specificity
The enzyme acts as an coenzyme specifically with adenosine 5'-monophosphate (herein, sometimes referred to as "AMP") in the case where PEP and pyrophosphate are used as substrates in the presence of magnesium ions and does not react with adenosine 5'-diphosphate, inosine 5'-monophosphate, cytidine 5'-monophosphate, guanosine 5'-monophosphate, thymidine 5'-monophosphate, or uridine 5'-monophosphate (herein, sometimes referred to as "ADP", "IMP", "CMP", "GMP", "TMP", and "UMP", respectively);

<<5>> Substrate Specificity
Pyrophosphate is a specific substrate.

[1-11]
A method of selectively measuring pyrophosphate according to any one of the items [1] and [1-1] to [1-10] above, in which the pyruvate orthophosphate dikinase has an amino acid sequence of SEQ ID NO: 1 and may catalyze the first reaction.

[1-12]
A method of selectively measuring pyrophosphate according to any one of the items [1] and [1-1] to [1-11] above, in which pyruvate orthophosphate dikinase is an enzyme which has an amino acid sequence of SEQ ID NO: 1 with deletion, substitution, or addition of one or several amino acids, the amino acid sequence including an amino acid sequence of SEQ ID NO: 4 and an and amino acid sequence of SEQ ID NO: 5, and may catalyze the first reaction.

[1-13]
A method of selectively measuring pyrophosphate according to any one of the items [1] and [1-1] to [1-12] above, in which the pyruvate orthophosphate dikinase is an enzyme which has the following physicochemical properties <<1>> to <<5>> and may catalyze the first reaction.

<<1>> Optimum pH
In the range from pH 7 to 7.5;

<<2>> pH Stability
The activity is maintained to 80% or more after a treatment at 50° C. for 20 minutes in the range of pH 4.5 to 11;

<<3>> Thermostability
The activity is maintained to 90% or more after a heat treatment at 80° C. for 1 hour and is maintained to 70% or more even after storage at 4° C. for at least 27 days;

<<4>> Coenzyme Specificity
The enzyme acts as an coenzyme specifically with AMP in the case where PEP and pyrophosphate are used as substrates in the presence of magnesium ions and does not react with ADP, IMP, CMP, GMP, TMP, or UMP;

<<5>> Substrate Specificity
Pyrophosphate is a specific substrate.

[1-14]
A method of selectively measuring pyrophosphate according to any one of the items [1] and [1-1] to [1-13] above, in which the pyruvate orthophosphate dikinase further has any one of the following physicochemical properties <<6>> and <<7>>.

<<6>> Frozen Storage Stability
The activity is maintained to 90% or more after storage at −20° C. for 2 weeks;

<<7>> Refrigerated Storage Stability
The activity is maintained to 80% or more after storage at 4° C. for 27 days.

[1-15]
A method of selectively measuring pyrophosphate according to any one of the items [1] and [1-1] to [1-14] above, in which the pyruvate orthophosphate dikinase is derived from the genus *Thermotoga*.

[1-16]
A method of selectively measuring pyrophosphate according to any one of the items [1] and [1-1] to [1-15] above, in which the pyruvate orthophosphate dikinase is derived from *Thermotoga maritima*.

[1-17]
A method of selectively measuring pyrophosphate according to any one of the items [1] and [1-1] to [1-16] above, in which pyruvate orthophosphate dikinase is derived from *Thermotoga maritima* DSM 3109 strain.

[1-18]
A method of selectively measuring pyrophosphate according to any one of the items [1] and [1-1] to [1-11] or [1-13] to [1-17] above, in which the base sequence encoding the pyruvate orthophosphate dikinase is a base sequence set forth in SEQ ID NO: 2 or SEQ ID NO: 3.

[1-19]
A method of selectively measuring pyrophosphate according to any one of the items [1] and [1-1] to [1-18] above, wherein the nicotinamide-nucleotide adenylyltransferase is any of the following enzymes [1] and [2]:

[1] an enzyme which has an amino acid sequence of SEQ ID NO: 6 and may catalyze the second reaction;

[2] an enzyme which has an amino acid sequence of SEQ ID NO: 6 with deletion, substitution, or addition of one or several amino acids and may catalyze the second reaction.

[1-20]
A method of selectively measuring pyrophosphate according to any one of the items [1] and [1-1] to [1-19] above, in which the nicotinamide-nucleotide adenylyltransferase is an enzyme which has an amino acid sequence of SEQ ID NO: 6 with one or more amino acid substitutions selected from the following <a> to <e> and may catalyze the second reaction.

<a> V132I (which means that I is substituted for V on position 132 in SEQ ID NO: 6.)
<b> D269V (which means that V is substituted for D on position 269 in SEQ ID NO: 6.)
<c> N64Y (which means that Y is substituted for N on position 64 in SEQ ID NO: 6.)
<d> A65S (which means that S is substituted for A on position 65 in SEQ ID NO: 6.)
<e> A103S (which means that S is substituted for A on position 103 in SEQ ID NO: 6.)

[1-21]
A method of selectively measuring pyrophosphate according to any one of the items [1] and [1-1] to [1-20] above, in which the base sequence encoding the nicotinamide-nucleotide adenylyltransferase is a base sequence set forth in SEQ ID NO: 7.

[1-22]
A method of selectively measuring pyrophosphate according to any one of the items [1] and [1-1] to [1-21] above, in which the nicotinamide-nucleotide adenylyltransferase is derived from an eukaryotic organism.

[1-23]
A method of selectively measuring pyrophosphate according to any one of the items [1] and [1-1] to [1-22] above, in which the nicotinamide-nucleotide adenylyltransferase is derived from a yeast.

[1-24]
A method of selectively measuring pyrophosphate according to any one of the items [1] and [1-1] to [1-23] above, in which the nicotinamide-nucleotide adenylyltransferase is derived from the genus *Saccharomyces*.

[1-25]
A method of selectively measuring pyrophosphate according to any one of the items [1] and [1-1] to [1-24] above, in which the nicotinamide-nucleotide adenylyltransferase is derived from *Saccharomyces cerevisiae*.

[1-26]
A method of selectively measuring pyrophosphate according to any one of the items [1] and [1-1] to [1-25] above, in which the nicotinamide-nucleotide adenylyltransferase has a substrate specificity ratio for dNTPs and ATP (substrate specificity for dNTPs/substrate specificity for ATP) of 5% or less.

[1-27]
A method of selectively measuring pyrophosphate according to any one of the items [1] and [1-1] to [1-26] above, in which the third reaction is a reaction that is catalyzed with an enzyme capable of reducing NADs into NADHs.

[1-28]
A method of selectively measuring pyrophosphate according to any one of the items [1] and [1-1] to [1-27] above, in which the third reaction is a reaction that is catalyzed with 12α-hydroxysteroid dehydrogenase.

[1-29]
A method of selectively measuring pyrophosphate according to any one of the items [1] and [1-1] to [1-28] above, in which the reduced NADH substance in the fourth reaction is diaphorase (herein, sometimes referred to as "DI").

[1-30]
A method of selectively measuring pyrophosphate according to any one of the items [1] and [1-1] to [1-29] above, in which the sample contains dNTPs.

[1-31]
A method of selectively measuring pyrophosphate according to any one of the items [1] and [1-1] to [1-29] above, in which one or two or more steps selected from the steps including the first to fourth reactions are steps including the dNTPs.

[1-32]
A method of selectively measuring pyrophosphate according to the item [1-30] or [1-31] above, in which the dNTPs include one or two or more nucleotides selected from the group consisting of dATP, dGTP, dCTP, and dTTP.

[1-33]
A method of selectively measuring pyrophosphate according to the item [1-30] or [1-31], in which the dNTPs include a mixture of at least dATP, dGTP, dCTP, and dTTP.

[1-34]
A method of selectively measuring pyrophosphate according to any one of the items [1-30] to [1-33] above, in which the respective concentrations of the dNTPs are 0.4 mM or less.

[2]
A method of detecting or quantifying a nucleic acid, which includes measuring, by a method according to any one of the items [1] and [1-1] to [1-34] above, pyrophosphate in a sample subjected to nucleic acid amplification or a sample prepared from the sample.

[2-1]
A method of detecting or quantifying a nucleic acid, which includes: measuring, by a method according to any one of the items [1] and [1-1] to [1-34] above, pyrophosphate in a sample subjected to nucleic acid amplification or a sample prepared from the sample; and subtracting a value of the pyrophosphate in the sample before nucleic acid amplification as a blank value.

[2-2]
A method of detecting or quantifying a nucleic acid using the amount of produced pyrophosphate as an index, which includes measuring, by a method according to any one of the items [1], [1-1] to [1-34], [2], and [2-1] above, pyrophosphate obtained as a product of the nucleic acid amplification.

[2-3]
A method of detecting or quantifying a nucleic acid using the amount of produced pyrophosphate as an index, which includes: measuring, by a method according to any one of the items [1], [1-1] to [1-34], [2], and [2-1] to [2-2] above, pyrophosphate obtained as a product of the nucleic acid amplification; and subtracting a value of the pyrophosphate in the sample before nucleic acid amplification as a blank value.

[3]
A composition including at least the following components (1) to (7):
 (1) a metal ion;
 (2) AMP;
 (3) PEP
 (4) pyruvate orthophosphate dikinase;
 (5) NMNs
 (6) nicotinamide-nucleotide adenylyltransferase; and
 (7) a reduced NAD substance.

[3-1]
A composition according to the item [3] above, further including the following components (8) and (9):
 (8) an oxidized NADH substance; and
 (9) nitroblue tetrazolium salts (herein, sometimes referred to as "NTBs").

[3-2]
A composition including the following two reagents (A) and (B):
(A) A First Reagent Containing at Least the Following Components (1) to (4):
 (1) a metal ion;
 (2) AMP;
 (3) PEP;
 (4) pyruvate orthophosphate dikinase;
(B) A Second Reagent Containing at Least the Following Components (5) to (7):
 (5) NMNs
 (6) nicotinamide-nucleotide adenylyltransferase; and
 (7) a reduced NAD substance.

[3-3]
A composition according to the item [3-2] above, further including the following components (8) and (9) in the second reagent:
 (8) an oxidized NADH substance; and
 (9) NTBs.

[3-4]
A composition according to any one of the items [3] and [3-1] to [3-3] above, in which the metal ion is one of the ions selected from a magnesium ion, a cobalt ion, and a nickel ion.

[3-5]
A composition according to any one of the items [3] and [3-1] to [3-4] above, in which the pyruvate orthophosphate dikinase is any of the following enzymes [1] to [3]:

[1] an enzyme which has an amino acid sequence of SEQ ID NO: 1 and may catalyze the first reaction;

[2] an enzyme which has an amino acid sequence of SEQ ID NO: 1 with deletion, substitution, or addition of one or several amino acids, the amino acid sequence including an amino acid sequence of SEQ ID NO: 4 and an and amino acid sequence of SEQ ID NO: 5, and may catalyze the first reaction; and

[3] an enzyme which has the following physicochemical properties <<1>> to <<5>> and may catalyze the first reaction.

<<1>> Optimum pH

In the range from pH 7 to 7.5;

<<2>> pH Stability

The activity is maintained to 80% or more after a treatment at 50° C. for 20 minutes in the range of pH 4.5 to 11;

<<3>> Thermostability

The activity is maintained to 90% or more after a heat treatment at 80° C. for 1 hour and is maintained to 70% or more after storage at 4° C. for at least 27 days;

<<4>> Coenzyme Specificity

The enzyme acts as an coenzyme specifically with AMP in the case where PEP and pyrophosphate are used as substrates in the presence of magnesium ions and does not react with ADP, IMP, CMP, GMP, TMP, or UMP;

<<5>> Substrate Specificity

Pyrophosphate is a specific substrate.

[3-6]

A composition according to any one of the items [3] and [3-1] to [3-5] above, in which the pyruvate orthophosphate dikinase is an enzyme which has an amino acid sequence of SEQ ID NO: 1 and may catalyze the first reaction.

[3-7]

A composition according to any one of the items [3] and [3-1] to [3-6] above, in which pyruvate orthophosphate dikinase is an enzyme which has an amino acid sequence of SEQ ID NO: 1 with deletion, substitution, or addition of one or several amino acids, the amino acid sequence including an amino acid sequence of SEQ ID NO: 4 and an and amino acid sequence of SEQ ID NO: 5, and may catalyze the first reaction.

[3-8]

A composition according to any one of the items [3] and [3-1] to [3-7] above, in which the pyruvate orthophosphate dikinase is any of the enzymes which have the following physicochemical properties <<1>> to <<5>> and may catalyze the first reaction.

<<1>> Optimum pH

In the range from pH 7 to 7.5;

<<2>> pH Stability

The activity is maintained to 80% or more after a treatment at 50° C. for 20 minutes in the range of pH 4.5 to 11;

<<3>> Thermostability

The activity is maintained to 90% or more after a heat treatment at 80° C. for 1 hour and is maintained to 70% or more after storage at 4° C. for at least 27 days;

<<4>> Coenzyme Specificity

The enzyme acts as an coenzyme specifically with AMP in the case where PEP and pyrophosphate are used as substrates in the presence of magnesium ions and does not react with ADP, IMP, CMP, GMP, TMP, or UMP;

<<5>> Substrate Specificity

Pyrophosphate is a specific substrate.

[3-9]

A composition according to any one of the items [3] and [3-1] to [3-8] above, in which the pyruvate orthophosphate dikinase further has any of the following physicochemical properties <<6>> and <<7>>.

<<6>> Frozen Storage Stability

The activity is maintained to 90% or more after storage at −20° C. for 2 weeks;

<<7>> Refrigerated Storage Stability

The activity is maintained to 80% or more after storage at 4° C. for 27 days;

[3-10]

A composition according to any one of the items [3] and [3-1] to [3-9] above, in which the pyruvate orthophosphate dikinase is derived from the genus *Thermotoga*.

[3-11]

A composition according to any one of the items [3] and [3-1] to [3-10] above, in which the pyruvate orthophosphate dikinase is derived from *Thermotoga maritima*.

[3-12]

A composition according to any one of the items [3], [3-1] to [3-6], and [3-8] to [3-11] above, in which the pyruvate orthophosphate dikinase is derived from the *Thermotoga maritima* DSM 3109 strain.

[3-13]

A composition according to any one of the items [3] and [3-1] to [3-12] above, in which the base sequence encoding the pyruvate orthophosphate dikinase is a base sequence as set forth in SEQ ID NO: 2 or SEQ ID NO: 3.

[3-14]

A composition according to any one of the items [3] and [3-1] to [3-13] above, wherein the nicotinamide-nucleotide adenylyltransferase is any of the following enzymes [1] and [2]:

[1] an enzyme which has an amino acid sequence of SEQ ID NO: 6 and may catalyze the second reaction; and

[2] an enzyme which has an amino acid sequence of SEQ ID NO: 6 with deletion, substitution, or addition of one or several amino acids and may catalyze the second reaction.

[3-15]

A composition according to any one of the items [3], [3-1] to [3-12], and [3-14] above, in which the nicotinamide-nucleotide adenylyltransferase is an enzyme which has an amino acid sequence of SEQ ID NO: 6 with one or more amino acid substitutions selected from the following <a> to <e> and may catalyze the second reaction.

<a> V132I
<b> D269V
<c> N64Y
<d> A65S
<e> A103S

[3-16]

A composition according to any one of the items [3] and [3-1] to [3-15] above, in which the base sequence encoding the nicotinamide-nucleotide adenylyltransferase is a base sequence as set forth in SEQ ID NO: 7.

[3-17]

A composition according to any one of the items [3] and [3-1] to [3-16] above, in which the nicotinamide-nucleotide adenylyltransferase is derived from an eukaryotic organism.

[3-18]

A composition according to any one of the items [3] and [3-1] to [3-17] above, in which the nicotinamide-nucleotide adenylyltransferase is derived from a yeast.

[3-19]

A composition according to any one of the items [3] and [3-1] to [3-18] above, in which the nicotinamide-nucleotide adenylyltransferase is derived from the genus *Saccharomyces*.

[3-20]

A composition according to any one of the items [3] and [3-1] to [3-19] above, in which the nicotinamide-nucleotide adenylyltransferase is derived from *Saccharomyces cerevisiae*.

[3-21]

A composition according to any one of the items [3] and [3-1] to [3-20] above, in which the third reaction is a reaction that is catalyzed with an enzyme capable of reducing NADs into NADHs.

[3-22]

A composition according to any one of the items [3] and [3-1] to [3-21] above, in which the third reaction is a reaction that is catalyzed with 12α-hydroxysteroid dehydrogenase.

[3-23]

A composition according to any one of the items [3] and [3-1] to [3-22] above, in which the oxidized NADH substance in the fourth reaction is DI.

[3-24]

A composition according to any one of the items [3] and [3-1] to [3-23] above, further including the following reagent (C).

(C) A Calibration Reagent Containing at Least A Known Amount of Pyrophosphate.

[4]

A composition according to any one of the items [3] and [3-1] to [3-24] above, which is used for detecting or quantifying a nucleic acid.

[5]

A method of detecting or quantifying a nucleic acid including performing the method according to the item [2] or [2-1] above using the composition according to the item [4] above.

[6]

Nicotinamide-nucleotide adenylyltransferase which has a substrate specificity ratio for dNTPs and ATP (substrate specificity for dNTPs/substrate specificity for ATP) of 5% or less.

According to the present invention, there can be provided a method of measuring pyrophosphate selectively and easily at high sensitivity. If the method of measuring pyrophosphate is used, there can also be provided a method of detecting or quantifying a nucleic acid in a nucleic acid amplification step.

BRIEF DESCRIPTION OF THE DRAWINGS

In the accompanying drawings:

FIG. 2 shows a chart illustrating the results of separation of ATP, ADP, AMP, and adenosine by HPLC.

FIG. 3 shows a chart illustrating the results of separation of the reaction solution before the reaction by HPLC.

FIG. 4 shows a chart illustrating the results of separation of the reaction solution after the reaction by HPLC.

FIG. 5 shows a graph illustrating the stability of the PPDK during refrigerated storage (4° C.).

FIG. 6 shows a graph illustrating the thermostability of the PPDK.

FIG. 7 shows a graph illustrating the thermostability of the PPDK.

FIG. 8 shows a graph illustrating the optimum pH of the PPDK.

FIG. 9 shows a graph illustrating the pH stability of the PPDK.

FIG. 10 shows a graph illustrating the results of measurement of the concentration of pyrophosphate.

FIG. 11 shows a graph illustrating the results of measurement of the concentration of the pyrophosphate in the presence and absence of dNTPs.

FIG. 12 shows a graph illustrating the results of measurement of the concentration of the pyrophosphate during a nucleic acid amplification reaction by PCR.

FIG. 13 shows a graph illustrating the results of measurement of the concentration of the pyrophosphate during a nucleic acid amplification reaction by PCR.

FIG. 15 shows a graph illustrating the results of nucleic acid amplification detected by real-time PCR using Smart cycler (registered trademark) II System (TAKARA BIO INC.) (●) and the results of nucleic acid amplification detected using the composition for measurement of the concentration of the pyrophosphate and the method of measuring the concentration of the pyrophosphate of the present invention (○).

FIG. 16 shows one example of a cycling reaction between the step including the first reaction and the step including the second reaction.

FIG. 17 shows one example of a cycling reaction between the step including the third reaction and the step including the fourth reaction.

FIG. 18 shows a graph illustrating the results of measurement of the concentration of the pyrophosphate in the presence and absence of dNTPs. [Sequence Listing]

DETAILED DESCRIPTION OF THE PREFERRED EMBODIMENTS

Figure 1:
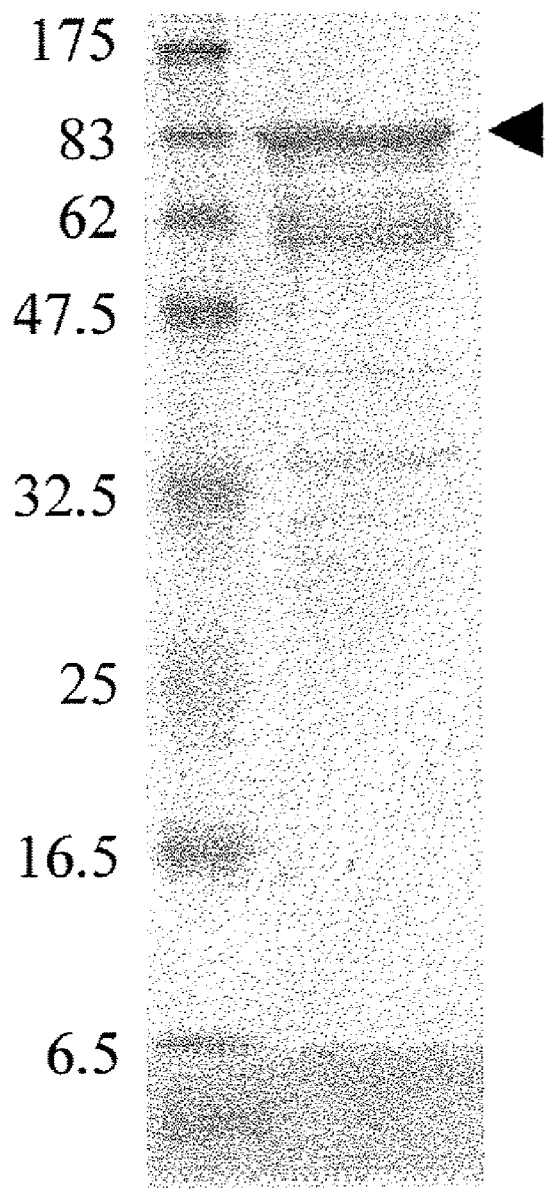
FIG. 1 shows an SDS-PAGE of a solution of crudely purified PPDK expressed by pUC118/TM0272. The arrow shows the PPDK.

One aspect of the present invention is a method of selectively measuring pyrophosphate in a sample including the following steps (1) to (4):

(1) a step including a first reaction for producing ATP by bringing the pyrophosphate which may be present in the sample into contact with pyruvate orthophosphate dikinase;

(2) a step including a second reaction for producing the pyrophosphate and NADs by bringing the ATP produced by the first reaction into contact with nicotinamide-nucleotide adenylyltransferase;

(3) a step including a third reaction for reducing the NADs produced by the second reaction into NADHs; and (4) a step of detecting the NADHs produced by the third reaction.

The method of selectively measuring pyrophosphate of the present invention may further includes (5) a step including a fourth reaction for converting the NADHs produced by the third reaction into a reduced nitroblue tetrazolium salt and NADs in the presence of a nitroblue tetrazolium salt; and the present invention included a method of measuring selective pyrophosphate for detecting the reduced NTBs (herein, sometimes referred to as "NTBH2") produced by the fourth reaction.

Pyrophosphate (H4P2O7) is sometimes referred to as "μ-oxo-hexaoxodiphosphate" or "diphosphate". The pyrophosphate in the present invention includes known pyrophosphate and is not limited by the source, dosage form, additive, product name, or the like.

Examples of the pyrophosphate in the present invention include pyrophosphate produced during amplification of nucleic acids such as DNA and RNA through various nucleic acid amplification methods and pyrophosphate synthesized as a product of a nucleic acid synthesis reaction using a DNA or RNA polymerase in cells, for example. That is, the pyrophosphate of the present invention includes: pyrophosphate obtained as a product of a nucleic acid amplification method such as polymerase chain reaction (PCR), nucleic acid sequence based amplification (NASBA), loop-mediated isothermal amplification (LAMP), isothermal and chimeric primer-initiated amplification of nucleic acids (ICAN), transcription mediated amplification (TMA), or transcription reversetranscription concerted amplification (TRC); pyrophosphate contained in synovial fluid which is an index of crystal deposition arthritis; and the like. That is, if the pyrophosphate is measured, it is possible to detect or quantify a nucleic acid by various nucleic acid amplification methods, to detect nucleic acid amplification, or to detect crystal deposition arthritis etc.

Examples of the sample of the present invention include, but not limited to: a test solution during a nucleic acid amplification reaction by the above-mentioned nucleic acid amplification method; biological samples or samples for research such as synovial fluid, whole blood, plasma, serum, hemocyte, spinal fluid, lymph, and urine; and extracts thereof. Examples of the other samples further include seawater, natural water, fruit juice, drink, and waste fluid. In addition, the sample of the present invention may or may not contain pyrophosphate and is preferably a sample which may contain the pyrophosphate. In general, a test solution during or after the nucleic acid amplification reaction by the above-mentioned nucleic acid amplification method may contain the pyrophosphate, and the sample which may contain the pyrophosphate further includes: a biological substance which is (has been) brought into direct or indirect contact with DNA or RNA polymerase; and a substance which is (has been) brought into direct or indirect contact with an organism such as a microorganism. Those samples may be subjected to a pretreatment for removing impurities which may affect measurement.

The dNTPs of the present invention is one kind or two or more kinds selected from the group consisting of dATP, dGTP, dCTP, and dTTP, and may be, for example, a mixture of the dATP, dGTP, dCTP, and dTTP. The mixing ratio of the dATP, dGTP, dCTP, and dTTP is arbitrarily set, and the mixture may be equimolar.

The dNTPs may be present or absent in a sample or in one or two or more steps selected from the steps including the first to fourth reactions. If the dNTPs is present, each concentration of the dNTPs is arbitrary and is preferably 4 mM or less, more preferably 1 mM or less, and most preferably 0.4 mM or less.

The measurement method of the present invention includes a method of detecting or quantifying a nucleic acid based on the production or production level of the pyrophosphate as an index and further includes a detection or qualification method of selectively measuring the pyrophosphate produced by the above-mentioned nucleic acid amplification method. The method further includes a detection or quantification method of selectively measuring pyrophosphate produced by an in vivo or in vitro natural nucleic acid amplification reaction.

The first reaction of the present invention is a reaction for producing ATP by bringing the pyrophosphate which may be present in the sample into contact with pyruvate orthophosphate dikinase.

The enzyme to be used in the first reaction of the present invention may be pyruvate orthophosphate dikinase (herein, sometimes referred to as "PPDK"), which may be referred to as "pyruvate orthophosphate dikinase", "EC 2.7.9.1", or the like. The enzymatic action of the PPDK of the present invention in the presence of a metal ion such as a magnesium ion is shown in [Formula 1]. For example, in the case where ATP, pyruvic acid, and phosphate are used as substrates, the reaction proceeds to the left in [Formula 1]. On the other hand, for example, in the case where AMP, PEP, and pyrophosphate are used as substrates, the reaction proceeds to the right in [Formula 1]. The first reaction of the present invention is intended to produce the ATP using the AMP as a substrate, and therefore, the reaction formula of the first reaction proceeds to the right in [Formula 1].

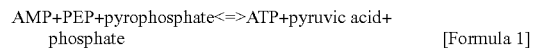

AMP+PEP+pyrophosphate<=>ATP+pyruvic acid+ phosphate  [Formula 1]

The PPDK of the present invention is not limited by the source, enzyme name, EC number, or production method as long as the enzyme has the ability to catalyze the reaction of [Formula 1] above. Such PPDK preferably has any of the above-mentioned physicochemical properties <<1>> to <<5>> and the PPDK properties described herein. That is, the enzyme preferably has the ability to catalyze the reaction of [Formula 1], irrespective of other properties, and also preferably has one or two or more arbitrary properties selected from the above-mentioned physicochemical properties <<1>> to <<5>> and the PPDK properties described herein. Moreover, such PPDK also preferably has the above-mentioned properties <<6>> and <<7>>. The PPDK of the present invention may also include physicochemical properties or physical properties other than the properties of the PPDK described herein.

As such PPDK, there are exemplified known PPDKs such as maize leaf-derived PPDK (Biochemistry 12, 2862-2867 (1973)), sugarcane leaf-derived PPDK (The Biochemical Journal 114, 117-125 (1969)), Asteraceae plant-derived PPDK (Plant and Cell Physiology 31, 29 5-297 (1990)), *Propionibacterium shermanii*-derived PPDK (Biochemistry 10, 721-729 (1971)), *Bacteroides symbiosus*-derived PPDK (Methods in Enzymology 42, 199-212 (1975)), *Acetobacter xylinum*-derived PPDK (Journal of Bacteriology 104, 211-218 (1970)), and genus *Microbispora*-derived PPDK (Japanese Patent Application Laid-Open No. Hei 08-168375 A), or isoenzymes thereof.

Although the PPDK of the present invention may be derived from natural organisms other than the above-mentioned sources, if the PPDK is derived from a microorganism, the PPDK is derived from, for example, a microorganism belonging to the genus *Thermotoga*, preferably *Thermotoga maritima*, and most preferably *Thermotoga maritima* DSM 3109 strain. The strain may be purchased from the strain bank mentioned below, or a strain equivalent to the strain, which may be purchased from another strain bank, or an equivalent strain isolated from a known method may be used in the measurement method of the present invention after the equivalent strain is analyzed to confirm whether the strain can produce an enzyme having the properties of the PPDK of the present invention.

The amount of the PPDK to be used in the first reaction of the present invention is not particularly limited as long as the measurement method of pyrophosphate of the present invention can be performed. The amount may be determined so that preferable results can be obtained depending on the amount of the pyrophosphate in a sample, device to be used, purity or kind of the PPDK, and/or economic circumstances. In the case where AMP, a metal ion, or pyruvic acid is further used in the first reaction of the present invention, the kinds and amounts thereof may be determined in the same way as above.

For example, the lower limit of the amount of the PPDK to be used in the first reaction of the present invention is 0.01 U/ml or more, preferably 0.1 U/ml or more, and more preferably 0.5 U/ml or more, while the upper limit is not particularly limited but is 100 U/ml or less, preferably 50 U/ml or less, and more preferably 20 U/ml or less.

The first reaction of the present invention is preferably performed in the presence of at least the AMP. The lower limit of the amount of the AMP used under the above-mentioned conditions is 0.05 mM or more, preferably 0.1 mM or more, and more preferably 0.5 mM or more, while the upper limited is not particularly limited but is preferably 50 mM or less, more preferably 20 mM or less, and particularly preferably 5 mM or less.

The first reaction of the present invention is preferably performed in the presence of at least a high-energy phosphate compound such as PEP. The lower limit of the amount of the PEP used under the above-mentioned conditions is 0.05 mM or more, preferably 0.1 mM or more, and more preferably 0.5 mM or more, while the upper limited is not particularly limited but is preferably 50 mM or less, more preferably 20 mM or less, and particularly preferably 5 mM or less.

The first reaction of the present invention is preferably performed in the presence of at least a metal ion. The metal ion may be one or more metal ions selected from a magnesium ion, a cobalt ion, and a nickel ion, and of those, the magnesium ion is particularly preferable. For example, if the magnesium ion is used as a metal ion under the above-mentioned conditions, the lower limit of the amount of the magnesium ion is 0.2 equivalent, compared to the concentration of AMP, or more, preferably 0.5 equivalent or more, and more preferably 0.8 equivalent or more, while the upper limit is 5 equivalents or less, preferably 3 equivalents or less, and more preferably 2 equivalents or less. The most preferable concentration is 1 equivalent of a phosphate donor.

The amino acid sequence of the PPDK of the present invention is not limited as long as the enzyme has the ability to catalyze the reaction of [Formula 1] above. For example, in the case where the PPDK has the amino acid sequence of SEQ ID NO: 1, the sequence may be the amino acid sequence of SEQ ID NO: 1 with deletion, substitution, or addition of one or multiple amino acids. The amino acid sequence preferably includes the amino acid sequence of SEQ ID NO: 4 and the amino acid sequence of SEQ ID NO: 5. In addition, the amino acid sequence more preferably includes the amino acid sequence SMPGMMDT (SEQ ID NO: 13) or the amino acid sequence LNLGLND (SEQ ID NO: 14). The typical amino acid sequence of the PPDK of the present invention is the amino acid sequence of SEQ ID NO: 1.

Examples of the deletion, substitution, or addition of amino acids in the amino acid sequence of SEQ ID NO: 1 include addition of an amino acid sequence of a functional enzyme such as thioredoxin or another amino acid sequence to the N-terminal and/or the C-terminal side of the PPDK. It is also preferable to produce a fused protein. The following case may be exemplified. An amino acid sequence which is used for purification or confirmation depending on the addition site (so-called "tag") may be fused, and in some cases, even if the tag sequence is eliminated, a part or whole of the sequence may remain. The tag may be about 20 signal peptides to be used for transportation of the PPDK to the outside of the cell or periplasm or 5 to 10 His residues to be used for effective purification, and the amino acid residues may be added in series. In addition, addition may be performed so that several protease-recognizing amino acid sequences may be arranged between such amino acid sequences or the like.

As with the above-mentioned examples of addition, deletion or substitution may be performed. For example, in the case where there is a domain including several amino acids irrelevant to the essential functions of the PPDK of the present invention, or in the case where there is a gap including plural amino acids in the amino acid sequence of SEQ ID NO: 1, the deletions thereof may be combined. Meanwhile, deletion, substitution, and addition may be appropriately combined. Further, in the amino acid sequence of SEQ ID NO: 1, the N-terminal and C-terminal sides may include amino acid residues or polypeptide residues, that is, may have an addition thereof, and examples of the added amino acid residues include a signal peptide, TEE sequence, S-tag, and His-tag. To delete some amino acids from the amino acid sequence of SEQ ID NO: 1, for example, the amino acids may be eliminated consecutively from the N-terminal or C-terminal side. The PPDK of the present invention includes an enzyme having the amino acid sequence of SEQ ID NO: 1, which has been modified after translation by deleting Met at the N-terminal or by modifying the N-terminal with an acyl or alkyl group. In addition, the PPDK may be chemically modified with succinic anhydride, PEG, or the like by a known method to change properties such as the optimum pH and stability into properties that can be easily used. In such a case, the molecular weight of the PPDK may vary. For example, if the His-tag is added to the N-terminal using the pET vector mentioned below, the molecular weight increases by about 1,000. The secondary and tertiary structures of the amino acid sequence of the PPDK of the present invention are not particularly limited.

The base sequence of the PPDK of the present invention is not particularly limited as long as the base sequence encodes the PPDK of the present invention. For example, in the case of a base sequence encoding the amino acid sequence of SEQ ID NO: 1, the sequence may be a base sequence encoding an amino acid sequence substantially equal to the sequence of SEQ ID NO: 1. For example, the sequence may be a base sequence which encodes an amino acid sequence obtained by mutating part of amino acids which is included in the amino acid sequence of SEQ ID NO: 1 and is not involved in the catalysis of the first reaction, for example, an equivalent to the amino acid sequence of SEQ ID NO: 1 with deletion, substitution, or addition of one or multiple amino acids. Mutation is particularly preferably performed so that the base sequences encoding the sequences of SEQ ID NOs: 4 and 5 and the above-mentioned amino acid sequences be included. Examples of the base sequence encoding the amino acid sequence of SEQ ID NO: 1 include the base sequence of SEQ ID NO: 2 and a base sequence obtained by modifying the base sequence of SEQ ID NO: 2 so as to suit the frequency of use of codons in an appropriate host. Examples of the sequence include the base sequence of SEQ ID NO: 3 obtained by changing the base sequence of SEQ ID NO: 2 so as to suit the frequency of use of codons in *Escherichia coli*.

The base sequence encoding the PPDK may be prepared by using a conventional known genetic engineering technique, and examples of the technique include various methods such as site-specific mutation and substitution of artificially mutated bases for a specific base fragment of a target gene.

The second reaction of the present invention is a reaction for producing pyrophosphate and NADs by bringing the ATP produced by the first reaction into contact with nicotinamide-nucleotide adenylyltransferase.

The enzyme to be used in the second reaction of the present invention may be nicotinamide-nucleotide adenylyltransferase (herein, sometimes referred to as "NMNATase"), which may be referred to as "NAD (+) pyrophosphorylase", "EC 2.7.7.1", or the like. The enzymatic action of the NMNATase of the present invention in the presence of a metal ion such as a magnesium ion is shown in [Formula 2]. For example, in the case where ATP and NMN are used as substrates, the reaction proceeds to the right in [Formula 2]. On the other hand, for example, in the case where NAD and pyrophosphate are used as substrates, the reaction proceeds to the left in [Formula 2]. The second reaction formula of the present invention proceeds to the right in [Formula 2].

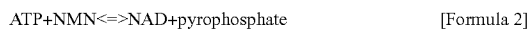

ATP+NMN<=>NAD+pyrophosphate [Formula 2]

The NMNATase of the present invention is not limited by the source, enzyme name, EC number, or production method, irrespective of other properties, as long as the enzyme has the ability to catalyze the reaction of [Formula 2] above. Such NMNATase also preferably has one or two or more properties selected from any of the NMNATase properties described herein, although the NMNATase may or may not have other properties. The NMNATase of the present invention may also have physicochemical properties and physical properties other than the NMNATase properties described herein. Examples of such NMNATase include NMNATase derived from an archaebacterium, *Sulfolobus solfataricus* (J. Bacteriol, vol. 179, pp. 7718, 1997), NMNATase derived from an archaebacterium, *Methanococcus jannaschii* (J. Bacteriol, vol. 179, pp. 7718, 1997), and known NMNATase derived from a human or the like (Biochem. J, vol. 377, pp. 317, 2004). If NMNATase derived from a mammal including a human or yeast includes known isozymes, such isozymes may be employed.

The NMNATase of the present invention may, for example, be derived from a natural organism but is preferably derived from a eukaryotic organism. In the case where the NMNATase is derived from a microorganism, the microorganism is preferably yeast, more preferably a microorganism belonging to the genus *Saccharomyces*, most preferably *Saccharomyces cerevisiae*. Such strains can be obtained in the same way as in the case of the PPDK above.

The NMNATase of the present invention may be derived from *Saccharomyces cerevisiae* 1-2, 3-2, and 6-2 strains obtained by screening performed in accordance with a conventional method including the method mentioned below.

In the case where crossover takes place between the substrate specificity of the NMNATase of the present invention for ATP and the specificity of the NMNATase of the present invention for dNTPs, that is, in the case where the ATP and dNTPs can act as substrates of the NMNATase, a reaction for eliminating the dNTPs may be performed at the same time as any one of the first to fourth reactions of the present invention or separately from such reactions. The crossover between the substrate specificity for ATP and the substrate specificity for dNTPs is preferably small. For example, in the NMNATase of the present invention, the dNTPs/ATP value (ratio of substrate specificity for dNTPs/substrate specificity for ATP) is preferably 70% or less, more preferably 30% or less, particularly preferably 10% or less, and most preferably 5% or less.

The amino acid sequence of the NMNATase of the present invention is the same as that of the PPDK above. The typical amino acid sequence of the NMNATase of the present invention is the sequence of SEQ ID NO: 6.

The amino acid sequence of the NMNATase derived from *Saccharomyces cerevisiae* 6-2 strain, which is the amino acid sequence of SEQ ID NO: 6, is the same as that of yNMNAT-2, which has been reported by Emanuelli et al. (Protein Expression and Purification, 2003, vol. 27, pp. 357). The amino acid sequence of the NMNATase derived from *Saccharomyces cerevisiae* 1-2 strain of the present invention has the amino acid sequence of SEQ ID NO: 6 with a substitution of I for V at position 132 (herein, such substitution is sometimes referred to as "V132I", which represents, in the stated order, the amino acid before substitution, substitution position, and amino acid after substitution) and with a substitution of D269V. Meanwhile, the amino acid sequence of the NMNATase derived from *Saccharomyces cerevisiae* 3-2 of the present invention has the amino acid sequence of SEQ ID NO: 6 with substitutions of N64Y, A65S, and A103S. Therefore, examples of the amino acid substitution in the amino acid sequence of SEQ ID NO: 6 include V132I, D269V, N64Y, A65S, and A103S.

The NMNATase having the amino acid sequence of SEQ ID NO: 6 above may be produced according to the method of Emanuelli et al. (Protein Expression and Purification, 2003, vol. 27, pp. 357), while the NMNATase derived from *Saccharomyces cerevisiae* 1-2 and 3-2 strains of the present invention may be produced by performing amino acid substitutions for V at position 132, D at position 269, A at position 103, N at position 64, and A at position 65 in the amino acid sequence of SEQ ID NO: 6 by a conventional method such as site-specific amino acid substitution by PCR or using a commercially available kit.

The base sequence of the NMNATase of the present invention is the same as that in the case of the PPDK above.

Examples of the base sequence of the NMNATase of the present invention include the sequence of SEQ ID NO: 7.

The amount of the NMNATase to be used in the second reaction of the present invention is the same as that in the case of the PPDK above. In the case where NMNs or a metal ion is further used in the second reaction of the present invention, the kind and amount thereof are the same.

For example, the lower limit of the amount of the NMNATase to be used in the second reaction of the present invention is 0.1 U/ml or more, preferably 0.3 U/ml or more, more preferably 0.5 U/ml or more, while the upper limit is not particularly limited but is 20 U/ml or less, preferably 10 U/ml or less, and more preferably 5 U/ml or less.

The second reaction of the present invention is preferably performed in the presence of at least NMNs such as β-nicotinamide mononucleotide and nicotinic acid mononucleotide, and the amounts of the NMNs used under the above-mentioned conditions are as follows. For example, the lower limit of the amount of NMN is 0.05 mM or more, preferably 0.1 mM or more, and more preferably 0.5 mM or more, while the upper limit is not particularly limited but is preferably 50 mM or less, more preferably 20 mM or less, and particularly preferably 5 mM or less.

The second reaction of the present invention is preferably performed in the presence of at least a metal ion, and a magnesium ion is particularly preferable. The amount of the metal ion used under the above-mentioned conditions are as follows. For example, the lower limit of the amount of the magnesium ion is 0.05 mM or more, preferably 0.1 mM or more, and more preferably 0.5 mM or more, while the upper limit is not particularly limited but is preferably 50 mM or less, more preferably 20 mM or less, and particularly preferably 5 mM or less.

In the second reaction of the present invention, for example, if ATP produced by the first reaction is brought into contact with the NMNATase in the presence of magnesium ion and the NMN, pyrophosphate and NAD are produced. Meanwhile, for example, if the ATP produced by the first reaction is brought into contact with the NMNATase in the presence of the magnesium ion and nicotinic acid mononucleotide, pyrophosphate and deamide-NAD are produced.

The third reaction of the present invention is a reaction for reducing the NADs produced by the second reaction into NADHs.

The NADs in the third reaction of the present invention include either or both of NAD and deamide-NAD (NAAD), and NAD is particularly preferable.

The method of reducing the NADs into the NADHs in the third reaction of the present invention is not particularly limited as long as the method is a known one. In the method, the NADs are reduced into the NADHs using an NAD-reduced substance of the present invention. The reduction method may be based on an enzymatic or nonenzymatic reaction, and in the case where the NADs are enzymatically reduced into the NADHs, an enzyme which requires NADs as coenzymes, for example, may be used. Examples of the enzyme include dehydrogenase.

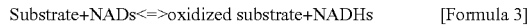

Substrate+NADs<=>oxidized substrate+NADHs    [Formula 3]

In the case where the third reaction of the present invention is enzymatically performed, the dehydrogenase to be used is not limited by the enzyme name, EC number, source, amino acid sequence, base sequence, or production method as long as the enzyme has the ability to catalyze the reaction of [Formula 3] above. As the dehydrogenase, preferred is, for example, hydroxysteroid dehydrogenase (may be referred to as "HSD" in the present specification), more preferred is 3α-HSD, 3β-HSD, 17β-HSD, 11β-HSD, 16α-HSD, 20α-HSD, 7α-HSD, 12α-HSD, 7β-HSD, or 12β-HSD, and particularly preferred are 3α-HSD and 12α-HSD.

For example, in the case where the dehydrogenase is used in the third reaction of the present invention, the amount of the dehydrogenase is the same as that in the case of the PPDK above. The kind and amount of a substrate, coenzyme, or the like necessary for the reaction of the dehydrogenase to be used further in the third reaction of the present invention are the same as those in the case of the PPDK.

For example, in the case where the 12α-HSD is used in the third reaction of the present invention, the lower limit of the amount of the 12α-HSD used is 0.1 U/ml or more, preferably 0.5 U/ml or more, and more preferably 1 U/ml or more, while the upper limit is not particularly limited but is 50 U/ml or less, preferably 20 U/ml or less, and more preferably 10 U/ml.

For example, in the case where the third reaction of the present invention is performed using the 12α-HSD, the reaction is preferably performed in the presence of at least a substrate of the 12α-HSD. Examples of the substrate include 3α-, 7α-, or 12α-hydroxy bile acid, cholic acid, and deoxycholic acid. In the case where, for example, the cholic acid is used as the substrate of the 12α-HSD under the above-mentioned conditions, the lower limit of the amount of the cholic acid is 0.1 mM or more, preferably 0.2 mM or more, and more preferably 0.5 mM or more, while the upper limit is not particularly limited but is preferably 50 mM or less, more preferably 20 mM or less, and particularly preferably 10 mM or less. If the substrate inhibits the reactions of the present invention, it is effective to adjust the concentration of the substrate or to change the substrate.

As an example in the case where the 12α-HSD is used, the product is 3α-, 7α-dihydroxy-12-oxo-5-β-cholanate when the cholic acid (3α-, 7α-, 12α-trihydroxy-5β-cholanic acid) is used as a substrate.

The fourth reaction of the present invention is a reaction for converting the NADHs produced by the third reaction into a reduced NTBs and NADs in the presence of NTBs.

The NTBs used in the fourth reaction of the present invention include heterocyclic organic compounds which are widely used as detection reagents for various enzymes and redox coloring reagents, such as formazans e.g., 1,3,5-triphenylformazan, 1,5-bis(4-methoxyphenyl)-3-phenylformazan, and 1,5-diphenyl-3-(2-thienyl)formazan and tetrazolium salts e.g., 2,3,5-triphenyltetrazolium, 2,3,5-tris(p-tolyl)tetrazolium, and 2,3-bis(3-chlorophenyl)-5-phenyltetrazolium. Those NTBs and reduced NTBs may be insoluble, poorly-soluble, or soluble in water.

The NADHs in the fourth reaction of the present invention is the same as those in the third reaction of the present invention.

The method of oxidizing the NADHs into NADs in the presence of NTBs in the fourth reaction of the present invention is not particularly limited as long as the method is a known one. In the method, the NADHs are oxidized into the NADs using the Oxidized NADH substance of the present invention (NTBs are reduced into reduced NTBs). This method may be performed enzymatically or nonenzymatically. The fourth reaction of the present invention is shown in [Formula 4].

NTBs+NADHs<=>reduced NTBs+NADs    [Formula 4]

In the case where the fourth reaction of the present invention is enzymatically performed, the enzyme to be used is not limited by the enzyme name, EC number, source, amino acid sequence, base sequence, or production method as long as the enzyme has the ability to catalyze the reaction of [Formula 4] above. In the case where the NADHs are enzymically oxidized into the NADs in the presence of the NTBs, there can be used diaphoreses such as NAD(P)H dehydrogenase (quinone), NADPH dehydrogenase, and NADH dehydrogenase. Those enzymes may be expressed as EC 1.6.5.2, EC 1.6.99.1, and EC 1.6.99.3, respectively.

For example, in the case where DIs are used in the fourth reaction of the present invention, the amount of the DIs is the same as that in the case of the PPDK above. The kind and amount of a substrate, coenzyme, or the like necessary for the reaction of the DIs to be used further in the fourth reaction of the present invention are the same as those in the case of the PPDK.

For example, in the case where DI is used in the fourth reaction of the present invention, the lower limit of the amount of the DI used is 0.1 U/ml or more, preferably 0.5 U/ml or more, and more preferably 1 U/ml or more, while the upper limit is not particularly limited but is 50 U/ml or less, preferably 20 U/ml or less, and more preferably 10 U/ml.

For example, in the case where the DI is used in the fourth reaction of the present invention, the reaction is preferably performed in the presence of at least NTB (nitrotetrazolium blue (sometimes referred to as "nitroblue tetrazolium (NBT)")), for example. The amount of a substrate of the NTBs to be used under the above-mentioned conditions is not particularly limited as long as the substrate is present. The lower limit of the amount of the substrate is 0.001% or more, preferably 0.005% or more, and more preferably 0.01% or more, with just the presence of the substrate being enough, while the upper limit is not particularly limited but is preferably 1% or less, more preferably 0.5% or less, and particularly preferably 0.1% or less. In the case where the reduced NTBs have poor water solubility, the NTBs may be solubilized by a known method using, for example, the surfactant as described below.

The method of selectively measuring pyrophosphate according to the present invention includes a method of selectively measuring pyrophosphate in the case where a sample and one or two or more steps selected from the steps including the first to fourth reactions contain, together with the pyrophosphate, a substance (coexisting substance) which may cause a positive or negative error in a measured value of the pyrophosphate. That is, the method of selectively measuring pyrophosphate according to the present invention includes a method selectively measuring pyrophosphate, which is not or hardly affected by the coexisting substance. Examples of the coexisting substance include dNTPs.

The measurement method involving detecting NADHs of the present invention includes a measurement method involving detecting NADHs by a qualitative reaction. The method is preferably a measurement method involving detecting a change in the amount of the NADHs produced by the third reaction, more preferably a measurement method for quantification involving detecting a change in the amount of the NADHs produced by the third reaction. The same holds for the measurement method involving detecting the reduced NTBs produced by the fourth reaction.

The measurement method for quantification is performed as follows, for example. Pyrophosphate in a sample is quantified by: treating the sample which may contain the pyrophosphate by the steps including the first to third reactions; detecting the NADHs produced by the third reaction; and comparing the resultant value with the concentration of NADHs, which has been determined in the same manner as above by a reaction of a sample containing a known concentration of pyrophosphate. NADHs may be detected as reduced the NTBs produced by the fourth reaction. In the case where a reagent blank is subtracted, a value obtained by treating a sample containing no pyrophosphate (such as distilled water) instead of the sample which may contain pyrophosphate in the same way as above may be subtracted from the resultant value.

NADHs may be detected by a known method. That is, the NADHs may be detected directly or may be subjected to a further reaction and then detected indirectly. The indirect detection method may include the fourth reaction of the present invention, and the method can detect the NADHs easily by visual observation if the NADHs are detected as reduced NTBs obtained by a reaction of the NADHs with NTBs. Examples of the method of detecting the NADHs further includes: a method of detecting changes in absorption spectrum or absorbance intensity of the NADHs or reduced NTBs caused by changes in the objects to be measured using a device by an optical method; and a method of detecting a change in absorption spectrum or absorbance intensity at a specific wavelength caused by the NADHs or reduced NTBs. The method further includes a method of detecting changes in fluorescence of the NADHs. In the case where a potential difference due to oxidation-reduction is measured, electrodes may be used.

In the assay of the present invention, a cycling reaction may be employed between the step including the first reaction and the step including the second reaction. The "cycling reaction" means that the pyrophosphate produced by the step including the second reaction is allowed to react again in the step including the first reaction. FIG. 16 shows one example of the cycling reaction between the step including the first reaction and the step including the second reaction. In the cycling reaction, NAD, pyruvate, and phosphate (Pi) are amplified. Therefore, if the cycling reaction is employed in the measurement method of the present invention, the measurement sensitivity of the measurement method of the present invention will be improved because the NAD is amplified.

Meanwhile, in the measurement method of the present invention, a cycling reaction may be employed between the step including the third reaction and the step including the fourth reaction, where the NADs produced by the step including the fourth reaction is allowed to react again in the step including the third reaction. In the cycling reaction, reduced NTBs are amplified. If the cycling reaction is employed in the measurement method of the present invention, the measurement sensitivity of the measurement method of the present invention will be improved. FIG. 17 shows one example of a cycling reaction between the step including the third reaction and the step including the fourth reaction. In the cycling reaction, $3\alpha$-, $7\alpha$-dihydroxy-12-oxo-5-$\beta$-cholanate and reduced NTB (NTBH2) are amplified. Therefore, if the cycling reaction is employed in the measurement method of the present invention, the measurement sensitivity of the measurement method of the present invention will be improved because the reduced NTB is amplified.

Moreover, in the measurement method of the present invention, there may be employed a double cycling reaction, where the cycling reaction between the step including the first reaction and the step including the second reaction is performed simultaneously with the cycling reaction between the step including the third reaction and the step including the fourth reaction. That is, if the double cycling reaction, where the pyrophosphate produced by the step including the second reaction is allowed to react in the step including the first reaction to amplify NAD by the step including the second reaction, and the NAD produced by the step including the fourth reaction is allowed to react in the step including the third reaction to amplify reduced NTBs by the step including the fourth reaction, is employed in the measurement method of the present invention, the measurement sensitivity of the measurement method of the present invention will be improved.

The measurement method of the present invention may be performed in a liquid, gas, or solid phase, or a critical plane thereof, and the liquid phase is preferable. The liquid phase may include an aqueous phase, an organic solvent phase, and the like. In the case where the measurement method of the present invention is performed in the aqueous phase, examples of the aqueous phase include water, a solution, and an aqueous vehicle containing an appropriate organic solvent, and an appropriate pH buffer is preferably used. The kind of the pH buffer to be used is not particularly limited as long as the target pH can be maintained and measurement of pyrophosphate in a sample can be performed. Examples of the buffer include a Good's pH buffer, Tris/HCl buffer, potassium phosphate buffer, acetic acid/NaOH buffer, and citric acid/NaOH buffer. The pH value in the measurement method of the present invention is not particularly limited as long as measurement of pyrophosphate in a sample can be performed. The lower limit of the value is, for example, pH 5 or more, preferably pH 5.5 or more, and more preferably pH 6 or more, while the upper limit is, for example, pH 10 or less, preferably pH 9 or less, and more preferably pH 8.5 or less. The concentration of the pH buffer is not particularly limited as long as the target pH can be maintained and measurement of pyrophosphate can be performed The lower limit of the concentration is, for example, 3 mM or more, preferably 5 mM or more, and more preferably 10 mM or more, while the upper limit is, for example, 500 mM or less, preferably 200 mM or less, and more preferably 100 mM or less.

Preferable other examples of the liquid phase to be used in the measurement method of the present invention further include sol-gel. To prepare the sol-gel, for example, a polysaccharide such as agar may be used. In the case where the sol-gel is distinguished from an emulsion, the emulsion may be preferable. To prepare the emulsion, for example, an organic solvent or the like may be used, or an amphiphilic substance may be used to prepare a micelle. In each case, the same holds for the case where a pH buffer is used.

The steps including the first to third reactions in the measurement method of the present invention may be performed in different reaction tanks (phases) but are preferably performed in the same reaction tank (phase). In addition, the steps including the first to third reactions may be performed discontinuously but are preferably performed continuously. Meanwhile, the steps including the first to third reactions may be performed in the order of the step including the first reaction, the step including the second reaction, and the step including the third reaction, and two or more steps may be performed simultaneously or may be combined with a single step so that preferable results will be achieved depending on the purpose, sample, or used device. The same holds for the case where the measurement method of the present invention includes the steps including the fourth reaction.

The reaction time between the step including the first reaction and the step including the third reaction of the present invention is not particularly limited as long as the pyrophosphate in a sample can be measured. The lower limit of the time is 15 seconds or more, preferably 1 minute or more, and more preferably 3 minutes or more, while the upper limit is not particularly limited but is preferably 30 minutes or less, more preferably 15 minutes or less, and particularly preferably 10 minutes or less. The reaction times of the steps including the first to third reactions may be unequal. The same holds for the case where the measurement method of the present invention includes the step including the fourth reaction.

The temperature of the reaction for performing the measurement method of the present invention is not particularly limited as long as the target pH can be maintained and the pyrophosphate in a sample can be measured. In the case where an enzyme is used, the temperature is preferable in the range of the temperature suitable for exerting the activity of the enzyme. The lower limit of the temperature is 10° C. or more, preferably 20° C. or more, and more preferably 25° C. or more, while the upper limit is 70° C. or less, preferably 50° C. or less, and more preferably 40° C. or less. The temperatures of the steps including the first to third reactions may be unequal. The same holds for the case where the measurement method of the present invention includes the step including the fourth reaction.

The composition for selective measurement of pyrophosphate of the present invention contains at least the following components (1) to (7):
(1) a metal ion;
(2) AMP;
(3) PEP (phosphoenolpyruvate);
(4) PPDK (pyruvate orthophosphate dikinase);
(5) NMNs (β-nicotinamide mononucleotides);
(6) NMNATase (nicotinamide-nucleotide adenylyltransferase); and
(7) a reduced NAD substance (e.g., dehydrogenase).

The composition for selective measurement of pyrophosphate of the present invention may further contain the following components (8) and (9):
(8) an oxidized NADH substance; and
(9) NTBs.

The composition for selective measurement of pyrophosphate of the present invention preferably contains at least the following reagents (A) and (B):
(A) a first reagent containing at least the following components (1) to (4):
(1) a metal ion;
(2) AMP;
(3) PEP; and
(4) PPDK; and
(B) a second reagent containing at least the following components (5) to (7):
(5) NMNs;
(6) NMNATase; and
(7) a reduced NAD substance.

The composition (B) for selective measurement of pyrophosphate of the present invention may further contain the following components (8) and (9):
(8) an oxidized NADH substance; and
(9) NTBs.

The composition for selective measurement of pyrophosphate of the present invention above also preferably contains a pH buffer appropriately.

The composition for selective measurement of pyrophosphate of the present invention may further contain the following component (C).
(C) A calibration reagent containing at least a known amount of pyrophosphate.

The types and amounts of the metal ion, AMP, PEP, PPDK, NMNs, NMNATase, NAD-reduced substance, Oxidized NADH substance, and NTBs of the present invention in the composition for selective measurement of pyrophosphate of the present invention, that is, the amounts of the above-mentioned substances effective for adjusting the composition to a composition for measurement of pyrophosphate, conditions of the pH buffer, and the like are the same as those in the case of the above-mentioned measurement method of the present invention.

The composition for measurement of pyrophosphate and calibration reagent of the present invention may be provided as liquid products, frozen products of the liquid products, freeze-dried products of the liquid products, or dried products of the liquid products (obtained by heat-drying and/or air-drying and/or drying under reduced pressure or the like). Of those, the composition and calibration reagent are preferably the frozen products of the liquid products, more preferably the freeze-dried products of the liquid products, and most preferably the liquid products. In another aspect, the frozen products of the liquid products are preferable in some cases. In further another aspect, the freeze-dried products of the liquid products are preferable in some cases. The composition for measurement of pyrophosphate of the present invention may be provided as one reagent and is preferably provided as two or more separate reagents as described above. To improve the quality of the reagent, a salt such as NaCl or KCl, a surfactant such as TX-100 or Tween 20, and/or a preservative such as sodium azide or an antibiotic may be blended. Meanwhile, for example, in the case where the composition is used in a POC capillary or an enzyme sensor, the concentrations of the components are preferably higher than usual. For example, the composition is preferably immobilized, impregnated into paper or membrane, or prepared as a sol-gel composition before use. In the case where a salt is blended, the type and concentration of the salt are not limited, but the concentration is usually in the range of 5 to 200 mM. In the case where a surfactant is blended, the type and concentration of the surfactant are not limited, but the concentration is usually in the range of 0.001% to 2%. In the case where sodium azide or an antibiotic is blended, the type and concentration are not limited as long as the preservative effect can be achieved. For example, in the case of the sodium azide, the lower limit of the concentration is 0.005% or more, preferably 0.01% or more, and more preferably 0.03% or more, while the upper limit is 1% or less, preferably 0.5% or less, and more preferably 0.1% or less. For example, in the case of the antibiotic, the lower limit of the concentration is 5 µg/ml or more, preferably 10 µg/ml or more, and more preferably 30 µg/ml or more, while the upper limit is 100 µg/ml or less, preferably 75 µg/ml or less, and more preferably 60 µg/ml or less.

The calibration reagent of the present invention may be a reagent containing at least a known amount of pyrophosphate and is preferably a reagent containing a pH buffer, a preservative such as sodium azide or an antibiotic, or a stabilizer such as a sugar. In the case where the reagent contains the pH buffer, conditions such as the type or concentration are the same as those in the case of the above-mentioned measurement method of the present invention. In the case where the reagent contains the stabilizer or preservative, the conditions are the same as those in the case of the composition of the present invention.

The above-mentioned known amount is not particularly limited, but in the case of the pyrophosphate, for example, the lower limit of the amount is 0 µM or more, preferably 0.1 µM or more, and more preferably 0.5 µM or more, while the upper limit is not particularly limited but is 1 mM or less, preferably 100 µM or less, and more preferably 50 µM or less.

The method of producing the enzyme to be used in the first reaction of the present invention will be described.

The enzyme to be used in the first reaction of the present invention may be obtained by: screening a natural organism capable of producing the enzyme in nature by a known method; and separating the enzyme from the cells of the organism. The organism is not limited as long as the organism can produce an enzyme capable of catalyzing the reaction of [Formula 1]. Examples of the organism include microorganisms such as eubacteria, eukaryotic organisms, and archaebacteria. In the case where a microorganism is a screening target, the microorganism may be isolated from nature by a known method. The microorganism may be obtained from soil or water including the ultimate environment such as high-temperature, low-temperature, high-pressure, acidic, or alkali environment; air including falling bacteria or ice nuclei; the body of an organism; or the like. In particular, a microorganism isolated from a high-temperature environment is expected to produce a highly stable enzyme to be used in the first reaction. Alternatively, the microorganism may be purchased from a strain bank such as ATCC or DSM described below. An organism capable of producing the enzyme to be used in the first reaction can be selected by: subjecting isolated microorganisms to pure isolation in accordance with a known method such as a limiting dilution method or monocolony formation; subjecting the microorganisms to pure culture in a minimum medium, LB medium, broth medium, or the like; and confirming whether the enzymatic activity of [Formula 1] is detected or not in the cultures. To improve the efficiency of the screening, a microorganism may be obtained by enrichment culture. A person skilled in the art can easily detect the enzymatic activity of [Formula 1] by, for example, the enzymatic activity measurement method mentioned below.

The isolated bacterial strain may be identified in accordance with, for example, an experimental protocol (Kenichi Suzuki et al., Experimental technique for classification/identification of microorganisms—molecular genetic/molecular biological technique, Springer-Verlag Tokyo, Inc.) or using commercially available bacterial strain identification kits (for example, bioMerieux Japan Ltd.). Alternatively, the strain may be identified by Japan Food Research Laboratories (52-1 Motoyoyogi-cho, Shibuya-ku, Tokyo) or the like.

The thus-obtained natural microorganism capable of producing the enzyme to be used in the first reaction of the present invention may be modified into a mutant by a further treatment with an agent such as NTG, ultraviolet ray, and/or radial ray. The mutant can improve productivity of the enzyme to be used in the first reaction and can produce a mutant of the enzyme to be used in the first reaction. Also, it is possible to produce a mutant which is excellent in properties such as stability, productivity, and reactivity.

The base sequence encoding the resultant enzyme and the information thereof may be obtained by protein sequencing, DNA sequencing, or a known genetic engineering technique using the above-mentioned enzyme or a natural microorganism capable of producing the enzyme.

The enzyme to be used in the first reaction of the present invention may also be obtained by a known bioinformatics technique. The sequence of SEQ ID NO: 1 is one example of the amino acid sequence of a preferable enzyme to be used in the first reaction in the measurement method of the present invention. Therefore, if the sequence is used as a query to perform a homology search by BLAST search or the like on a database such as NCBI, EMBL, or GenomeNet, it is possible to obtain the information of a protein or gene having an amino acid sequence or base sequence which is the same as or similar to the sequence of SEQ ID NO: 1, that is, the information or gene information of an organism which may produce the enzyme to be possibly used in the first reaction.

The enzyme to be used in the first reaction can be obtained by a method of producing the enzyme, which includes a step of producing a natural microorganism which is capable of producing the enzyme and is obtained by the above-mentioned method and the enzyme produced based on the base sequence of the enzyme or the information of the base sequence. Examples of the step of producing the enzyme include a cell-free enzyme synthesizing system including the base sequence encoding the enzyme. Preferable examples thereof include a step where a cell including the base sequence encoding the enzyme is used, a step where a microorganism having the base sequence encoding the enzyme such as a natural microorganism capable of producing the enzyme is used, and a step where a transformant including the base sequence encoding the enzyme is used.

In the case of employing the cell-free enzyme synthesizing system including the base sequence encoding the enzyme to be used in the first reaction, the base sequence encoding the first enzyme may be used in a known cell-free enzyme synthesizing system derived from wheat germ, *Escherichia coli*, rabbit reticulocytes, insect cells, or the like.

Meanwhile, in the case of employing the step where the cell including the base sequence encoding the enzyme is used, for example, a transformant may be prepared by inserting the base sequence encoding the enzyme to be used in the first reaction of a vector to introduce the vector into a host microorganism, and the enzyme may be produced using the resultant transformant.

The transformant including the base sequence encoding the enzyme to be used in the first reaction includes a cell or microorganism obtained by introducing a vector including the base sequence (recombinant phage or recombinant plasmid) into a host. A part or whole of the base sequence encoding the enzyme to be used in the first reaction may be synthesized and used. Preferably, the base sequence encoding the enzyme to be used in the first reaction may be obtained from a gene donor by a known method. The gene donor is not limited as long as the donor is a cell capable of producing the enzyme to be used in the first reaction, and preferable examples thereof include organisms capable of producing the enzyme to be used in the first reaction, such as the above-mentioned natural microorganisms obtained by screening and selection and organisms whose information has been obtained by bioinformatics techniques.

The vector where the base sequence encoding the enzyme to be used in the first reaction is inserted is preferably a phage or plasmid which can autonomously proliferate in a host microorganism and has been constructed for gene recombination. In the case where *Escherichia* genus microorganisms are used as a host, the phage vector may be λgt·λC or λgt·λB. For example, in the case where *Escherichia coli* is used as a host, the plasmid vector may be pET vector (Novagen), pBR322, pBR325, pACYC184, pUC12, pUC13, pUC18, pUC19, pUC118, pIN I, or BluescriptKS+; in the case where *Bacillus subtilis* is used as a host, the plasmid vector may be pWH1520, pUB110, or pKH300PLK; in the case where *Actinomycete* is used as a host, the plasmid vector may be pIJ680 or pIJ702; in the case where yeast, in particular, *Saccharomyces cerevisiae* is used as a host, the plasmid vector may be YRp7, pYC1, or YEp13. In the present invention, the plasmid vector to be inserted into host *Escherichia coli* is preferable. The promoter is not particularly limited as long as expression can be achieved in a host.

Such a vector is cleaved with a restriction enzyme which can produce the same terminal as the terminal of the base sequence produced by the restriction enzyme which has been used for cleavage of the base sequence encoding an enzyme to be used in the first reaction, to thereby prepare vector fragments, and the fragments of the base sequence encoding the enzyme to be used in the first reaction is ligated to the vector fragments with a DNA ligase in accordance with a conventional method. Then, the base sequence encoding the enzyme to be used in the first reaction is inserted into a target vector, to thereby prepare a recombinant phage or recombinant plasmid.

The host into which the recombinant plasmid is introduced may be a cell or microorganism where the recombinant plasmid can proliferate autonomously and stably. For example, in the case where the host microorganism is a microorganism belonging to *Escherichia coli*, the host may be *Escherichia coli* B, K, or C strain, which includes *Escherichia coli* BL21, *Escherichia coli* DH1, *Escherichia coli* JM109, *Escherichia coli* JM101, *Escherichia coli* W3110, and *Escherichia coli* C600, or a lysogenic bacterium thereof. In the case where the host microorganism is a microorganism belonging to the genus *Bacillus*, the host may be *Bacillus subtilis* or *Bacillus megaterium*. In the case where the host microorganism is a microorganism belonging to Actinomycete, the host may be *Streptomyces lividans* TK24. In the case where the host microorganism is a microorganism belonging to *Saccharomyces cerevisiae*, the host may be *Saccharomyces cerevisiae* INVSC1. In the present invention, *Escherichia coli* is preferably used as the host microorganism.

Preferable examples of the method of producing the enzyme to be used in the first reaction using a transformant including the base sequence encoding the enzyme further include a method of producing a recombinant enzyme in a bacterium belonging to the genus *Rhodococcus* (Japanese Patent No. 3944577, Japanese Patent No. 3793812). Specifically, the method involves inserting the base sequence encoding the enzyme to be used in the first reaction into a plasmid vector such as pTip QC1 or pTip QC2 suitable for low-temperature production of the recombinant enzyme and using a transformant obtained by introducing the recombinant plasmid into a lysozyme-sensitive microorganism. Preferable examples of the lysozyme-sensitive microorganism include microorganisms belonging to the genus *Rhodococcus* (Japanese Patent No. 3876310).

The conditions of culture of a natural microorganism capable of producing the enzyme to be used in the first reaction or a transformant including the base sequence encoding the enzyme may be selected in consideration of nutritional and physiological properties. The culture is performed usually in a liquid medium, but in the case where the culture is performed industrially, deep aeration stirring culture is employed advantageously. Nutritional sources of the medium may widely include ones which are usually used in culture of microorganisms. The culture temperature may vary in the range that allows a microorganism serving as a host to grow and allows the enzyme to be used in the first reaction to be produced. In the case of *Escherichia coli*, the lower limit of the temperature is 10° C. or more, preferably 20° C. or more, and more preferably 25° C. or more, while the upper limit is 45° C. or less, preferably 42° C. or less, and more preferably 38° C. or less. In the case of *Actinomycete*, the lower limit of the temperature is 4° C. or more, preferably 10° C. or more, and more preferably 20° C. or more, while the upper limit is 50° C. or less, preferably 42° C. or less, and more preferably 37° C. or less. Although the culture conditions slightly vary depending on the conditions, the culture may be completed in an appropriate time when the amount of the enzyme to be used in the first reaction reaches a maximum level. In the case of *Escherichia coli*, the lower limit of the time is usually 10 hours or more, preferably 12 hours or more, and more preferably 17 hours or more, while the upper limit is 60 hours or less, preferably 48 hours or less, and more preferably 30 hours or less. In the case of *Actinomycete*, the lower limit of the time is usually 17 hours or more, preferably 20 hours or more, and more preferably 24 hours or more, while the upper limit is 80 hours or less, preferably 72 hours or less, and more preferably 48 hours or less. The pH value of the medium may appropriately vary as long as a microorganism can grow and the enzyme to be used in the first reaction can be produced. In the case of *Escherichia coli* or *Actinomycete*, preferably, the lower limit of the pH value is pH 5.8 or more and preferably pH 6.2 or more, while the upper limit is pH 8.5 or less and preferably pH 7.5 or less.

The enzyme to be used in the first reaction can be produced by a method including a step of acquiring the enzyme produced as described above. To facilitate the procedure, the enzyme may be obtained in the form of cells containing bacterial cells, regardless of sterilized or non-sterilized, but culture impurities or cell breakage products are preferably removed to some extent to prepare an enzyme containing impurities. Further, for a certain purpose or usage, the crude enzyme of the enzyme preferably substantially includes no impurities as well. However, in general, the purity of the enzyme is adjusted to, for example, 50% or more, 70% or more, or 95% or more. The purity may be determined by a known method such as SDS-PAGE or HPLC.

In the case where the enzyme to be used in the first reaction is produced by culturing and obtaining a natural microorganism screened and selected as described above or a transformant microorganism including the base sequence encoding the enzyme, the microorganism is cultured in a nutritive medium to produce the enzyme in bacterial cells or a culture medium. In the case where the enzyme is produced in the cells, after the completion of culture, the cells are collected from the resultant culture by a technique such as filtration or centrifugation. Thereafter, the cells are broken by a mechanical process or a process using an enzyme such as lysozyme, and if necessary, EDTA and/or an appropriate surfactant are added. Then, the enzyme is concentrated or is not concentrated, and the enzyme to be used in the first reaction is precipitated by fractional precipitation using an organic solvent such as acetone, methanol, or ethanol, or by salting-out using ammonium sulfate or salt, followed by collection. If necessary, the precipitates are subjected to dialysis or isoelectric precipitation and then treated by gel filtration, adsorption chromatography such as affinity chromatography, ion-exchange chromatography, or hydrophobic chromatography, to thereby prepare the enzyme to be used in the first reaction. In addition, those methods may be used in an appropriate combination. In the case where the enzyme of the present invention is produced in a culture medium, the cells are removed from the culture by a technique such as filtration or centrifugation, and the culture medium may be subjected to the same treatments as in the case where the enzyme is produced in cells.

Any of salts, sugars, enzymes, lipids, and surfactants may be added as a stabilizer or vehicle to the resultant enzyme to be used in the first reaction or may not be added, and the enzyme is subjected to a treatment such as ultrafiltration concentration or freeze-drying, to thereby obtain a liquid or solid enzyme to be used in the first reaction. In the case where the freeze-drying is appropriately performed, sucrose, mannitol, salt, albumin, or the like may be added as a stabilizer or vehicle at a concentration of about 0.5 to 10%.

The natural microorganism which produces the enzyme to be used in the first reaction of the present invention is preferably a microorganism belonging to the genus *Thermotoga*, more preferably *Thermotoga maritima*, and most preferably *Thermotoga maritima* DSM 3109 strain. The enzyme to be used in the first reaction of the present invention is preferably PPDK.

The typical amino acid sequence of the enzyme to be used in the first reaction of the present invention is the amino acid sequence of SEQ ID NO: 1. An example of the base sequence encoding the amino acid sequence is the base sequence of SEQ ID NO: 2. The base sequence has been determined by Nelson et al. (Nature, 1999, vol. 399, pp. 323). However, the properties of the enzyme encoded by the base sequence have not been clarified so far, and the enzyme has been predicted to be PPDK. That is, the fact that the amino acid sequence of SEQ ID NO: 1 encoded by the base sequence of SEQ ID NO: 2 catalyzes the reaction of [Formula 1] has not been known at all.

The method of producing the enzyme to be used in the second reaction of the present invention is the same as the method of producing the enzyme to be used in the first reaction of the present invention. The natural microorganism capable of producing the enzyme to be used in the second reaction of the present invention is preferably a eukaryotic organism, more preferably yeast, particularly preferably a microorganism belonging to the genus *Saccharomyces*, and most preferably *Saccharomyces cerevisiae*. The enzyme to be used in the second reaction of the present invention is preferably NMNATase. The typical amino acid sequence of the enzyme to be used in the second reaction of the present invention is the amino acid sequence of SEQ ID NO: 6. An example of the base sequence encoding the amino acid sequence is the base sequence of SEQ ID NO: 7. The base sequence has been determined as yNMNAT-2 by Emanuelli et al. (Protein Expression and Purification, 2003, vol. 27, pp. 357), and it has been reported that the enzyme encoded by the base sequence is NMNATase but requires dATP as a substrate. Therefore, it seems to be natural that, even if a person skilled in the art uses the NMNATase encoded by the base sequence, based on the above prior literatures, it is impossible for a person to measure pyrophosphate selectively without the effect by dATP or dNTPs.

In the case where the third reaction of the present invention is performed enzymatically, the method of producing the enzyme is the same as the method of producing the enzyme to be used in the first reaction of the present invention.

In the case where the fourth reaction of the present invention is performed enzymatically, the method of producing the enzyme is the same as the method of producing the enzyme to be used in the first reaction of the present invention.

A conventional method of measuring a nucleic acid includes: a method involving binding a nucleic acid labeled with a radioactive isotope, biotin, or enzyme to a nucleic acid to be measured, and measuring the nucleic acid; and the like. Those methods require a process for separating the bound substance from unbound substances and further require a special facility, device, or the like for measurement. The same holds for a measurement method involving staining a nucleic acid to be measured with a fluorescent substance such as ethidium bromide or SYBR GreenI (registered trademark).

On the other hand, examples of the method of measuring a nucleic acid based on the amount of pyrophosphate produced include a method involving reacting the pyrophosphate with pyrophosphatase to produce phosphate and detecting the resultant phosphate (Japanese Patent Application Laid-open No. Hei 07-59600). In this method, in order to measure the pyrophosphate selectively, it is necessary to eliminate phosphate which may present in a sample or reagent component.

Examples of the method of measuring a nucleic acid based on the amount of pyrophosphate produced as an index further include: a known method involving reacting the pyrophosphate with ATP sulfurylase to produce ATP and detecting the ATP by luminescence using luciferase (PCT WO 92/16654A) and a known method in which pyruvate orthophosphate dikinase and luciferase are used (Japanese Patent Application Laid-open No. 2007-097471). In these methods, in order to measure the pyrophosphate selectively, it is necessary to eliminate dATP which may present in a sample and to use a device for luminescence measurement.

Examples of the method of measuring a nucleic acid based on the amount of pyrophosphate produced as an index further include a known method in which hypoxanthine phosphoribosyltransferase and xanthine dehydrogenase/oxidase are used (Japanese Patent Application Laid-open No. 2003-174900). In this method, in order to measure the pyrophosphate selectively, it is necessary to eliminate the hypoxanthine which may present in a sample.

Examples of the method of measuring a nucleic acid based on the amount of pyrophosphate produced as an index further include a known method in which kinase, an enzyme for producing ATP from the pyrophosphate, and dehydrogenase which requires NAD or NADP as a coenzyme are used (Japanese Patent Application Laid-open No. 2006-187251). In this method, in order to measure the pyrophosphate selectively, it is necessary to eliminate dATP which is present in a sample.

The measurement method of the present invention may be a method of selectively measuring pyrophosphate, which is not affected even if the pyrophosphate and the above-mentioned substances coexist in, for example, a sample on one or two or more steps selected from the steps including the first to fourth reactions. Meanwhile, in the case of detection of reduced NTBs by the measurement method of the present invention, a nucleic acid can be measured by visible light based on the amount of pyrophosphate produced as an index.

Therefore, measurement can be performed easily by visual observation or using a general-purpose equipment.

Accordingly, if the measurement method of the present invention is used for, for example, measurement for a test solution during or after nucleic acid amplification reactions by the nucleic acid amplification method, a nucleic acid can be preferably measured easily based on the amount of pyrophosphate produced as an index.

EXAMPLES

Hereinafter, the present invention will be described based on examples or the like, but the scope of the present invention should not be construed as limited to the following examples or the like. The following techniques described as "in accordance with a conventional method" are ones which can be performed in accordance with, for example, the method of Maniatis et al. (Maniatis, T., et al., Molecular Cloning. Cold Spring Harbor Laboratory, 1982, 1989), the above-mentioned basic experimental methods for proteins and enzymes, or the instructions attached to commercially available enzymes or kits. Meanwhile, the following measurement values may vary depending on measurement conditions or accuracy of used equipment.

Unless otherwise specified, the reagents to be used in the present invention are those manufactured by Wako Pure Chemicals Industries, Ltd., Sigma-Aldrich Corporation, or TAKARA BIO INC. and are easily available. DSM strains may be purchased from Deutsche Sammlung von Mikroorganismen und Zellkulturen GmbH. ATCC strains may be purchased from American Type Culture Collection. The manufacturers or purities of the reagents are not particularly limited.

[PPDK Activity Measurement Method 1]
[Reaction reagent mixture 1 for PPDK activity measurement]
100 mM HEPES/NaOH pH 7.5
5 mM PEP
2 mM AMP
4 mM $MgCl_2$
4 mM pyrophosphate
0.15 mM NADH 1 ml of the reaction reagent mixture 1 for PPDK activity measurement was preliminarily heated in a quartz cell with a layer length of 1 cm at 37° C. for 1 minute, and 3 µl of lactate dehydrogenase (5,000 U/ml, Roche) were added, followed by heating at 37° C. for 1 minute. PPDK diluted to an appropriate concentration (10 µl) was mixed therein to start the enzymatic reaction. Absorbance was measured at 340 nm after the start of the reaction, and an absorbance change per 1 minute when the reaction proceeded linearly was measured as "As/min". An absorbance change per 1 minute when purified water was used instead of the PPDK was measured as "Ab/min". The enzymatic activity (U/ml) was calculated by [Expression 5]. Herein, unless otherwise specified, measurement of PPDK activity was performed by the PPDK activity measurement method 1.

Enzymatic activity (U/ml)={(As/min−Ab/min)/6.22}× 1.013/0.01×dilution fold     [Expression 5]

[PPDK Activity Measurement Method 2]
The above-mentioned PPDK activity measurement method 1 is based on continuous reactions and can measure the activities of many samples at the same time. However, the measurement is performed at 37° C. in view of the thermostability of lactate dehydrogenase, and hence it is difficult to accurately estimate the properties of the PPDK of the present invention, which is considered to have an optimum temperature of 50° C. or more. The first reaction in the PPDK activity measurement method 2 was performed at a temperature (50° C.) close to the optimum temperature for growing *Thermotoga maritima* (80° C.), and the method may accurately estimate the properties of the PPDK of the present invention. However, in this method, trichloroacetic acid should be used with care, and the method includes two steps of measuring the activities and requires cumbersome procedures for measuring the activities of many samples at the same time. In the present example, if necessary, the PPDK activity measurement method 2 is used. If the method is used, special note will be made.

[Reaction Reagent Mixture 2-1 for PPDK Activity Measurement]
100 mM HEPES/NaOH pH 7.5
5 mM PEP
2 mM AMP
5 mM $MgCl_2$
5 mM pyrophosphate
An enzyme solution and distilled water are added to have a final volume of 400 µl.

[Reaction Reagent Mixture 2-2 for PPDK Activity Measurement]
1.15 M Tris/HCl pH 8.0
0.135 mM NADH
5 U/ml lactate dehydrogenase
400 µl of centrifuged supernatant are added to have a final volume of 1 ml.

The PPDK activity measurement method 2 is a method of measuring the activity in an enzymatic reaction in two steps. The reaction reagent mixture 2-1 for PPDK activity measurement was prepared using PPDK diluted to an appropriate concentration. In this step, a sample prepared without adding an enzyme was defined as "blank", while a sample prepared by adding an enzyme was defined as "test". A PPDK solution and distilled water were added to the reaction reagent mixture 2-1 for PPDK activity measurement, the temperature of which had been adjusted to 50° C., to have a final volume of 400 µl, and the reaction was started. Incubation was performed for 10 minutes to perform the first step reaction. Subsequently, the reaction solution was cooled in ice, and 50 µl of 50% trichloroacetic acid were added to stop the reaction. The reaction solution was centrifuged at 4° C. and 15,000 rpm for 10 minutes, and the resultant supernatant (400 µl) was placed in an Eppendorf tube containing the reaction reagent mixture 2-2 for PPDK activity measurement. The tube was incubated at 37° C. for 10 minutes to perform the second step reaction, and the absorbance at 340 nm in "blank" and "test" was measured as "Ab" and "At", respectively. One unit of enzymatic activity was defined as the amount of an enzyme necessary for converting 1 µmol of PEP into pyruvic acid at 37° C. for 1 minute, and the enzymatic activities were calculated based on the expression "Ab-At" (the millimolar extinction coefficient of NADH: 6.22).

[NMNATase Activity Measurement Method]
[Reaction Reagent Mixture for NMNAtase Activity Measurement]
100 mM HEPES/NaOH pH 7.5
2 mM β-nicotinamide mononucleotide
2 mM ATP
2 mM $MgCl_2$
1 mM cholic acid
5 U/ml 12α-HSD (manufactured by Asahi Kasei Pharma Corporation)

1 ml of reaction reagent mixture for NMNATase activity measurement was preliminarily heated in a quartz cell with a layer length of 1 cm at 37° C. for 1 minute, and 30 µl of NMNATase diluted to an appropriate concentration were mixed therein to start the enzymatic reaction. Absorbance was measured at 340 nm after the start of the reaction, and an absorbance change per 1 minute when the reaction proceeded linearly was measured as "As/min". An absorbance change per 1 minute when purified water was used instead of the NMNATase was measured as "Ab/min". The enzymatic activity (U/ml) was calculated by [Expression 6].

Enzymatic activity (U/ml)={(As/min−Ab/min)/6.3}× 1.03/0.03×dilution fold [Expression 6]

[Protein Concentration Measurement Method]

The protein concentrations in unpurified enzymes, crude enzyme solutions, purified enzymes, and the like were measured using Protein Assay Kit (Bradford method) manufactured by Bio-Rad in accordance with the method described in the instructions, and the concentrations were calculated using BSA as a standard.

Example 1

<DNA Extraction>

Cells of *Thermotoga maritima* DSM 3109 strain was treated in a 1 mg/ml lysozyme solution containing 50 mM Tris/HCl (pH 8.0), 50 mM EDTA, and 15% sucrose at 37° C. for 10 minutes, and SDS was added thereto to have at a final concentration of 0.25% to lyse the cells. An equal amount of a mixture of phenol/chloroform (1:1) was added, and the whole was stirred for 30 minutes and centrifuged (12,000 rpm, 15 minutes), followed by collection of the aqueous layer. One-tenth volume of 3 M sodium acetate (pH 5.5) was mixed in the aqueous layer, and a double volume of ethanol was layered gently, followed by separation of genomic DNA with winding the DNA onto a glass rod. The separated genomic DNA was dissolved in 10 mM Tris/HCl (pH 8.0), 1 mM EDTA solution (herein, sometimes referred to as "TE"), and an appropriate amount of RNaseA was added, followed by incubation at 37° C. for 1 hour to decompose RNA mixed in the solution. An equal volume of a mixture of phenol/chloroform (1:1) was added, and the whole was treated in the same way as above, followed by separation of the aqueous layer. One-tenth volume of 3 M sodium acetate (pH 5.5) and a double volume of ethanol were added to the aqueous layer, and the genomic DNA was separated again by the above-mentioned method. The chromosome was dissolved in TE, and a mixture of TE-saturated phenol and chloroform (1:1) was added. The whole was suspended, and centrifugation was repeated in the same way as above. Then, the upper layer was transferred to another container again. 3 M sodium acetate buffer (pH 5.5) and ethanol were added to the upper layer, and the whole was stirred and cooled at −70° C. for 5 minutes, followed by centrifugation (2,000 G, 4° C., 15 minutes). The precipitated chromosome was washed with 75% ethanol and dried under reduced pressure, to thereby produce a DNA specimen of *Thermotoga maritima* DSM 3109 strain.

Example 2

<Amplification of Gene of SEQ ID NO: 1 by PCR>

Primers of SEQ ID NOs: 8 and 9 were designed so that the gene of SEQ ID NO: 2 was inserted into multicloning sites, NdeI and HindIII sites, in pET21a(+) or pET28a(+) (Novagen). In the case of using pUC118, primers of SEQ ID NOs: 10 and 9 were designed so that the gene was inserted into multicloning sites, XbaI and HindIII sites. PCR was performed in accordance with a conventional method using KOD DNA polymerase. The resultant PCR product of about 2.7 kbp was purified in accordance with a conventional method, for example, a method using QIAGEN QIAquick PCR Purification Kit.

Example 3

<Ligation to Expression Vector>

The PCR product obtained by using the primers of SEQ ID NOs: 8 and 9 purified in Example 2 was treated with restriction enzymes NdeI and HindIII in accordance with a conventional method (insert A). The PCR product obtained by using the primers of SEQ ID NOs: 10 and 9 purified in Example 2 was treated with restriction enzymes XbaI and HindIII in accordance with a conventional method (insert B). The inserts A and B were purified in accordance with a conventional method, for example, a method using QIAGEN QIAquick PCR Purification Kit. Insert A was ligated to pET21a(+) or pET28a(+), which had been treated with restriction enzymes NdeI and HindIII and purified, in accordance with a conventional method, to thereby prepare pET21a(+)/TM0272 or pET28a(+)/TM0272. Insert B was ligated to pUC118, which had been treated with restriction enzymes XbaI and HindIII and purified, in accordance with a conventional method, to thereby prepare pUC118/TM0272. The recombinant plasmids obtained by purifying positive clones obtained by colony direct PCR were subjected to DNA sequencing to confirm whether the insert sequences were correct.

Example 4

<Expression Check of pET21a(+)/TM0272 and pET28a(+)/TM0272> pET21a(+)/TM0272 and pET28a(+)/TM0272 were transformed into *Escherichia coli* BL21 (DE3) in accordance with a conventional method, and the bacterium was inoculated into SB medium (12 g of tryptone, 24 g of yeast extract, and 5 ml of glycerol were dissolved in 0.9 L of distilled water, and the whole was sterilized at 121° C. for 20 minutes. 12.5 g of potassium monohydrogen phosphate and 3.8 g of potassium dihydrogen phosphate were dissolved in 0.1 L of distilled water, and the whole was sterilized at 121° C. for 20 minutes. The solutions were separately cooled to room temperature and mixed, to thereby prepare 1 L of SB medium) containing 50 µg/ml ampicillin. The bacterium was cultured at 37° C. for 13 hours, and IPTG was added to have at a final concentration of 1 mM, followed by culture for 5 hours. The culture medium was centrifuged to collect the cells, and the cells were washed with physiological saline and suspended in 20 mM HEPES/NaOH (pH 7.5), the weight of which was four times the wet weight of the cells. The suspension was subjected to sonication and centrifugation, and the resultant supernatant was defined as a crude enzyme solution.

Example 5

<Expression Check of pUC118/TM0272> pUC118/TM0272 was transformed into *Escherichia coli* JM109 in accordance with a conventional method, and the bacterium was inoculated into SB medium containing 50 µg/ml ampicillin. The cells were cultured at 37° C. for 18 hours, and the culture medium was centrifuged to collect the cells. The cells were washed with physiological saline and suspended in 20 mM HEPES/NaOH (pH 7.5), the weight of which was four times the wet weight of the cells. The suspension was subjected to sonication and centrifugation, and the resultant supernatant was defined as a crude enzyme solution.

Example 6

<Heat Treatment of Crude Enzyme Solution>

The crude enzyme solution obtained in Example 5 was heat-treated at 80° C. for 15 minutes and centrifuged, and the resultant supernatant was defined as a crudely purified solution. FIG. 1 shows the SDS-PAGE of the crudely purified solution.

Example 7

<PPDK Purification 1>

The crudely purified solution obtained in Example 6 was applied to an anion-exchange chromatography column (UnoQ (registered trademark), Bio-Rad) equilibrated with 20 mM HEPES/NaOH (pH 7.5). The column was washed with 20 mM HEPES/NaOH (pH 7.5), the volume of which was five times or more the bed volume, and linear gradient elution was performed using 20 mM HEPES/NaOH (pH 7.5) and 20 mM HEPES/NaOH (pH 7.5) containing 0.5 M NaCl, the volume of which was 12 times the bed volume. Active fractions were collected and dialyzed against 100-fold volume of 20 mM HEPES/NaOH (pH 7.5) to perform desalting.

The desalted PPDK was applied to a column containing hydroxyapatite (Bio-Rad) equilibrated with 10 mM potassium phosphate (pH 7.5). The column was washed with 10 mM potassium phosphate (pH 7.5), the volume of which was 5 times or more the bed volume, and linear gradient elution was performed using 300 mM potassium phosphate (pH 7.5), the volume of which was 12 times the bed volume. Active fractions were collected and dialyzed against 100-fold volume of 20 mM HEPES/NaOH (pH 7.5) containing 1 mM DTT or desalted using a gel filtration agent G-25 (GE Healthcare Bio-Sciences) equilibrated with 20 mM HEPES/NaOH containing 1 mM DTT, to thereby prepare a purified enzyme.

In the present example, about 5 mg of a purified enzyme with a specific activity of about 5 U/mg was obtained at a yield of about 15% from 500 ml of a culture medium. Measurement was performed by the PPDK activity measurement method 2.

Example 8

<PPDK Purification 2>

The crude enzyme solution obtained in Example 4 was applied to a nickel affinity gel chromatography column (Sigma-Aldrich Corporation) equilibrated with 20 mM HEPES/NaOH (pH 7.5) containing 0.2 M NaCl. The column was washed with 20 mM HEPES/NaOH (pH 7.5) containing 0.2 M NaCl, the volume of which was 5 times or more the bed volume, and adsorbed fractions were eluted with 20 mM HEPES/NaOH (pH 7.5) containing 0.2 M NaCl and 0.2 M imidazole.

20% ammonium sulfate was added to the eluted active fractions, and the whole was applied to a phenyl-Toyopearl chromatography column (Tosoh Corporation) equilibrated with 20 mM HEPES/NaOH (pH 7.5) containing 20% ammonium sulfate. The column was washed with 20 mM HEPES/NaOH (pH 7.5) containing 20% ammonium sulfate, the volume of which was 5 times or more the bed volume, and linear gradient elution was performed using 20 mM HEPES/NaOH (pH 7.5), the volume of which was 12 times the bed volume. The eluted active fractions were desalted in the same way as in Example 7. The yield was about 50%. The specific activity of the PPDK prepared in the present example was found to be 7 U/mg. Measurement was performed by the PPDK activity measurement method 2.

Example 9

<Confirmation of PPDK Activity>

10 µl of the PPDK obtained in Example 7 was added to a reaction solution containing 100 mM HEPES/NaOH (pH 7.5), 1 mM AMP, 1 mM $MgCl_2$, 1 mM PEP, and 1 mM pyrophosphate, and the whole was allowed to react at 50° C. for 20 minutes. The reaction solution was analyzed by HPLC using Asahipak GS-320 (manufactured by Showa Denko K.K.). Absorbance at 260 nm was measured using a mobile phase of 200 mM sodium phosphate (pH 3) at a flow rate of 0.5 ml/min at a column temperature of room temperature. A mixture of ATP, ADP, AMP, and adenosine was analyzed instead of the reaction solution under the same conditions, with HPLC, and separated, and the results are illustrated in FIG. 2. FIG. 3 illustrates the results of separation of the reaction solution before the reaction. FIG. 4 illustrates the results of separation of the reaction solution after the reaction. From these results, the PPDK activity was confirmed because ATP was produced by the reaction when AMP was used as a substrate.

Example 10

<PPDK Frozen Storage Stability>

Non-desalted PPDK (1.2 U/ml) obtained in Example 7 was freeze-stored at −20° C. and unfreezed 2 weeks later, and the activities before and after the freeze storage were compared. As a result, the remaining activity even after the freeze storage was found to be 94%.

Example 11

<PPDK Refrigerated Storage Stability>

The non-desalted PPDK (1.2 U/ml) obtained in Example 7 was stored at 4° C., and the activities were measured 0, 5, 8, 12, 19, and 27 days later. The results are shown in FIG. 5. The remaining activity of the PPDK even after the 27-day refrigerated storage was found to be 80% or more. Moreover, even after the PPDK was stored under the same conditions for 9 months, the remaining activity was found to be 80% or more. The PPDK activities were measured by the measurement method 2.

Example 12

<Thermostability 1>

The desalted PPDK obtained in Example 7 (about 0.2 mg/ml) was heat-treated at a temperature in the range from 50° C. to 100° C. for 20 minutes. The activity of an untreated enzyme is defined as 100%, and the remaining activity (%) is shown in FIG. 6. The results reveal that the activity of the PPDK of the present invention is maintained to 90% or more after a heat treatment at 90° C. for 20 minutes. The PPDK activities were measured by the measurement method 2.

Example 13

<Thermostability 2>

The desalted PPDK obtained in Example 7 (about 0.2 mg/ml) was heat-treated at a temperature in the range from 80° C. to 90° C. between 0 and 1 hour. The activity of an untreated enzyme is defined as 100%, and the remaining activity (%) is shown in FIG. 7. The results reveal that the activity of the PPDK of the present invention is maintained to 70% or more after a heat treatment at 90° C. for 1 hour and to 90% or more after a heat treatment at 80° C. for 1 hour. The PPDK activities were measured by the measurement method 2.

Example 14

<Optimum pH>
The buffers in the reaction reagent mixture 2-1 for PPDK activity measurement were changed to a Bis-Tris/HCl buffer in the range from pH 6 to pH 7 (the mark "○" in FIG. 8), an HEPES/NaOH buffer in the range from pH 7 to pH 8 (the mark "Δ" in FIG. 8), and a glycylglycine/NaOH buffer in the range from pH 8 to pH 9 (the mark "□" in FIG. 8), and the activities were measured to determine the optimum pH of the PPDK of the present invention. The maximum activity is defined as 100%, and the relative activities (%) are shown in FIG. 8. The optimum pH of the PPDK of the present invention was found to be in the range from pH 7 to pH 7.5. The PPDK activities were measured by the measurement method 2. The desalted PPDK obtained in Example 7 was used.

Example 15

<pH Stability>
The desalted PPDK obtained in Example 7 was dissolved, to have a concentration of about 0.06 mg/ml, in a 100 mM citric acid/sodium citrate buffer (the mark "○" in FIG. 9) in the range from pH 4 to pH 6.5, an imidazole/HCl buffer (the mark "Δ" in FIG. 9) in the range from pH 6.5 to pH 7, an HEPES/NaOH buffer (the mark "□" in FIG. 9) in the range from pH 7 to pH 8, a glycylglycine/NaOH buffer (the mark "●" in FIG. 9) in the range from pH 8 to pH 9, and a glycine/NaOH buffer (the mark "■" in FIG. 9) in the range from pH 9 to pH 11, and the solutions were stored at 50° C. for 20 minutes. The maximum activity is defined as 100%, and the remaining activities (%) are shown in FIG. 9. The results reveal that the activity of the PPDK of the present invention is maintained to 80% or more in the range from pH 4.5 to 11 after storage at 50° C. for 20 minutes. The PPDK activities were measured by the measurement method 2.

Example 16

<Coenzyme Specificity>
The activity measurement was performed using ADP, IMP, CMP, GMP, TMP, and UMP instead of AMP in the reaction reagent mixture 2-1 for PPDK activity measurement. As a result, it was found that the PPDK of the present invention acted specifically with AMP as a coenzyme in the presence of magnesium ions when PEP and pyrophosphate were used as substrates and did not act with ADP, IMP, CMP, GMP, TMP, and UMP. The desalted PPDK obtained in Example 7 was used.

Example 17

<Metal Ion>
$MgCl_2$ in the reaction reagent mixture 2-1 for PPDK activity measurement was changed to $CoCl_2$, $NiCl_2$, $CaCl_2$, and $ZnCl_2$ to measure the activity of the PPDK of the present invention, which had been dialyzed twice against 100-fold volume of 20 mM HEPES/NaOH (pH 7.5) containing 1 mM EDTA and 0.2 M sodium sulfate. As a result, it was found that that the PPDK of the present invention had no activity in the absence of a metal ion and in the presence of $CaCl_2$ and $ZnCl_2$, while when the activity in the presence of $MgCl_2$ was defined as 100%, the PPDK of the present invention had relative activities of 74% and 29% in the presence of $CoCl_2$ and $NiCl_2$, respectively. The desalted PPDK obtained in Example 7 was used.

Example 18

<Molecular Weight>
The calculated value and measured value of the molecular weight are as follows.
(1) The value calculated from the primary sequence of amino acids: 98,102
(2) The measured value by the SDS-PAGE for the desalted PPDK obtained in Example 7 (the arrow in FIG. 1): 83,000

Example 19

<Km Value>
The apparent Km values of the desalted PPDK obtained in Example 7 for PEP, pyrophosphate, and AMP were calculated based on the Lineweaver-Burk reciprocal plot. The apparent Km values for PEP, pyrophosphate, and AMP were found to be 0.32 mM, 1.12 mM, and 0.065 mM, respectively. The PPDK activity was measured by the measurement method 2.

Example 20

<Preparation of NMNATase>
The DNAs of *Saccharomyces cerevisiae* 1-2, 3-2, and 6-2 strains were obtained in the same way as in Example 1. Primers of SEQ ID NOs: 11 and 12 were designed so that the gene of SEQ ID NO: 7 was inserted into multicloning sites, XbaI and HindIII sites, in pUC118. pUC118/Sc1-2, pUC118/Sc3-2, and pUC118/Sc6-2 were prepared in the same way as in Example 2, and crude enzyme solutions of NMNATase were prepared in the same way as in Example 5. Each crude enzyme solution was adsorbed to Q sep.BB (GE Healthcare Bio-Sciences) equilibrated with a 10 mM Tris/HCl buffer (pH 8.0). The column was washed well with a 10 mM Tris/HCl buffer (pH 8.0), and linear gradient elution was performed using 10 mM Tris/HCl buffers (pH 8.0) containing 0 and 0.5 M KCl. Ammonium sulfate was added to active fractions at a final concentration of 15%, and the whole was adsorbed to Phenyl sep.FF (GE Healthcare Bio-Sciences) equilibrated with a 10 mM potassium phosphate buffer (pH 7.5) containing 15% ammonium sulfate. Then, linear gradient elution was performed using 10 mM potassium phosphate buffers (pH 7.5) containing 15 and 0% ammonium sulfate. The active fractions were desalted using G-25 equilibrated with a 10 mM potassium phosphate buffer (pH 7.5), and the whole was adsorbed to DEAE sep.FF (GE Healthcare Bio-Sciences) equilibrated with a 10 mM potassium phosphate buffer (pH 7.5). The column was washed well with a 10 mM potassium phosphate buffer (pH 7.5), and linear gradient elution was performed using 10 mM potassium phosphate buffers (pH 7.5) containing 0 and 0.5 M KCl. The active fractions were desalted using G-25 equilibrated with a 10 mM potassium phosphate buffer (pH 7.0), to thereby obtain NMNATases 1-2, 3-2, and 6-2. In the present example, about 60 U, 700 U, and 400 U of the NMNATases 1-2, 3-2, and 6-2 were obtained from 100 ml of the culture mediums.

Example 21

<Comparison of dNTPs/ATP in NMNATase>
The following [Composition] was prepared, and the dNTPs/ATP (ratio of substrate specificity for dNTPs and substrate specificity for ATP) of the NMNATase was measured. Measurement was performed using Hitachi 7080 autoanalyzer. Parameters are as follows: sample: 20 μl; R1: 180 μl of [Composition]; measurement dominant wavelength: 340 nm; measurement sub-wavelength: 405 nm; Rate A; reaction time: 5 minutes; photometric point: 2-3. Values were calculated by subtracting a blank value in the case of purified water. 1 mM dNTPs and ATP were used as samples. The term "Rate A" refers to a measurement method in the measurement device (Hitachi 7080 autoanalyzer), and a person skilled in the art can understand the method if he reads the instructions of the Hitachi 7080 autoanalyzer. As a result, the dNTPs/ATP values in NMNATases 1-2, 3-2, and 6-2 were found to be 1.7, 1.3, and 0.8%, respectively.

[Composition]
100 mM HEPES/NaOH pH 7.5
1 mM β-nicotinamide mononucleotide
2 mM MgCl$_2$
1 mM cholic acid
5 U/ml 12α-HSD (manufactured by Asahi Kasei Pharma Corporation)
1 U/ml NMNATases 1-2, 3-2, and 6-2 prepared in Example 20

Example 22

<Pyrophosphate Measurement 1>

The following [Compositions] were prepared to perform the method of measuring pyrophosphate. Measurement was performed using the Hitachi 7080 autoanalyzer. Parameters are as follows: sample: 20 μl; R1: 150 μl of [Composition A]; R2: 150 μl of [Composition B]; measurement dominant wavelength: 340 nm; measurement sub-wavelength: 405 nm; 2 point end; reaction time: 10 minutes; photometric point: 16-31. Values were calculated by subtracting a blank value in the case of purified water. The concentration of the pyrophosphate was adjusted in the range of the lateral axis of the graph shown in FIG. 10 to prepare samples, and the measurement results are shown in FIG. 10. Measurement of the pyrophosphate was able to be performed using the composition of the present invention by the measurement method of the present invention. The marks ○, Δ, and □ in FIG. 10 show the concentrations of PPDK in [Composition A] 1, 5, and 10 U/ml, respectively. The term "2 point end" refers to a measurement method in the measurement device (Hitachi 7080 autoanalyzer), and a person skilled in the art can understand the method if he reads the instructions of the Hitachi 7080 autoanalyzer.

[Composition A]
100 mM HEPES/NaOH pH 7.5
1 mM PEP
1 mM AMP
1 mM MgCl$_2$
1, 5, 10 U/ml PPDK after desalted prepared in Example 7

[Composition B]
100 mM HEPES/NaOH pH 7.5
1 mM β-nicotinamide mononucleotide
2 mM MgCl$_2$
1 mM cholic acid
5 U/ml NMNATase 3-2 prepared in Example 20
5 U/ml 12α-HSD (manufactured by Asahi Kasei Pharma Corporation)

Example 23

<Pyrophosphate Measurement 2>

The following [Compositions] were prepared to perform the method of measuring pyrophosphate. Measurement was performed using the Hitachi 7080 autoanalyzer. Parameters are as follows: sample: 20 μl; R1: 150 μl of [Composition A]; R2: 150 μl of [Composition B]; measurement dominant wavelength: 546 nm; measurement sub-wavelength: 660 nm; Rate A; reaction time: 10 minutes; photometric point: 27-30. Values were calculated by subtracting a blank value in the case of purified water. The mark "○" in FIG. 11 shows the measurement results in the case of using 0 to 20 μM pyrophosphate as samples, while the mark "●" in FIG. 11 shows the measurement results in the case of using mixtures obtained by mixing 0 to 40 μM pyrophosphate and 0.8 mM dNTPs at a ratio of 1:1 as samples. In the case of using 0 to 20 μM pyrophosphate as samples, the results were Y=0.4X+5 and R2=0.996, while in the case of using mixtures obtained by mixing 0 to 40 μM pyrophosphate and 0.8 mM dNTPs at a ratio of 1:1 as samples, the results were Y=0.4X+14 and R2=0.991. As a result, it was found that the pyrophosphate was able to be measured at high accuracy even in the presence of the dNTPs. The reaction in the present example was found to be a cycling reaction because the reaction rate increased geometrically with time.

[Composition A]
100 mM HEPES/NaOH pH 7.5
1 mM PEP
1 mM AMP
1 mM MgCl$_2$
1 U/ml PPDK prepared in Example 7

[Composition B]
100 mM HEPES/NaOH pH 7.5
1 mM β-nicotinamide mononucleotide
1 mM MgCl$_2$
1 mM cholic acid
0.025% nitrotetrazolium blue
0.5 U/ml NMNATase 3-2 prepared in Example 20
5 U/ml 12α-HSD (manufactured by Asahi Kasei Pharma Corporation)
5 U/ml DI (manufactured by Asahi Kasei Pharma Corporation)

Example 24

<Pyrophosphate Measurement 3>

The concentration of pyrophosphate in the test solution during a nucleic acid amplification reaction by PCR was measured. The PCR was performed in the following [PCR mixture] using Blend Taq (manufactured by TOYOBO CO., LTD.). PCR conditions were 25 cycles of 94° C. for 30 seconds, 55° C. for 30 seconds, and 72° C. for 1 minute. At the time of each cycle number shown in the lateral axis of the graph shown in FIG. 12, part of [PCR mixture] was withdrawn as a test solution. The concentration of the pyrophosphate was detected using the following [Compositions]. pUC118/Sc6-2 obtained in Example 20 was used as a template to amplify the gene of SEQ ID NO: 7. The amplified gene was found to have a size of about 1.5 kbp. Quantification was performed by measuring an aqueous solution of 20 μM pyrophosphate as a calibrator and calculating the concentration of the pyrophosphate in each test solution. Measurement was performed using the Hitachi 7080 autoanalyzer. Parameters are as follows: sample: 20 μl of the test solution; R1: 150 μl of [Composition A]; R2: 150 μl of [Composition B]; measurement dominant wavelength: 546 nm; measurement sub-wavelength: 660 nm; Rate A; reaction time: 10 minutes; photometric point: 27-30. Values were calculated by subtracting a value of the test solution at the time of cycle 0 as a blank value.

As shown in FIG. 12, the concentration of the pyrophosphate in the test solution during the nucleic acid amplification reaction by PCR were able to be measured by visible light using the composition of the present invention. The measurement method of the present invention was found to be suitable as a method of easily measuring a nucleic acid based on the level of pyrophosphate production as an index by measurement of the test solution during a nucleic acid amplification reaction by the nucleic acid amplification method. The reaction in the present example was found to be a cycling reaction because the reaction rate increased geometrically with time.

[PCR Mixture]

| x10 buffer for Blend Taq | 10 μl |
|---|---|
| 2 mM dNTPs | 4 μl |
| 2.5 U/μl Blend Taq polymerase | 2 μl |
| 50 μl primer M13Forward | 2 μl |
| 50 μl primer M13Reverse | 2 μl |
| 200 ng/μl Template DNA | 1 μl |
| distilled water | 79 μl |

[Composition A]
100 mM HEPES/NaOH pH 7.0
1 mM PEP
1 mM AMP
1 mM $MgCl_2$
1 U/ml PPDK prepared in Example 7
[Composition B]
100 mM HEPES/NaOH pH 7.0
1 mM β-nicotinamide mononucleotide
1 mM $MgCl_2$
1 mM cholic acid
0.025% nitrotetrazolium blue
0.5 U/ml NMNATase 3-2 prepared in Example 20
5 U/ml 12α-HSD (manufactured by Asahi Kasei Pharma Corporation)
5 U/ml DI (manufactured by Asahi Kasei Pharma Corporation)

Example 25

<Pyrophosphate Measurement 4>

The concentration of pyrophosphate in a test solution during a nucleic acid amplification reaction by PCR was measured. The measurement method is the same as that in Example 24. pUC118/TM0272 obtained in Example 5 was used as a template to amplify the gene of SEQ ID NO: 2.

As shown in FIG. 13, the concentration of the pyrophosphate in the test solution during the nucleic acid amplification reaction by PCR were able to be measured by visible light using the composition of the present invention. The measurement method of the present invention was found to be suitable as a method of easily measuring a nucleic acid based on the level of the pyrophosphate production as an index by measurement of the test solution during a nucleic acid amplification reaction by the nucleic acid amplification method. The reaction in the present example was found to be a cycling reaction because the reaction rate increased geometrically with time.

Example 26

<Improvement of PPDK Expression>

Figure 14:
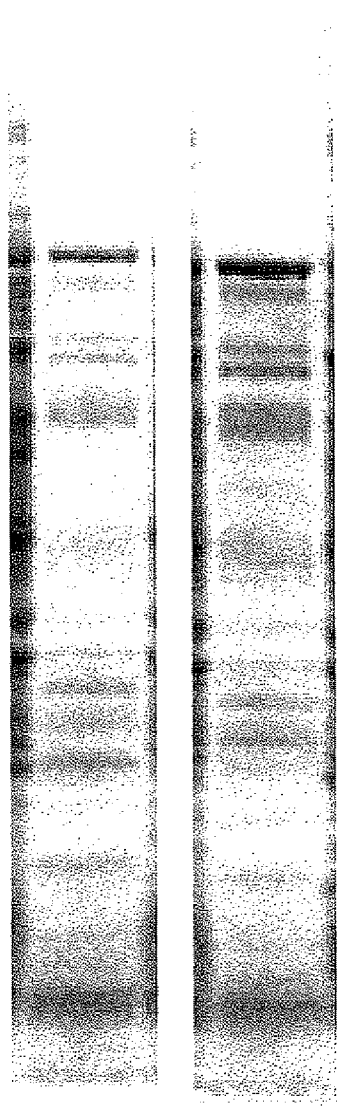
FIG. 14 shows an SDS-PAGE for comparison between the amount of the PPDK expression by the gene of SEQ ID NO: 2 (A) and the amount of the PPDK expression by the gene of SEQ ID NO: 3 (B).

The gene of SEQ ID NO: 3 was prepared by converting codons (AGA, AGG, ATA, CGG, CCC, and CUA) in the gene of SEQ ID NO: 1, which were presumed to be used in *Escherichia coli* with low frequency, into codons which were used with high frequency. Conversion of the codons was performed by PCR using synthetic primers in accordance with a conventional method. Crudely purified solutions were prepared in the same way as in Examples 2, 3, 5, and 6, and SDS-PAGE (FIG. 14) was performed to compare the level of the PPDK expression by the gene of SEQ ID NO: 2 ((A) in FIG. 14) and the level of the PPDK expression by the gene of SEQ ID NO: 3 ((B) in FIG. 14). The level of the PPDK expression by the gene of SEQ ID NO: 3 was found to be higher than the level of the PPDK expression by the gene of SEQ ID NO: 2. The culture titer of the PPDK expressed by the gene of SEQ ID NO: 3 was found to be about three times as high as the culture titer of the PPDK expressed by the gene of SEQ ID NO: 2.

Example 27

<Comparison with Real-Time PCR>

Nucleic acid amplification by PCR was detected by fluorescence using SYBR (registered trademark) Green I and by visible light using the method of measuring the concentration of pyrophosphate of the present invention, and the results were compared.

The following [PCR mixture] was prepared to perform the PCR using SYBR (registered trademark) Premix Ex Taq (registered trademark) (TAKARA BIO INC.). pUC119 including about 220 bp of a fragment was used as a template. In the PCR using SYBR (registered trademark) Green I, fluorescence was detected by real-time PCR using Smart cycler (registered trademark) II System (TAKARA BIO INC.). In usual PCR, Applied Biosystems 9800 Fast thermal cycler was used. At the time of each cycle number, part of [PCR mixture] was withdrawn as a test solution, and detection was performed by visible light using the following [Compositions] by the method of measuring the concentration of pyrophosphate of the present invention using the Hitachi 7080 autoanalyzer. PCR was performed according to the standard protocol of Smart cycler (registered trademark) II System described in the instructions of SYBR (registered trademark) Premix Ex Taq (registered trademark), that is, by shuttle PCR under the following conditions: at 95° C. for 10 seconds and 40 cycles of at 95° C. for 5 seconds and at 60° C. for 20 seconds. PCR conditions in the case of using Applied Biosystems 9800 Fast thermal cycler were the same as above. Parameters of the Hitachi 7080 autoanalyzer are as follows: sample: 20 μl of the test sample; R1: 100 μl of [Composition A]; R2: 50 μl of [Composition B]; measurement dominant wavelength: 546 nm; measurement sub-wavelength: 660 nm; Rate A; reaction time: 10 minutes; photometric point: 23-21. Values were calculated by subtracting a value of the test solution at the time of cycle 0 as a blank value.

The results are shown in FIG. 15. In FIG. 15, the mark "●" shows the results of the detection of nucleic acid amplification by real-time PCR using Smart cycler (registered trademark) II System (TAKARA BIO INC.), while the mark "○" shows the results of the detection of nucleic acid amplification using the composition for measurement of the concentration of pyrophosphate of the present invention and the method of measuring the concentration of pyrophosphate of the present invention. In the real-time PCR, the nucleic acid amplification were able to be detected at about cycle 15, while in the measurement method of the present invention, the nucleic acid amplification were able to be detected at about cycle 17. As described above, the measurement method of the present invention was able to detect the nucleic acid amplification at about the same time as the conventional real-time PCR. Moreover, the measurement method of the present invention was performed by visible light based on the level of pyrophosphate production as an index, and the method measured a nucleic acid more easily than the real-time PCR and was found to be a preferable measurement method. The reaction in the present example was found to be a cycling reaction because the reaction rate increased geometrically with time.

[PCR Mixture]
×1 SYBR (registered trademark) Premix Ex Taq (registered trademark)
0.2 μM M13 Forward Primer
0.2 μM M13 Reverce Primer
about 50 ng Template
[Composition A]
150 mM HEPES/NaOH pH 7.0
1.5 mM PEP
1.5 mM AMP
1.5 mM MgCl$_2$
1.5 U/ml PPDK prepared in Example 7
[Composition B]
50 mM HEPES/NaOH pH 7.0
2 mM β-nicotinamide mononucleotide
2 mM MgCl$_2$
2 mM cholic acid
0.05% nitrotetrazolium blue
1 U/ml NMNATase 3-2 prepared in Example 20
10 U/ml 12α-HSD (manufactured by Asahi Kasei Pharma Corporation)
10 U/ml DI (manufactured by Asahi Kasei Pharma Corporation)

Example 28

<Pyrophosphate Measurement 3>

The following [Compositions] were prepared to perform the method of measuring pyrophosphate. Measurement was performed using the Hitachi 7080 autoanalyzer. Parameters are as follows: sample: 20 μl; R1: 150 μl of [Composition A]; R2: 150 μl of [Composition B]; measurement dominant wavelength: 546 nm; measurement sub-wavelength: 660 nm; Rate A; reaction time: 10 minutes; photometric point: 27-30. Values were calculated by subtracting a blank value in the case of purified water. The mark "○" in FIG. 18 shows the measurement results in the case of using 0 to 1 μM of the pyrophosphate as samples, while the mark "●" in FIG. 18 shows the measurement results in the case of using the mixtures obtained by mixing 0 to 2 μM of the pyrophosphate and 0.8 mM of dNTPs at a ratio of 1:1 as samples. In the case of using 0 to 1 μM of the pyrophosphate as samples, the results were Y=11.0X+0.8 and R2=0.998, while in the case of using the mixtures obtained by mixing 0 to 2 μM of the pyrophosphate and 0.8 mM of dNTPs at a ratio of 1:1 as samples, the results were Y=9.84X+8.0 and R2=0.999. As a result, it was found that the pyrophosphate was able to be measured at high accuracy even in the presence of the dNTPs. Myokinase (manufactured by Sigma-Aldrich Corporation) and ADP-HKTII (ADP-dependent hexokinase (manufactured by Asahi Kasei Pharma Corporation)) were added to eliminate ATP and dATP in the samples. P1,P5,-diadenosine-5'-pentaphosphate (Ap5A) was used as a Myokinase inhibitor.

[Composition A]
100 mM HEPES/NaOH pH 7.5
0.2% TX-100
1 mM PEP
1 mM AMP
1 mM MgCl$_2$
10 mM glucose
2 U/ml ADP-HKTII
3 U/ml Myokinase
[Composition B]
100 mM HEPES/NaOH pH 7.5
1 mM β-nicotinamide mononucleotide
1 mM MgCl$_2$
5 U/ml 12α-HSD
1 mM cholic acid
0.025% nitrotetrazolium blue
0.5 U/ml NMNATase 3-2 prepared in Example 20
5 U/ml DI
0.2% TX-100
1 U/ml PPDK prepared in Example 7
40 μM Ap5A

INDUSTRIAL APPLICABILITY

According to the present invention, there was provided a method of measuring pyrophosphate selectively and easily at high sensitivity.

What is claimed is:

1. A method of determining the concentration of pyrophosphate in a sample, which method comprises the following steps
   (1) a step comprising a first reaction for producing ATP by contacting pyrophosphate which may be present in the sample with pyruvate orthophosphate dikinase in the presence of at least AMP;
   (2) a step comprising a second reaction for producing pyrophosphate and NAD by contacting the ATP produced in the first reaction with nicotinamide-nucleotide adenylyltransferase;
   (3) a step comprising a third reaction for reducing the NAD produced by the second reaction into NADH;
   (4) a step comprising detecting the amount of NADH produced by the third reaction; and
   (5) determining the concentration of pyrophosphate in the sample based on the amount of NADH produced in the above step.

2. The method of selectively measuring pyrophosphate in a sample according to claim 1, wherein step (4) further comprises:
   converting the NADHs produced by the third reaction into a reduced nitroblue tetrazolium salt and NADs in a fourth reaction in the presence of a nitroblue tetrazolium salt; and
   detecting the reduced nitroblue tetrazolium salt produced by the fourth reaction.

3. The method of selectively measuring pyrophosphate in a sample according to claim 2, wherein the NADs produced by the fourth reaction is used in the third reaction to perform a cycling reaction between the third reaction and the fourth reaction.

4. The method of selectively measuring pyrophosphate in a sample according to any one of claims 1 to 3, wherein the pyrophosphate produced by the second reaction is used in the first reaction to perform a cycling reaction between the first reaction and the second reaction.

5. The method of selectively measuring pyrophosphate in a sample according to claim 1, wherein the sample contains triphosphorylated deoxyribonucleic acids (dNTPs).

6. The method of selectively measuring pyrophosphate in a sample according to claim 1, wherein the nicotinamide-nucleotide adenylyltransferase is any of the following enzymes [1] to [3]:
   [1] an enzyme which has an amino acid sequence of SEQ ID NO: 6 and may catalyze the second reaction;
   [2] an enzyme which has the amino acid sequence of SEQ ID NO: 6 with deletion, substitution, or addition of one or several amino acids and may catalyze the second reaction; and

[3] an enzyme which has a substrate specificity ratio for dNTPs and ATP (substrate specificity for dNTPs/substrate specificity for ATP) of 5% or less and may catalyze the second reaction.

7. A method of detecting or quantifying a nucleic acid, comprising measuring, by the method according to claim 1, pyrophosphate in a sample subjected to nucleic acid amplification or a sample prepared from the sample.

8. A method for detecting or quantifying a nucleic acid, said method comprising measuring, by the method according to claim 1, pyrophosphate in a sample subjected to nucleic acid amplification or a sample prepared from the sample by using a composition comprising at least the following components (1) to (7):
   (1) a metal ion;
   (2) AMP;
   (3) phosphoenolpyruvate;
   (4) pyruvate orthophosphate dikinase;
   (5) β-nicotinamide mononucleotides;
   (6) nicotinamide-nucleotide adenylyltransferase; and
   (7) a reduced NAD substance.

9. A method for detecting or quantifying a nucleic acid, said method comprising measuring by the method according to claim 1, pyrophosphate in a sample subjected to nucleic acid amplification or a sample prepared from the sample by using a composition comprising the following two reagents (A) and (B):
   (A) a first reagent containing at least the following components (1) to (4):
      (1) a metal ion;
      (2) AMP;
      (3) phosphoenolpyruvate; and
      (4) pyruvate orthophosphate dikinase;
   (B) a second reagent containing at least the following components (5) to (7):
      (5) β-nicotinamide mononucleotides;
      (6) nicotinamide-nucleotide adenylyltransferase; and
      (7) a reduced NAD substance.

10. The method according to claim 1, wherein the sample is a biological fluid.

11. The method according to claim 10, wherein the biological fluid is selected from the group consisting of synovial fluid, whole blood, plasma, serum, hemocyte, spinal fluid, lymph, urine and extracts thereof.

12. The method according to claim 1, wherein the sample is selected from the group consisting of seawater, natural water, fruit juice, and waste fluid.

13. The method according to claim 1, wherein the pyruvate orthophosphate dikinase is obtained from *Thermotoga maritima*.

14. The method according to claim 1, wherein the nicotinamide-nucleotide adenylyltransferase is obtained from yeast.

15. The method according to claim 6, wherein the nicotinamide-nucleotide adenylyltransferase comprises SEQ ID NO: 6.

16. The method according to claim 6, wherein the nicotinamide-nucleotide adenylyltransferase comprises an enzyme comprising a substrate specificity ratio for dNTPs and ATP (substrate specificity for dNTPs/substrate specificity for ATP) of 5% or less.

17. The method according to claim 8, wherein the metal ion is magnesium.

18. The method according to claim 1, wherein in step (5) the amount of NADH produced in step (4) is compared with a reference value.

19. The method according to claim 1, wherein step (5) further comprises
   determining the concentration of pyrophosphate in the sample by comparing the amount of NADH determined in step (4) with an amount of NADH obtained by steps (1)-(4) from a control sample comprising a known concentration of pyrophosphate, thereby selectively measuring pyrophosphate in the sample.

* * * * *

SEQUENCE LISTING

<160> NUMBER OF SEQ ID NOS: 14

<210> SEQ ID NO 1
<211> LENGTH: 881
<212> TYPE: PRT
<213> ORGANISM: Thermotoga maritime DSM 3109

<400> SEQUENCE: 1

Met Ala Lys Lys Tyr Val Tyr Phe Phe Ala Asn Gly Lys Ala Glu Gly
1               5                   10                  15

Arg Ala Asp Met Lys Asp Ile Leu Gly Gly Lys Gly Ala Asn Leu Ala
            20                  25                  30

Glu Met Thr Asn Leu Gly Ile Pro Val Pro Pro Gly Phe Thr Ile Ser
        35                  40                  45

Ala Glu Val Cys Lys Tyr Tyr Tyr Asp His Gly Arg Thr Tyr Pro Glu
    50                  55                  60

Glu Leu Lys Glu Gln Val Glu Glu Ala Met Arg Arg Leu Glu Glu Val
65                  70                  75                  80

-continued

```
Thr Gly Lys Lys Phe Gly Asp Pro Asn Asn Pro Leu Leu Val Ser Val
                85                  90                  95
Arg Ser Gly Ala Ala Ile Ser Met Pro Gly Met Met Asp Thr Val Leu
            100                 105                 110
Asn Leu Gly Leu Asn Asp Glu Thr Val Lys Gly Leu Ala Lys Leu Thr
            115                 120                 125
Asn Asn Glu Arg Phe Ala Tyr Asp Ala Tyr Arg Arg Phe Leu Gln Met
130                 135                 140
Phe Gly Asp Val Val Leu Lys Ile Pro His Glu Lys Phe Glu Lys Ala
145                 150                 155                 160
Leu Glu Glu Leu Lys Lys Glu Lys Gly Val Lys Leu Asp Thr Glu Leu
                165                 170                 175
Asp Ala Glu Asp Leu Lys Lys Leu Val Glu Arg Tyr Lys Gln Ile Tyr
            180                 185                 190
Lys Glu Glu Gly Lys Glu Phe Pro Gln Asp Pro Trp Lys Gln Leu Trp
            195                 200                 205
Leu Ala Ile Asp Ala Val Phe Gly Ser Trp Met Asn Glu Arg Ala Ile
210                 215                 220
Lys Tyr Arg Gln Ile His Gly Ile Lys Glu Gly Asp Leu Leu Gly Thr
225                 230                 235                 240
Ala Val Asn Ile Val Ala Met Val Phe Gly Asn Met Gly Glu Asp Ser
                245                 250                 255
Gly Thr Gly Val Ala Phe Thr Arg Asp Pro Asn Thr Gly Glu Lys Lys
            260                 265                 270
Pro Tyr Gly Glu Phe Leu Pro Asn Ala Gln Gly Glu Asp Val Val Ala
            275                 280                 285
Gly Ile Arg Thr Pro Leu Lys Leu Glu Glu Leu Lys Asn Arg Met Pro
290                 295                 300
Glu Val Tyr Asn Gln Leu Leu Glu Ile Met Asp Lys Leu Glu Lys His
305                 310                 315                 320
Tyr Arg Asp Met Gln Asp Ile Glu Phe Thr Val Glu Arg Gly Lys Leu
                325                 330                 335
Tyr Ile Leu Gln Thr Arg Asn Gly Lys Arg Thr Ser Gln Ala Ala Ile
            340                 345                 350
Arg Ile Ala Val Asp Met Val His Glu Gly Leu Ile Thr Lys Glu Glu
            355                 360                 365
Ala Ile Leu Arg Val Arg Pro Glu Asp Val Glu Gln Val Leu His Pro
370                 375                 380
Val Phe Asp Pro Lys Glu Lys Ala Gln Ala Lys Val Ile Ala Lys Gly
385                 390                 395                 400
Leu Pro Ala Ser Pro Gly Ala Ala Thr Gly Lys Val Val Phe Asn Ala
                405                 410                 415
Lys Lys Ala Glu Glu Leu Gly Lys Ala Gly Glu Gln Val Ile Leu Val
            420                 425                 430
Arg Pro Glu Thr Ser Pro Glu Asp Val Gly Gly Met Ala Ala Ala Gln
            435                 440                 445
Gly Ile Leu Thr Ser Arg Gly Gly Met Thr Ser His Ala Ala Val Val
450                 455                 460
Ala Arg Gly Met Gly Lys Pro Ala Val Val Gly Ala Glu Ser Ile Glu
465                 470                 475                 480
Val His Pro Glu Glu Gly Tyr Phe Lys Val Gly Asp Val Val Val Lys
                485                 490                 495
Glu Gly Glu Trp Ile Ser Ile Asp Gly Thr Thr Gly Glu Val Leu Leu
```

```
                500             505             510
Gly Lys Val Thr Thr Ile Lys Pro Gln Gly Leu Glu Gly Pro Val Ala
            515                 520                 525

Glu Leu Leu Gln Trp Ala Asp Glu Ile Arg Arg Leu Gly Val Arg Thr
        530                 535                 540

Asn Ala Asp Ile Pro Arg Asp Ala Glu Val Ala Arg Lys Phe Gly Ala
545                 550                 555                 560

Glu Gly Ile Gly Leu Cys Arg Thr Glu His Met Phe Phe Glu Lys Asp
                565                 570                 575

Arg Ile Pro Lys Val Arg Arg Met Ile Leu Ala Lys Thr Lys Glu Glu
            580                 585                 590

Arg Glu Lys Ala Leu Asp Glu Leu Leu Pro Leu Gln Lys Glu Asp Phe
        595                 600                 605

Lys Gly Leu Phe Arg Val Met Lys Gly Leu Pro Val Thr Ile Arg Leu
        610                 615                 620

Ile Asp Pro Pro Leu His Glu Phe Leu Pro Gln Glu Asp Glu Gln Ile
625                 630                 635                 640

Lys Glu Val Ala Glu Gln Met Gly Val Ser Phe Glu Glu Leu Lys Asn
                645                 650                 655

Val Val Glu Asn Leu Lys Glu Leu Asn Pro Met Leu Gly His Arg Gly
            660                 665                 670

Cys Arg Leu Thr Ile Thr Tyr Pro Glu Ile Ala Val Met Gln Thr Lys
        675                 680                 685

Ala Ile Ile Gly Ala Ala Ile Glu Leu Lys Lys Glu Glu Gly Ile Asp
        690                 695                 700

Val Ile Pro Glu Ile Met Ile Pro Leu Val Gly His Val Asn Glu Leu
705                 710                 715                 720

Arg Tyr Leu Lys Lys Ile Ile Lys Glu Thr Ala Asp Ala Leu Ile Lys
                725                 730                 735

Glu Ala Gly Val Glu Leu Thr Tyr Lys Ile Gly Thr Met Ile Glu Val
            740                 745                 750

Pro Arg Ala Ala Val Thr Ala His Gln Ile Ala Glu Glu Ala Glu Phe
        755                 760                 765

Phe Ser Phe Gly Thr Asn Asp Leu Thr Gln Met Thr Phe Gly Phe Ser
        770                 775                 780

Arg Asp Asp Val Gly Lys Phe Leu Pro Glu Tyr Leu Glu Lys Gly Ile
785                 790                 795                 800

Leu Glu His Asp Pro Phe Lys Thr Leu Asp Tyr Asp Gly Val Gly Glu
                805                 810                 815

Leu Val Arg Met Gly Lys Glu Lys Gly Arg Ser Thr Arg Pro Asp Leu
            820                 825                 830

Lys Val Gly Val Cys Gly Glu His Gly Gly Asp Pro Arg Ser Ile Leu
        835                 840                 845

Phe Phe Asp Lys Ile Gly Leu Asp Tyr Val Ser Cys Ser Pro Tyr Arg
        850                 855                 860

Val Pro Val Ala Arg Leu Ala Ala Ala Gln Ala Ala Leu Lys Asn Lys
865                 870                 875                 880

Lys

<210> SEQ ID NO 2
<211> LENGTH: 2646
<212> TYPE: DNA
<213> ORGANISM: Thermotoga maritime DSM 3109
<220> FEATURE:
<221> NAME/KEY: CDS
```

<222> LOCATION: (0001)..(2646)

<400> SEQUENCE: 2

| | | | | | | | | | | | | | | | | |
|---|---|---|---|---|---|---|---|---|---|---|---|---|---|---|---|---|
| atg | gca | aag | aaa | tac | gtg | tac | ttc | ttc | gca | aac | ggt | aag | gca | gaa | ggc | 48 |
| Met | Ala | Lys | Lys | Tyr | Val | Tyr | Phe | Phe | Ala | Asn | Gly | Lys | Ala | Glu | Gly | |
| 1 | | | | 5 | | | | | 10 | | | | | 15 | | |
| cga | gcg | gac | atg | aaa | gat | atc | ctc | ggt | gga | aaa | ggt | gcc | aac | ctc | gca | 96 |
| Arg | Ala | Asp | Met | Lys | Asp | Ile | Leu | Gly | Gly | Lys | Gly | Ala | Asn | Leu | Ala | |
| | | | 20 | | | | | 25 | | | | | 30 | | | |
| gag | atg | acc | aac | ctt | gga | att | cct | gtt | cct | ccc | gga | ttc | acc | att | tcc | 144 |
| Glu | Met | Thr | Asn | Leu | Gly | Ile | Pro | Val | Pro | Pro | Gly | Phe | Thr | Ile | Ser | |
| | | 35 | | | | | 40 | | | | | 45 | | | | |
| gca | gag | gtc | tgt | aag | tac | tac | tac | gac | cac | gga | aga | act | tat | cca | gaa | 192 |
| Ala | Glu | Val | Cys | Lys | Tyr | Tyr | Tyr | Asp | His | Gly | Arg | Thr | Tyr | Pro | Glu | |
| 50 | | | | | 55 | | | | | 60 | | | | | | |
| gaa | ctg | aaa | gaa | cag | gtt | gaa | gag | gca | atg | agg | aga | ctc | gag | gag | gtt | 240 |
| Glu | Leu | Lys | Glu | Gln | Val | Glu | Glu | Ala | Met | Arg | Arg | Leu | Glu | Glu | Val | |
| 65 | | | | | 70 | | | | | 75 | | | | | 80 | |
| act | gga | aaa | aag | ttc | ggt | gac | ccc | aac | aat | cca | ctc | ctt | gtt | tcc | gtc | 288 |
| Thr | Gly | Lys | Lys | Phe | Gly | Asp | Pro | Asn | Asn | Pro | Leu | Leu | Val | Ser | Val | |
| | | | | 85 | | | | | 90 | | | | | 95 | | |
| aga | tct | ggt | gca | gcc | att | tca | atg | cct | gga | atg | atg | gac | acc | gtt | ctc | 336 |
| Arg | Ser | Gly | Ala | Ala | Ile | Ser | Met | Pro | Gly | Met | Met | Asp | Thr | Val | Leu | |
| | | | 100 | | | | | 105 | | | | | 110 | | | |
| aat | ctt | ggt | ctc | aac | gat | gag | aca | gtg | aaa | gga | tta | gca | aag | ctg | acg | 384 |
| Asn | Leu | Gly | Leu | Asn | Asp | Glu | Thr | Val | Lys | Gly | Leu | Ala | Lys | Leu | Thr | |
| | | 115 | | | | | 120 | | | | | 125 | | | | |
| aac | aac | gaa | agg | ttt | gcc | tac | gac | gct | tac | aga | aga | ttc | ctt | cag | atg | 432 |
| Asn | Asn | Glu | Arg | Phe | Ala | Tyr | Asp | Ala | Tyr | Arg | Arg | Phe | Leu | Gln | Met | |
| | 130 | | | | | 135 | | | | | 140 | | | | | |
| ttt | ggt | gat | gtg | gtt | ctg | aag | ata | cct | cac | gag | aaa | ttc | gaa | aag | gca | 480 |
| Phe | Gly | Asp | Val | Val | Leu | Lys | Ile | Pro | His | Glu | Lys | Phe | Glu | Lys | Ala | |
| 145 | | | | | 150 | | | | | 155 | | | | | 160 | |
| ctc | gaa | gaa | ctc | aag | aag | gaa | aaa | ggt | gtg | aaa | ctc | gac | acc | gaa | ctg | 528 |
| Leu | Glu | Glu | Leu | Lys | Lys | Glu | Lys | Gly | Val | Lys | Leu | Asp | Thr | Glu | Leu | |
| | | | | 165 | | | | | 170 | | | | | 175 | | |
| gat | gca | gaa | gac | ctc | aaa | aaa | ctc | gtt | gaa | aga | tac | aaa | cag | atc | tac | 576 |
| Asp | Ala | Glu | Asp | Leu | Lys | Lys | Leu | Val | Glu | Arg | Tyr | Lys | Gln | Ile | Tyr | |
| | | | 180 | | | | | 185 | | | | | 190 | | | |
| aag | gaa | gag | gga | aaa | gaa | ttt | ccg | cag | gat | ccc | tgg | aaa | cag | ctc | tgg | 624 |
| Lys | Glu | Glu | Gly | Lys | Glu | Phe | Pro | Gln | Asp | Pro | Trp | Lys | Gln | Leu | Trp | |
| | | 195 | | | | | 200 | | | | | 205 | | | | |
| ctt | gcg | atc | gat | gcg | gtg | ttc | ggt | agc | tgg | atg | aac | gag | aga | gct | atc | 672 |
| Leu | Ala | Ile | Asp | Ala | Val | Phe | Gly | Ser | Trp | Met | Asn | Glu | Arg | Ala | Ile | |
| | 210 | | | | | 215 | | | | | 220 | | | | | |
| aag | tac | agg | cag | att | cac | gga | atc | aag | gaa | gga | gat | ctc | ctc | ggt | acg | 720 |
| Lys | Tyr | Arg | Gln | Ile | His | Gly | Ile | Lys | Glu | Gly | Asp | Leu | Leu | Gly | Thr | |
| 225 | | | | | 230 | | | | | 235 | | | | | 240 | |
| gcc | gtg | aac | atc | gtc | gcg | atg | gtg | ttt | gga | aac | atg | gga | gaa | gac | tcc | 768 |
| Ala | Val | Asn | Ile | Val | Ala | Met | Val | Phe | Gly | Asn | Met | Gly | Glu | Asp | Ser | |
| | | | | 245 | | | | | 250 | | | | | 255 | | |
| gga | acg | ggt | gtc | gcc | ttc | aca | aga | gac | ccg | aac | act | gga | gag | aag | aaa | 816 |
| Gly | Thr | Gly | Val | Ala | Phe | Thr | Arg | Asp | Pro | Asn | Thr | Gly | Glu | Lys | Lys | |
| | | | 260 | | | | | 265 | | | | | 270 | | | |
| cct | tac | gga | gag | ttc | ctg | ccc | aat | gct | cag | ggt | gag | gac | gtt | gtt | gcg | 864 |
| Pro | Tyr | Gly | Glu | Phe | Leu | Pro | Asn | Ala | Gln | Gly | Glu | Asp | Val | Val | Ala | |
| | | 275 | | | | | 280 | | | | | 285 | | | | |
| ggt | atc | aga | act | cct | ctc | aaa | ctt | gaa | gag | ttg | aaa | aac | aga | atg | cca | 912 |
| Gly | Ile | Arg | Thr | Pro | Leu | Lys | Leu | Glu | Glu | Leu | Lys | Asn | Arg | Met | Pro | |
| | 290 | | | | | 295 | | | | | 300 | | | | | |

```
-continued gag gtc tac aat cag ctc ctt gaa ata atg gac aaa ctg gaa aaa cac    960
Glu Val Tyr Asn Gln Leu Leu Glu Ile Met Asp Lys Leu Glu Lys His
305                 310                 315                 320 tac aga gat atg cag gac atc gag ttc acc gtt gag aga gga aag ctc   1008
Tyr Arg Asp Met Gln Asp Ile Glu Phe Thr Val Glu Arg Gly Lys Leu
            325                 330                 335 tac atc ttg cag aca aga aat gga aag aga acc tct cag gca gct atc   1056
Tyr Ile Leu Gln Thr Arg Asn Gly Lys Arg Thr Ser Gln Ala Ala Ile
        340                 345                 350 agg atc gcc gtt gac atg gtc cac gaa gga ctc atc acc aaa gag gaa   1104
Arg Ile Ala Val Asp Met Val His Glu Gly Leu Ile Thr Lys Glu Glu
    355                 360                 365 gct att ctc aga gtg aga cct gaa gac gtc gaa cag gtg ctt cat cct   1152
Ala Ile Leu Arg Val Arg Pro Glu Asp Val Glu Gln Val Leu His Pro
370                 375                 380 gtg ttc gat cca aaa gaa aag gcc cag gca aaa gtc atc gcg aaa ggg   1200
Val Phe Asp Pro Lys Glu Lys Ala Gln Ala Lys Val Ile Ala Lys Gly
385                 390                 395                 400 ctt cct gca tct cca ggt gcc gca acg ggt aag gtc gtc ttc aac gcg   1248
Leu Pro Ala Ser Pro Gly Ala Ala Thr Gly Lys Val Val Phe Asn Ala
            405                 410                 415 aag aaa gct gag gag ctc ggc aaa gca ggt gaa cag gtc att ctt gtg   1296
Lys Lys Ala Glu Glu Leu Gly Lys Ala Gly Glu Gln Val Ile Leu Val
        420                 425                 430 aga cct gaa acc agc ccc gaa gac gtt gga gga atg gcc gct gcg cag   1344
Arg Pro Glu Thr Ser Pro Glu Asp Val Gly Gly Met Ala Ala Ala Gln
    435                 440                 445 gga att ttg acc tcc aga ggg gga atg acc tct cac gct gcc gtt gtc   1392
Gly Ile Leu Thr Ser Arg Gly Gly Met Thr Ser His Ala Ala Val Val
450                 455                 460 gca aga gga atg ggt aag cca gca gtc gtc gga gca gaa tcc ata gaa   1440
Ala Arg Gly Met Gly Lys Pro Ala Val Val Gly Ala Glu Ser Ile Glu
465                 470                 475                 480 gtc cat cct gag gaa ggt tac ttc aaa gtg gga gac gtc gtt gta aaa   1488
Val His Pro Glu Glu Gly Tyr Phe Lys Val Gly Asp Val Val Val Lys
            485                 490                 495 gaa gga gaa tgg atc tcc atc gat ggg act acc ggt gag gtc ctc ctt   1536
Glu Gly Glu Trp Ile Ser Ile Asp Gly Thr Thr Gly Glu Val Leu Leu
        500                 505                 510 gga aaa gta aca aca ata aaa cca cag ggc ctt gaa gga cct gtc gcg   1584
Gly Lys Val Thr Thr Ile Lys Pro Gln Gly Leu Glu Gly Pro Val Ala
    515                 520                 525 gag ctt ctg cag tgg gcc gat gag atc aga aga ctc ggt gtg aga acc   1632
Glu Leu Leu Gln Trp Ala Asp Glu Ile Arg Arg Leu Gly Val Arg Thr
530                 535                 540 aac gca gac ata ccg aga gac gcg gaa gtc gcg aga aaa ttc ggt gct   1680
Asn Ala Asp Ile Pro Arg Asp Ala Glu Val Ala Arg Lys Phe Gly Ala
545                 550                 555                 560 gaa gga atc ggg ctc tgt aga aca gaa cac atg ttc ttc gaa aag gac   1728
Glu Gly Ile Gly Leu Cys Arg Thr Glu His Met Phe Phe Glu Lys Asp
            565                 570                 575 aga ata ccc aag gtt aga agg atg atc ctc gca aag aca aaa gaa gaa   1776
Arg Ile Pro Lys Val Arg Arg Met Ile Leu Ala Lys Thr Lys Glu Glu
        580                 585                 590 aga gaa aag gct ctg gac gaa ctt ctg cca ctt cag aaa gag gac ttc   1824
Arg Glu Lys Ala Leu Asp Glu Leu Leu Pro Leu Gln Lys Glu Asp Phe
    595                 600                 605 aag gga ttg ttc aga gtg atg aaa gga ctt cca gtc acc ata agg ctc   1872
Lys Gly Leu Phe Arg Val Met Lys Gly Leu Pro Val Thr Ile Arg Leu
610                 615                 620
```

```
ata gat cct cct ctc cat gaa ttc ctg ccg caa gaa gat gaa cag atc    1920
Ile Asp Pro Pro Leu His Glu Phe Leu Pro Gln Glu Asp Glu Gln Ile
625                 630                 635                 640 aag gaa gtt gcc gag cag atg gga gtc tcc ttt gag gaa ctc aag aac    1968
Lys Glu Val Ala Glu Gln Met Gly Val Ser Phe Glu Glu Leu Lys Asn
            645                 650                 655 gtc gtg gag aat ctc aaa gaa ctc aac cca atg ctc ggg cac aga ggt    2016
Val Val Glu Asn Leu Lys Glu Leu Asn Pro Met Leu Gly His Arg Gly
        660                 665                 670 tgt agg ctc acc atc acc tat cct gag atc gct gtg atg cag acc aaa    2064
Cys Arg Leu Thr Ile Thr Tyr Pro Glu Ile Ala Val Met Gln Thr Lys
    675                 680                 685 gca ata att gga gcg gcc atc gaa ctc aag aaa gag gaa gga ata gat    2112
Ala Ile Ile Gly Ala Ala Ile Glu Leu Lys Lys Glu Glu Gly Ile Asp
690                 695                 700 gta ata cct gaa atc atg att cct ctt gtg gga cac gtt aac gaa ctc    2160
Val Ile Pro Glu Ile Met Ile Pro Leu Val Gly His Val Asn Glu Leu
705                 710                 715                 720 agg tac ctg aag aag atc atc aag gaa acg gcc gac gct ctc ata aaa    2208
Arg Tyr Leu Lys Lys Ile Ile Lys Glu Thr Ala Asp Ala Leu Ile Lys
            725                 730                 735 gaa gct ggt gtc gag ctc act tac aag atc gga acc atg att gaa gtt    2256
Glu Ala Gly Val Glu Leu Thr Tyr Lys Ile Gly Thr Met Ile Glu Val
        740                 745                 750 cca agg gcc gct gtt acc gcc cat cag ata gcg gaa gaa gca gaa ttc    2304
Pro Arg Ala Ala Val Thr Ala His Gln Ile Ala Glu Glu Ala Glu Phe
    755                 760                 765 ttc agc ttc ggt act aac gac ctc aca cag atg acc ttt gga ttc agc    2352
Phe Ser Phe Gly Thr Asn Asp Leu Thr Gln Met Thr Phe Gly Phe Ser
770                 775                 780 cga gac gac gtt gga aag ttc ctg cct gag tac ctt gaa aag ggc atc    2400
Arg Asp Asp Val Gly Lys Phe Leu Pro Glu Tyr Leu Glu Lys Gly Ile
785                 790                 795                 800 ctc gaa cac gat cca ttc aag acg ctg gac tac gac ggt gtt gga gaa    2448
Leu Glu His Asp Pro Phe Lys Thr Leu Asp Tyr Asp Gly Val Gly Glu
            805                 810                 815 ctg gtg agg atg ggt aaa gag aaa gga aga agc aca agg ccc gat ctc    2496
Leu Val Arg Met Gly Lys Glu Lys Gly Arg Ser Thr Arg Pro Asp Leu
        820                 825                 830 aaa gtt gga gtc tgt gga gaa cac ggt gga gat ccg aga tcc ata ctg    2544
Lys Val Gly Val Cys Gly Glu His Gly Gly Asp Pro Arg Ser Ile Leu
    835                 840                 845 ttc ttc gac aaa att gga ctc gac tac gtt tcc tgt tcg ccg tac aga    2592
Phe Phe Asp Lys Ile Gly Leu Asp Tyr Val Ser Cys Ser Pro Tyr Arg
850                 855                 860 gta cct gtt gcc aga ctt gca gcg gct cag gca gct ctc aaa aac aag    2640
Val Pro Val Ala Arg Leu Ala Ala Ala Gln Ala Ala Leu Lys Asn Lys
865                 870                 875                 880 aaa taa                                                             2646
Lys

<210> SEQ ID NO 3
<211> LENGTH: 2646
<212> TYPE: DNA
<213> ORGANISM: Thermotoga maritime DSM 3109
<220> FEATURE:
<221> NAME/KEY: CDS
<222> LOCATION: (0001)..(2646)

<400> SEQUENCE: 3 atg gca aag aaa tac gtg tac ttc ttc gca aac ggt aag gca gaa ggc    48
Met Ala Lys Lys Tyr Val Tyr Phe Phe Ala Asn Gly Lys Ala Glu Gly
```

```
     1               5                  10                 15 cgt gcg gac atg aaa gat atc ctc ggt gga aaa ggt gcc aac ctc gca      96
Arg Ala Asp Met Lys Asp Ile Leu Gly Gly Lys Gly Ala Asn Leu Ala
             20                  25                  30 gag atg acc aac ctt gga att cct gtt cct ccg gga ttc acc att tcc     144
Glu Met Thr Asn Leu Gly Ile Pro Val Pro Pro Gly Phe Thr Ile Ser
         35                  40                  45 gca gag gtc tgt aag tac tac tac gac cac gga cgt act tat cca gaa     192
Ala Glu Val Cys Lys Tyr Tyr Tyr Asp His Gly Arg Thr Tyr Pro Glu
     50                  55                  60 gaa ctg aaa gaa cag gtt gaa gag gca atg cgc cgt ctc gaa gag gtt     240
Glu Leu Lys Glu Gln Val Glu Glu Ala Met Arg Arg Leu Glu Glu Val
 65                  70                  75                  80 act gga aaa aag ttc ggt gac ccg aac aat cca ctc ctt gtt tcc gtc     288
Thr Gly Lys Lys Phe Gly Asp Pro Asn Asn Pro Leu Leu Val Ser Val
                 85                  90                  95 cgt tct ggt gca gcc att tca atg cct gga atg atg gac acc gtt ctc     336
Arg Ser Gly Ala Ala Ile Ser Met Pro Gly Met Met Asp Thr Val Leu
             100                 105                 110 aat ctt ggt ctc aac gat gag aca gtg aaa gga tta gca aag ctg acg     384
Asn Leu Gly Leu Asn Asp Glu Thr Val Lys Gly Leu Ala Lys Leu Thr
         115                 120                 125 aac aac gaa cgt ttt gcc tac gac gct tac cgc cgt ttc ctt cag atg     432
Asn Asn Glu Arg Phe Ala Tyr Asp Ala Tyr Arg Arg Phe Leu Gln Met
     130                 135                 140 ttt ggt gat gtg gtt ctg aag att cct cac gag aaa ttt gaa aag gca     480
Phe Gly Asp Val Val Leu Lys Ile Pro His Glu Lys Phe Glu Lys Ala
145                 150                 155                 160 ctc gaa gaa ctc aag aag gaa aaa ggt gtg aaa ctc gac acc gaa ctg     528
Leu Glu Glu Leu Lys Lys Glu Lys Gly Val Lys Leu Asp Thr Glu Leu
                 165                 170                 175 gat gca gaa gac ctc aaa aaa ctc gtt gaa cgt tac aaa cag atc tac     576
Asp Ala Glu Asp Leu Lys Lys Leu Val Glu Arg Tyr Lys Gln Ile Tyr
             180                 185                 190 aag gaa gag gga aaa gaa ttt ccg cag gat ccg tgg aaa cag ctc tgg     624
Lys Glu Glu Gly Lys Glu Phe Pro Gln Asp Pro Trp Lys Gln Leu Trp
         195                 200                 205 ctt gcg atc gat gcg gtg ttc ggt agc tgg atg aac gag cgt gct atc     672
Leu Ala Ile Asp Ala Val Phe Gly Ser Trp Met Asn Glu Arg Ala Ile
     210                 215                 220 aag tac cgt cag att cac gga atc aag gaa gga gat ctc ctc ggt acg     720
Lys Tyr Arg Gln Ile His Gly Ile Lys Glu Gly Asp Leu Leu Gly Thr
225                 230                 235                 240 gcc gtg aac atc gtc gcg atg gtg ttt gga aac atg gga gaa gac tcc     768
Ala Val Asn Ile Val Ala Met Val Phe Gly Asn Met Gly Glu Asp Ser
                 245                 250                 255 gga acg ggt gtc gcc ttc aca cgt gac ccg aac act gga gag aag aaa     816
Gly Thr Gly Val Ala Phe Thr Arg Asp Pro Asn Thr Gly Glu Lys Lys
             260                 265                 270 cct tac gga gag ttc ctg ccg aat gct cag ggt gag gac gtt gtt gcg     864
Pro Tyr Gly Glu Phe Leu Pro Asn Ala Gln Gly Glu Asp Val Val Ala
         275                 280                 285 ggt atc cgt act cct ctc aaa ctt gaa gag ttg aaa aac cgt atg cca     912
Gly Ile Arg Thr Pro Leu Lys Leu Glu Glu Leu Lys Asn Arg Met Pro
     290                 295                 300 gag gtc tac aat cag ctc ctc gag att atg gac aaa ctg gaa aaa cac     960
Glu Val Tyr Asn Gln Leu Leu Glu Ile Met Asp Lys Leu Glu Lys His
305                 310                 315                 320 tac cgc gat atg cag gac atc gag ttc acc gtt gag cgt gga aag ctc    1008
Tyr Arg Asp Met Gln Asp Ile Glu Phe Thr Val Glu Arg Gly Lys Leu
```

-continued

|  |  |  | 325 |  |  |  | 330 |  |  |  | 335 |  |  |
|---|---|---|---|---|---|---|---|---|---|---|---|---|---|
| tac | atc | ttg | cag | aca | cgc | aat | gga | aag | cgt | acc | tct | cag | gca gct atc | 1056 |
| Tyr | Ile | Leu | Gln | Thr | Arg | Asn | Gly | Lys | Arg | Thr | Ser | Gln | Ala Ala Ile |
|  |  |  | 340 |  |  |  | 345 |  |  |  | 350 |  |  |

```
tac atc ttg cag aca cgc aat gga aag cgt acc tct cag gca gct atc    1056
Tyr Ile Leu Gln Thr Arg Asn Gly Lys Arg Thr Ser Gln Ala Ala Ile
            340                 345                 350 cgt atc gcc gtt gac atg gtc cac gaa gga ctc atc acc aaa gag gaa    1104
Arg Ile Ala Val Asp Met Val His Glu Gly Leu Ile Thr Lys Glu Glu
        355                 360                 365 gct att ctc cgc gtg cgt cct gaa gac gtc gaa cag gtg ctt cat cct    1152
Ala Ile Leu Arg Val Arg Pro Glu Asp Val Glu Gln Val Leu His Pro
    370                 375                 380 gtg ttc gat cca aaa gaa aag gcc cag gca aaa gtc atc gcg aaa ggg    1200
Val Phe Asp Pro Lys Glu Lys Ala Gln Ala Lys Val Ile Ala Lys Gly
385                 390                 395                 400 ctt cct gca tct cca ggt gcc gca acg ggt aag gtc gtc ttc aac gcg    1248
Leu Pro Ala Ser Pro Gly Ala Ala Thr Gly Lys Val Val Phe Asn Ala
                405                 410                 415 aag aaa gct gag gag ctc ggc aaa gca ggt gaa cag gtc att ctt gtg    1296
Lys Lys Ala Glu Glu Leu Gly Lys Ala Gly Glu Gln Val Ile Leu Val
            420                 425                 430 cgt cct gaa acc agc ccg gaa gac gtt gga gga atg gcg gct gcg cag    1344
Arg Pro Glu Thr Ser Pro Glu Asp Val Gly Gly Met Ala Ala Ala Gln
        435                 440                 445 gga att ttg acc tcc cgt ggg gga atg acc tct cac gct gcc gtt gtc    1392
Gly Ile Leu Thr Ser Arg Gly Gly Met Thr Ser His Ala Ala Val Val
    450                 455                 460 gca cgt gga atg ggt aag cca gca gtc gtc gga gca gaa tcc att gaa    1440
Ala Arg Gly Met Gly Lys Pro Ala Val Val Gly Ala Glu Ser Ile Glu
465                 470                 475                 480 gtc cat cct gag gaa ggt tac ttc aaa gtg gga gac gtc gtt gta aaa    1488
Val His Pro Glu Glu Gly Tyr Phe Lys Val Gly Asp Val Val Val Lys
                485                 490                 495 gaa gga gaa tgg atc tcc atc gat ggg act acc ggt gag gtc ctc ctt    1536
Glu Gly Glu Trp Ile Ser Ile Asp Gly Thr Thr Gly Glu Val Leu Leu
            500                 505                 510 gga aaa gta aca aca att aaa cca cag ggc ctt gaa gga cct gtc gcg    1584
Gly Lys Val Thr Thr Ile Lys Pro Gln Gly Leu Glu Gly Pro Val Ala
        515                 520                 525 gag ctt ctc cag tgg gcc gat gag atc cgc cgt ctc ggt gtg cgt acc    1632
Glu Leu Leu Gln Trp Ala Asp Glu Ile Arg Arg Leu Gly Val Arg Thr
    530                 535                 540 aac gca gac att ccg cgc gac gcg gaa gtc gcg cgt aaa ttc ggt gct    1680
Asn Ala Asp Ile Pro Arg Asp Ala Glu Val Ala Arg Lys Phe Gly Ala
545                 550                 555                 560 gaa gga atc ggg ctc tgt cgt aca gaa cac atg ttc ttc gaa aag gac    1728
Glu Gly Ile Gly Leu Cys Arg Thr Glu His Met Phe Phe Glu Lys Asp
                565                 570                 575 cgt att ccg aag gtt cgc cgt atg atc ctc gca aag aca aaa gaa gaa    1776
Arg Ile Pro Lys Val Arg Arg Met Ile Leu Ala Lys Thr Lys Glu Glu
            580                 585                 590 cgt gaa aag gct ctg gac gaa ctt ctg cca ctt cag aaa gag gac ttc    1824
Arg Glu Lys Ala Leu Asp Glu Leu Leu Pro Leu Gln Lys Glu Asp Phe
        595                 600                 605 aag gga ttg ttc cgt gtg atg aaa gga ctt cca gtc acc att cgt ctc    1872
Lys Gly Leu Phe Arg Val Met Lys Gly Leu Pro Val Thr Ile Arg Leu
    610                 615                 620 att gat cct cct ctc cat gaa ttc ctg ccg caa gaa gat gaa cag atc    1920
Ile Asp Pro Pro Leu His Glu Phe Leu Pro Gln Glu Asp Glu Gln Ile
625                 630                 635                 640 aag gaa gtt gcc gag cag atg gga gtc tcc ttt gag gaa ctc aag aac    1968
Lys Glu Val Ala Glu Gln Met Gly Val Ser Phe Glu Glu Leu Lys Asn
```

-continued

```
                            645                 650                 655
gtc gtg gag aat ctc aaa gaa ctc aac cca atg ctc ggg cac cgt ggt           2016
Val Val Glu Asn Leu Lys Glu Leu Asn Pro Met Leu Gly His Arg Gly
            660                 665                 670 tgt cgt ctc acc atc acc tat cct gag atc gct gtg atg cag acc aaa           2064
Cys Arg Leu Thr Ile Thr Tyr Pro Glu Ile Ala Val Met Gln Thr Lys
        675                 680                 685 gca att att gga gcg gcc atc gaa ctc aag aaa gag gaa gga att gat           2112
Ala Ile Ile Gly Ala Ala Ile Glu Leu Lys Lys Glu Glu Gly Ile Asp
    690                 695                 700 gta att cct gaa atc atg att cct ctt gtg gga cac gtt aac gaa ctc           2160
Val Ile Pro Glu Ile Met Ile Pro Leu Val Gly His Val Asn Glu Leu
705                 710                 715                 720 cgt tac ctg aag aag atc atc aag gaa acg gcc gac gct ctc att aaa           2208
Arg Tyr Leu Lys Lys Ile Ile Lys Glu Thr Ala Asp Ala Leu Ile Lys
                725                 730                 735 gag gct ggt gtc gag ctc act tac aag atc gga acc atg att gaa gtt           2256
Glu Ala Gly Val Glu Leu Thr Tyr Lys Ile Gly Thr Met Ile Glu Val
            740                 745                 750 cca cgt gcc gct gtt acc gcc cat cag att gcg gaa gaa gca gaa ttc           2304
Pro Arg Ala Ala Val Thr Ala His Gln Ile Ala Glu Glu Ala Glu Phe
        755                 760                 765 ttc agc ttc ggt act aac gac ctc aca cag atg acc ttt gga ttc agc           2352
Phe Ser Phe Gly Thr Asn Asp Leu Thr Gln Met Thr Phe Gly Phe Ser
    770                 775                 780 cgt gac gac gtt gga aag ttc ctg cct gag tac ctt gaa aag ggc atc           2400
Arg Asp Asp Val Gly Lys Phe Leu Pro Glu Tyr Leu Glu Lys Gly Ile
785                 790                 795                 800 ctc gaa cac gat cca ttc aag acg ctg gac tac gac ggt gtt gga gaa           2448
Leu Glu His Asp Pro Phe Lys Thr Leu Asp Tyr Asp Gly Val Gly Glu
                805                 810                 815 ctg gtg cgt atg ggt aaa gag aaa gga cgc agc aca cgt ccg gat ctc           2496
Leu Val Arg Met Gly Lys Glu Lys Gly Arg Ser Thr Arg Pro Asp Leu
            820                 825                 830 aaa gtt gga gtc tgt gga gaa cac ggt gga gat ccg cgt tcc att ctg           2544
Lys Val Gly Val Cys Gly Glu His Gly Gly Asp Pro Arg Ser Ile Leu
        835                 840                 845 ttc ttc gac aaa att gga ctc gac tac gtt tcc tgt tcg ccg tac cgt           2592
Phe Phe Asp Lys Ile Gly Leu Asp Tyr Val Ser Cys Ser Pro Tyr Arg
    850                 855                 860 gta cct gtt gcc cgt ctt gca gcg gct cag gca gct ctc aaa aac aag           2640
Val Pro Val Ala Arg Leu Ala Ala Ala Gln Ala Ala Leu Lys Asn Lys
865                 870                 875                 880 aaa taa                                                                   2646
Lys <210> SEQ ID NO 4
<211> LENGTH: 10
<212> TYPE: PRT
<213> ORGANISM: Unknown
<220> FEATURE:
<223> OTHER INFORMATION: Synthetic peptide

<400> SEQUENCE: 4

Pro Leu Leu Val Ser Val Arg Ser Gly Ala
1               5                   10

<210> SEQ ID NO 5
<211> LENGTH: 13
<212> TYPE: PRT
<213> ORGANISM: Unknown
<220> FEATURE:
```

<223> OTHER INFORMATION: Synthetic peptide

<400> SEQUENCE: 5

Arg Gly Gly Met Thr Ser His Ala Ala Val Val Ala Arg
1               5                   10

<210> SEQ ID NO 6
<211> LENGTH: 395
<212> TYPE: PRT
<213> ORGANISM: Saccharomyces cerevisiae 6-2

<400> SEQUENCE: 6

Met Asp Pro Thr Lys Ala Pro Asp Phe Lys Pro Pro Gln Pro Asn Glu
1               5                   10                  15

Glu Leu Gln Pro Pro Asp Pro Thr His Thr Ile Pro Lys Ser Gly
            20                  25                  30

Pro Ile Val Pro Tyr Val Leu Ala Asp Tyr Asn Ser Ser Ile Asp Ala
        35                  40                  45

Pro Phe Asn Leu Asp Ile Tyr Lys Thr Leu Ser Ser Arg Lys Lys Asn
    50                  55                  60

Ala Asn Ser Ser Asn Arg Met Asp His Ile Pro Leu Asn Thr Ser Asp
65                  70                  75                  80

Phe Gln Pro Leu Ser Arg Asp Val Ser Glu Glu Ser Glu Gly
                85                  90                  95

Gln Ser Asn Gly Ile Asp Ala Thr Leu Gln Asp Val Thr Met Thr Gly
            100                 105                 110

Asn Leu Gly Val Leu Lys Ser Gln Ile Ala Asp Leu Glu Glu Val Pro
        115                 120                 125

His Thr Ile Val Arg Gln Ala Arg Thr Ile Glu Asp Tyr Glu Phe Pro
    130                 135                 140

Val His Arg Leu Thr Lys Lys Leu Gln Asp Pro Glu Lys Leu Pro Leu
145                 150                 155                 160

Ile Ile Val Ala Cys Gly Ser Phe Ser Pro Ile Thr Tyr Leu His Leu
                165                 170                 175

Arg Met Phe Glu Met Ala Leu Asp Asp Ile Asn Glu Gln Thr Arg Phe
            180                 185                 190

Glu Val Val Gly Gly Tyr Phe Ser Pro Val Ser Asp Asn Tyr Gln Lys
        195                 200                 205

Arg Gly Leu Ala Pro Ala Tyr His Arg Val Arg Met Cys Glu Leu Ala
    210                 215                 220

Cys Glu Arg Thr Ser Ser Trp Leu Met Val Asp Ala Trp Glu Ser Leu
225                 230                 235                 240

Gln Ser Ser Tyr Thr Arg Thr Ala Lys Val Leu Asp His Phe Asn His
                245                 250                 255

Glu Ile Asn Ile Lys Arg Gly Gly Ile Met Thr Val Asp Gly Glu Lys
            260                 265                 270

Met Gly Val Lys Ile Met Leu Leu Ala Gly Gly Asp Leu Ile Glu Ser
        275                 280                 285

Met Gly Glu Pro His Val Trp Ala Asp Ser Asp Leu His His Ile Leu
    290                 295                 300

Gly Asn Tyr Gly Cys Leu Ile Val Glu Arg Thr Gly Ser Asp Val Arg
305                 310                 315                 320

Ser Phe Leu Leu Ser His Asp Ile Met Tyr Glu His Arg Arg Asn Ile
                325                 330                 335

Leu Ile Ile Lys Gln Leu Ile Tyr Asn Asp Ile Ser Ser Thr Lys Val
            340                 345                 350

```
Arg Leu Phe Ile Arg Arg Gly Met Ser Val Gln Tyr Leu Leu Pro Asn
        355                 360                 365

Ser Val Ile Arg Tyr Ile Gln Glu Tyr Asn Leu Tyr Ile Asn Gln Ser
        370                 375                 380

Glu Pro Val Lys Gln Val Leu Asp Ser Lys Glu
385                 390                 395

<210> SEQ ID NO 7
<211> LENGTH: 1188
<212> TYPE: DNA
<213> ORGANISM: Saccharomyces cerevisiae 6-2
<220> FEATURE:
<221> NAME/KEY: CDS
<222> LOCATION: (0001)..(1188)

<400> SEQUENCE: 7 atg gat ccc acc aaa gca ccc gat ttt aaa ccg cca cag cca aat gaa      48
Met Asp Pro Thr Lys Ala Pro Asp Phe Lys Pro Pro Gln Pro Asn Glu
1               5                   10                  15 gaa cta caa cca ccg cca gat cca aca cat acg ata cca aaa tct gga      96
Glu Leu Gln Pro Pro Pro Asp Pro Thr His Thr Ile Pro Lys Ser Gly
            20                  25                  30 ccc ata gtt cca tat gtt tta gct gat tat aat tct tcg atc gat gct     144
Pro Ile Val Pro Tyr Val Leu Ala Asp Tyr Asn Ser Ser Ile Asp Ala
        35                  40                  45 cct ttc aat ctc gac att tac aaa acc ctg tcg tca agg aaa aaa aac     192
Pro Phe Asn Leu Asp Ile Tyr Lys Thr Leu Ser Ser Arg Lys Lys Asn
    50                  55                  60 gcc aac tca agc aac cga atg gac cat att cca tta aat act agt gac     240
Ala Asn Ser Ser Asn Arg Met Asp His Ile Pro Leu Asn Thr Ser Asp
65                  70                  75                  80 ttc cag cca cta tct cgg gat gta tca tcg gag gag gaa agt gaa ggg     288
Phe Gln Pro Leu Ser Arg Asp Val Ser Ser Glu Glu Glu Ser Glu Gly
                85                  90                  95 caa tcg aat gga att gac gct act cta cag gat gtt acg atg act ggg     336
Gln Ser Asn Gly Ile Asp Ala Thr Leu Gln Asp Val Thr Met Thr Gly
            100                 105                 110 aat ttg ggg gta ctg aag agc caa att gct gat ttg gaa gaa gtt cct     384
Asn Leu Gly Val Leu Lys Ser Gln Ile Ala Asp Leu Glu Glu Val Pro
        115                 120                 125 cac aca att gta aga caa gcc aga act att gaa gat tac gaa ttt cct     432
His Thr Ile Val Arg Gln Ala Arg Thr Ile Glu Asp Tyr Glu Phe Pro
    130                 135                 140 gta cac aga ttg acg aaa aag tta caa gat cct gaa aaa ctg cct ctg     480
Val His Arg Leu Thr Lys Lys Leu Gln Asp Pro Glu Lys Leu Pro Leu
145                 150                 155                 160 atc atc gtt gct tgt gga tca ttt tct ccc ata aca tac cta cat ttg     528
Ile Ile Val Ala Cys Gly Ser Phe Ser Pro Ile Thr Tyr Leu His Leu
                165                 170                 175 aga atg ttt gaa atg gct tta gat gat atc aat gag caa acg cgt ttt     576
Arg Met Phe Glu Met Ala Leu Asp Asp Ile Asn Glu Gln Thr Arg Phe
            180                 185                 190 gaa gtg gtt ggt ggt tat ttt tct cca gta agt gat aac tat caa aag     624
Glu Val Val Gly Gly Tyr Phe Ser Pro Val Ser Asp Asn Tyr Gln Lys
        195                 200                 205 cga ggg tta gcc cca gct tat cat cgt gtc cgc atg tgc gaa tta gca     672
Arg Gly Leu Ala Pro Ala Tyr His Arg Val Arg Met Cys Glu Leu Ala
    210                 215                 220 tgc gag cgg aca tca tct tgg tta atg gtt gat gcc tgg gaa tct tta     720
Cys Glu Arg Thr Ser Ser Trp Leu Met Val Asp Ala Trp Glu Ser Leu
225                 230                 235                 240
```

```
caa tca agt tat aca agg aca gca aaa gtc ttg gac cat ttc aat cat      768
Gln Ser Ser Tyr Thr Arg Thr Ala Lys Val Leu Asp His Phe Asn His
                245                 250                 255 gaa ata aat atc aag aga ggt gga atc atg act gta gat ggt gaa aaa      816
Glu Ile Asn Ile Lys Arg Gly Gly Ile Met Thr Val Asp Gly Glu Lys
            260                 265                 270 atg ggc gta aaa atc atg tta ttg gca ggc ggt gat ctt atc gaa tcc      864
Met Gly Val Lys Ile Met Leu Leu Ala Gly Gly Asp Leu Ile Glu Ser
        275                 280                 285 atg ggc gag cct cat gtg tgg gct gat tca gac ctg cac cat att ttg      912
Met Gly Glu Pro His Val Trp Ala Asp Ser Asp Leu His His Ile Leu
    290                 295                 300 ggt aat tat gga tgt ttg atc gtg gaa agg act ggt tct gat gtt agg      960
Gly Asn Tyr Gly Cys Leu Ile Val Glu Arg Thr Gly Ser Asp Val Arg
305                 310                 315                 320 tcc ttc ttg ctt tcc cat gat atc atg tat gaa cac aga aga aat atc     1008
Ser Phe Leu Leu Ser His Asp Ile Met Tyr Glu His Arg Arg Asn Ile
                325                 330                 335 ctt att atc aaa caa ctt att tac aat gat att tcc tct acg aaa gtg     1056
Leu Ile Ile Lys Gln Leu Ile Tyr Asn Asp Ile Ser Ser Thr Lys Val
            340                 345                 350 cgg ctt ttc atc aga cgt gga atg tca gtt caa tat ctt ctt cca aac     1104
Arg Leu Phe Ile Arg Arg Gly Met Ser Val Gln Tyr Leu Leu Pro Asn
        355                 360                 365 tct gtc atc cgt tac atc caa gag tat aat cta tac att aat caa agt     1152
Ser Val Ile Arg Tyr Ile Gln Glu Tyr Asn Leu Tyr Ile Asn Gln Ser
    370                 375                 380 gaa ccg gtc aag cag gtc ttg gat agc aaa gag tga                     1188
Glu Pro Val Lys Gln Val Leu Asp Ser Lys Glu
385                 390                 395

<210> SEQ ID NO 8
<211> LENGTH: 25
<212> TYPE: DNA
<213> ORGANISM: Artificial Sequence
<220> FEATURE:
<223> OTHER INFORMATION: Synthetic primer

<400> SEQUENCE: 8
gagtcagcat atggcaaaga aatac                                          25

<210> SEQ ID NO 9
<211> LENGTH: 30
<212> TYPE: DNA
<213> ORGANISM: Artificial Sequence
<220> FEATURE:
<223> OTHER INFORMATION: Synthetic primer

<400> SEQUENCE: 9
cccggcaagc ttttatttct tgtttttgag                                     30

<210> SEQ ID NO 10
<211> LENGTH: 21
<212> TYPE: DNA
<213> ORGANISM: Artificial Sequence
<220> FEATURE:
<223> OTHER INFORMATION: Synthetic primer

<400> SEQUENCE: 10
gtctagaatg gcaaagaata c                                              21

<210> SEQ ID NO 11
<211> LENGTH: 49
```

```
<212> TYPE: DNA
<213> ORGANISM: Artificial Sequence
<220> FEATURE:
<223> OTHER INFORMATION: Synthetic primer

<400> SEQUENCE: 11
tttctagagg aataacacca tggatcccac caaagcaccc gattttaaa        49

<210> SEQ ID NO 12
<211> LENGTH: 32
<212> TYPE: DNA
<213> ORGANISM: Artificial Sequence
<220> FEATURE:
<223> OTHER INFORMATION: Synthetic primer

<400> SEQUENCE: 12
aagagctctc actctttgct atccaagacc tg                          32

<210> SEQ ID NO 13
<211> LENGTH: 8
<212> TYPE: PRT
<213> ORGANISM: Unknown
<220> FEATURE:
<223> OTHER INFORMATION: Synthetic peptide

<400> SEQUENCE: 13

Ser Met Pro Gly Met Met Asp Thr
1               5

<210> SEQ ID NO 14
<211> LENGTH: 7
<212> TYPE: PRT
<213> ORGANISM: Unknown
<220> FEATURE:
<223> OTHER INFORMATION: Synthetic peptide

<400> SEQUENCE: 14

Leu Asn Leu Gly Leu Asn Asp
1               5
```